(12) United States Patent
Wang et al.

(10) Patent No.: US 12,357,311 B2
(45) Date of Patent: Jul. 15, 2025

(54) CONDUCTIVE SCAFFOLDS FOR GUIDED NEURAL NETWORK FORMATION

(71) Applicant: The Trustees of The Stevens Institute of Technology, Hoboken, NJ (US)

(72) Inventors: Hongjun Wang, Millburn, NJ (US); Haoyu Wang, Lyndhurst, NJ (US); Juan Wang, Shanghai (CN)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 215 days.

(21) Appl. No.: 18/020,049

(22) PCT Filed: Aug. 6, 2021

(86) PCT No.: PCT/US2021/045117
§ 371 (c)(1),
(2) Date: Feb. 6, 2023

(87) PCT Pub. No.: WO2022/032203
PCT Pub. Date: Feb. 10, 2022

(65) Prior Publication Data
US 2023/0293179 A1    Sep. 21, 2023

Related U.S. Application Data

(60) Provisional application No. 63/063,158, filed on Aug. 7, 2020.

(51) Int. Cl.
| | |
|---|---|
| *A61B 17/11* | (2006.01) |
| *A61L 31/06* | (2006.01) |
| *A61L 31/10* | (2006.01) |
| *A61L 31/14* | (2006.01) |
| *B33Y 10/00* | (2015.01) |

(Continued)

(52) U.S. Cl.
CPC .......... *A61B 17/1128* (2013.01); *A61L 31/06* (2013.01); *A61L 31/10* (2013.01);
(Continued)

(58) Field of Classification Search
CPC ..... A61B 17/1128; B33Y 10/00; B33Y 70/00; B33Y 80/00; A61L 31/06
See application file for complete search history.

(56) References Cited

PUBLICATIONS

Zhou et al., Graphene Functionalized Scaffolds Reduce the Inflammatory Response and Supports Endogenous Neuroblast Migration when Implanted in the Adult Brain, Mar. 15, 2016, PLoS One (Year: 2016).*

(Continued)

*Primary Examiner* — Nathan T Leong
(74) *Attorney, Agent, or Firm* — Clark Hill PLC; Ralph W. Selitto; John K. Kim

(57) ABSTRACT

The present invention relates generally to the manufacture of conductive scaffolds of micro and/or nanofibers with the help of different printing techniques (e.g., near-field electrostatic printing, inkjet printing), such scaffolds enabling the formation of two-dimensional (2D) or three-dimensional (3D) neural networks to mimic the native counterparts. Applications of such patterned conductive scaffolds include, but are not limited to, an engineered conduit for guiding the differentiation and outgrowth of neural cells in peripheral nerve damage or in large-volume spinal cord injury under the electrical stimulation. Meanwhile, the scaffolds could also locally deliver various biomolecules in conjunction with electrical stimulation for facilitated nervous system regeneration.

14 Claims, 68 Drawing Sheets

(51) Int. Cl.
    *B33Y 40/20*     (2020.01)
    *B33Y 70/00*     (2020.01)
    *B33Y 80/00*     (2015.01)
    *B41M 5/00*     (2006.01)
    *A61B 17/00*     (2006.01)
    *A61N 1/36*     (2006.01)

(52) U.S. Cl.
    CPC ............... *A61L 31/14* (2013.01); *B33Y 10/00* (2014.12); *B33Y 40/20* (2020.01); *B33Y 70/00* (2014.12); *B33Y 80/00* (2014.12); *B41M 5/0047* (2013.01); *A61B 2017/00526* (2013.01); *A61L 2420/02* (2013.01); *A61L 2430/32* (2013.01); *A61N 1/36103* (2013.01)

(56) References Cited

PUBLICATIONS

International Preliminary Report on Patentability for PCT Application Serial No. PCT/US2021/045117, Issued Feb. 7, 2023.

International Search Report and Written Opinion for PCT Application Serial No. PCT/US2021/045117, Issued Sep. 11, 2021.

Wang Juan et al. "In Vitro and In Vivo Studies of Electroactive Reduced Graphene Oxide-Modified Nanofiber Scaffolds for Peripheral Nerve Regeneration" Acta Biomaterialia vol. 84, Nov. 22, 2018.

Sanjairaj Vijayavenkataraman et al. "3D-Printed PCL/rGO Conductive Scaffolds for Peripheral Nerve Injury Repair" Artificial Organs, vol. 43, No. 5, Nov. 12, 2018.

Raslan Ahmed et al. "Graphene Oxide and Reduced Graphene Oxide-Based Scaffolds in Regenerative Medicine" International Journal of Pharmaceutics, Elsevier, NL, vol. 580, Mar. 13, 2020.

Hyunwoo Kim et al. "Graphene Oxide—Polyethylenimine Nanoconstruct as a Gene Delivery Vector and Bioimaging Tool" Bioconjugate Chemistry, vol. 22, No. 12, Dec. 21, 2011.

Carvalho Cristiana et al. "Nanotechnology in Peripheral Nerve Repair and Reconstruction" Advanced Drug Delivery Reviews, Elsevier, vol. 148, Jan. 11, 2019.

* cited by examiner

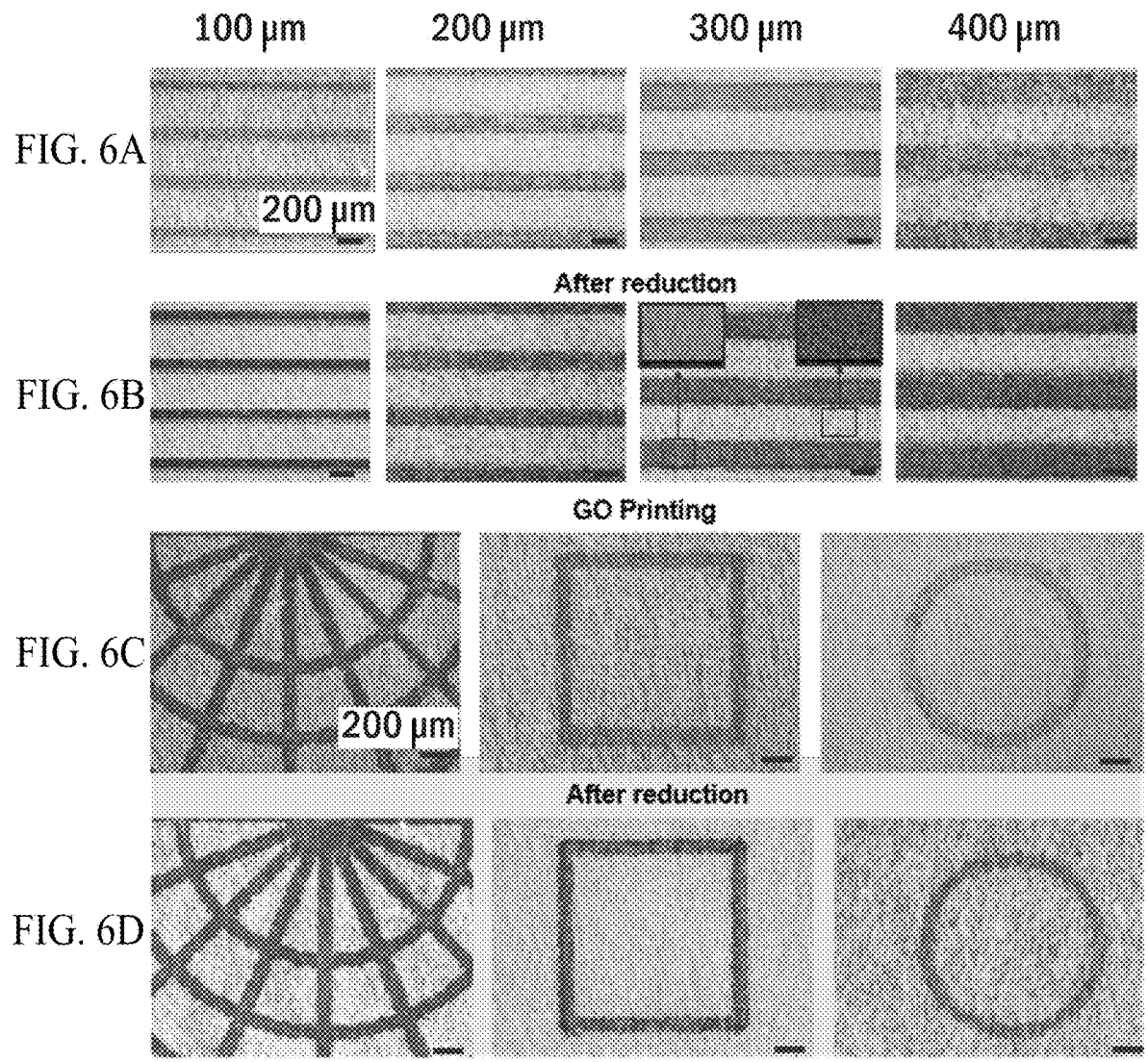

4 LAYERS rGO PRINTING

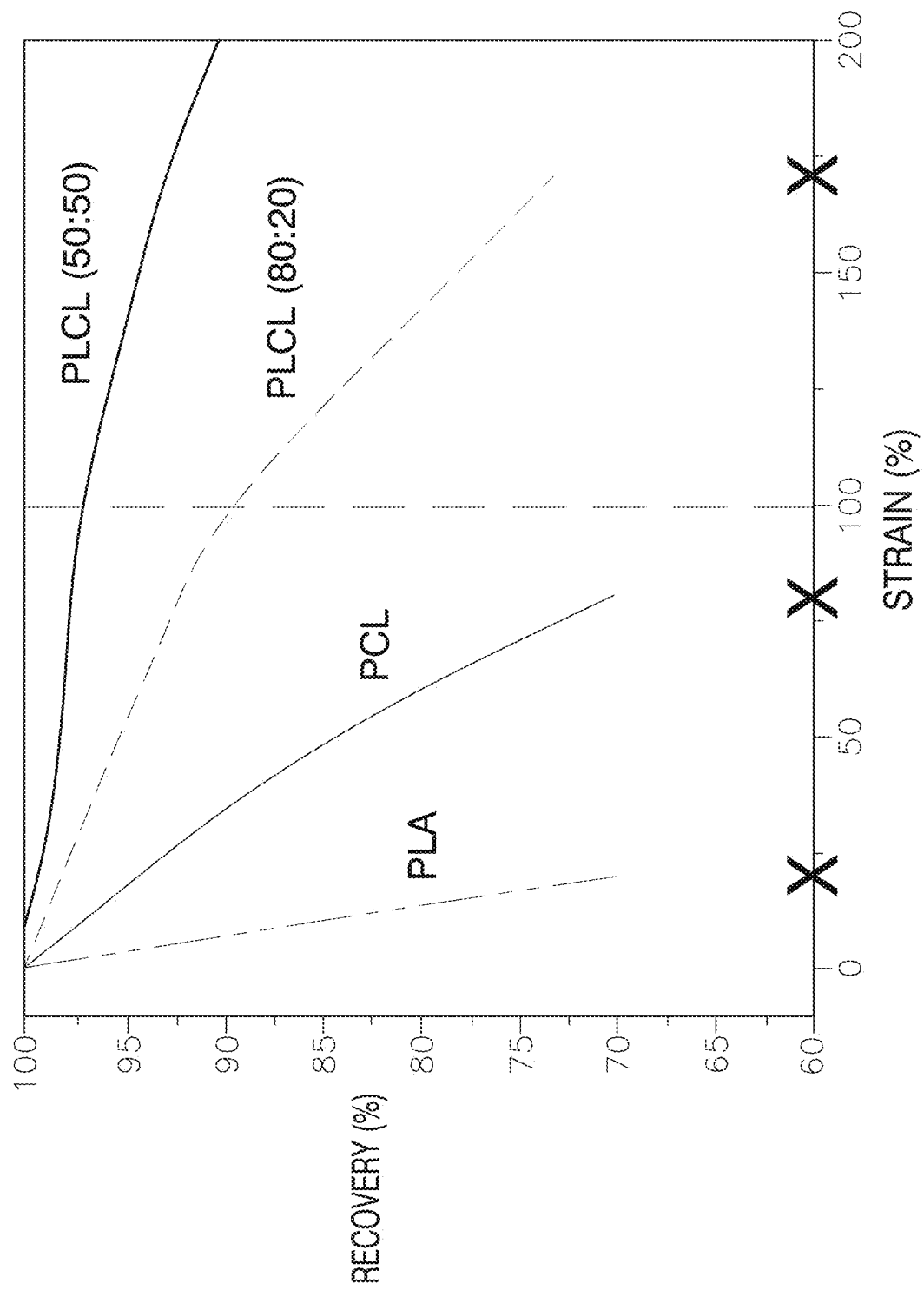

FIG. 9D CONTROL GROUP W/O ES

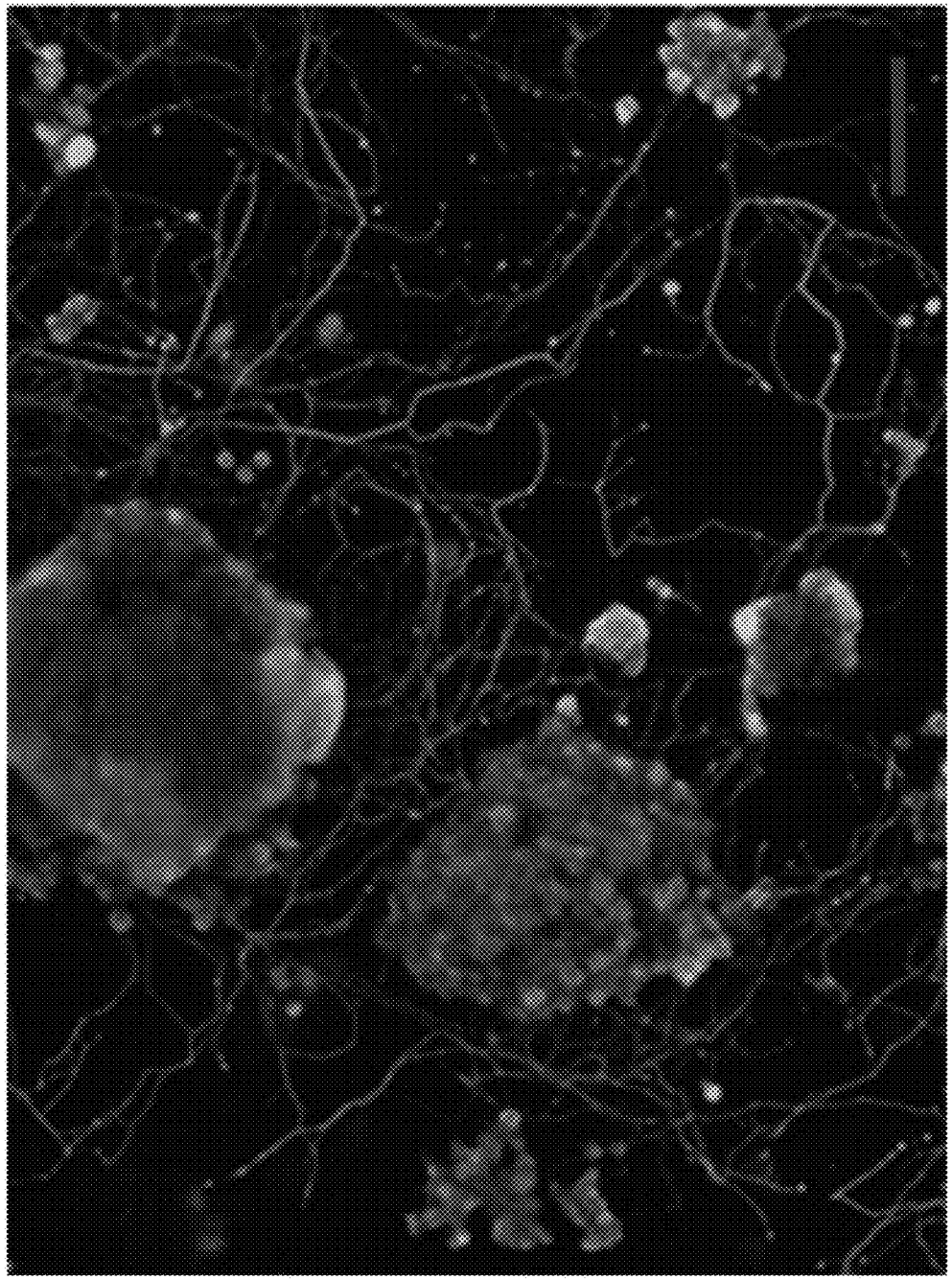
FIG. 9E 150mv/cm, 7 DAYS

100mv/cm, 14 DAYS

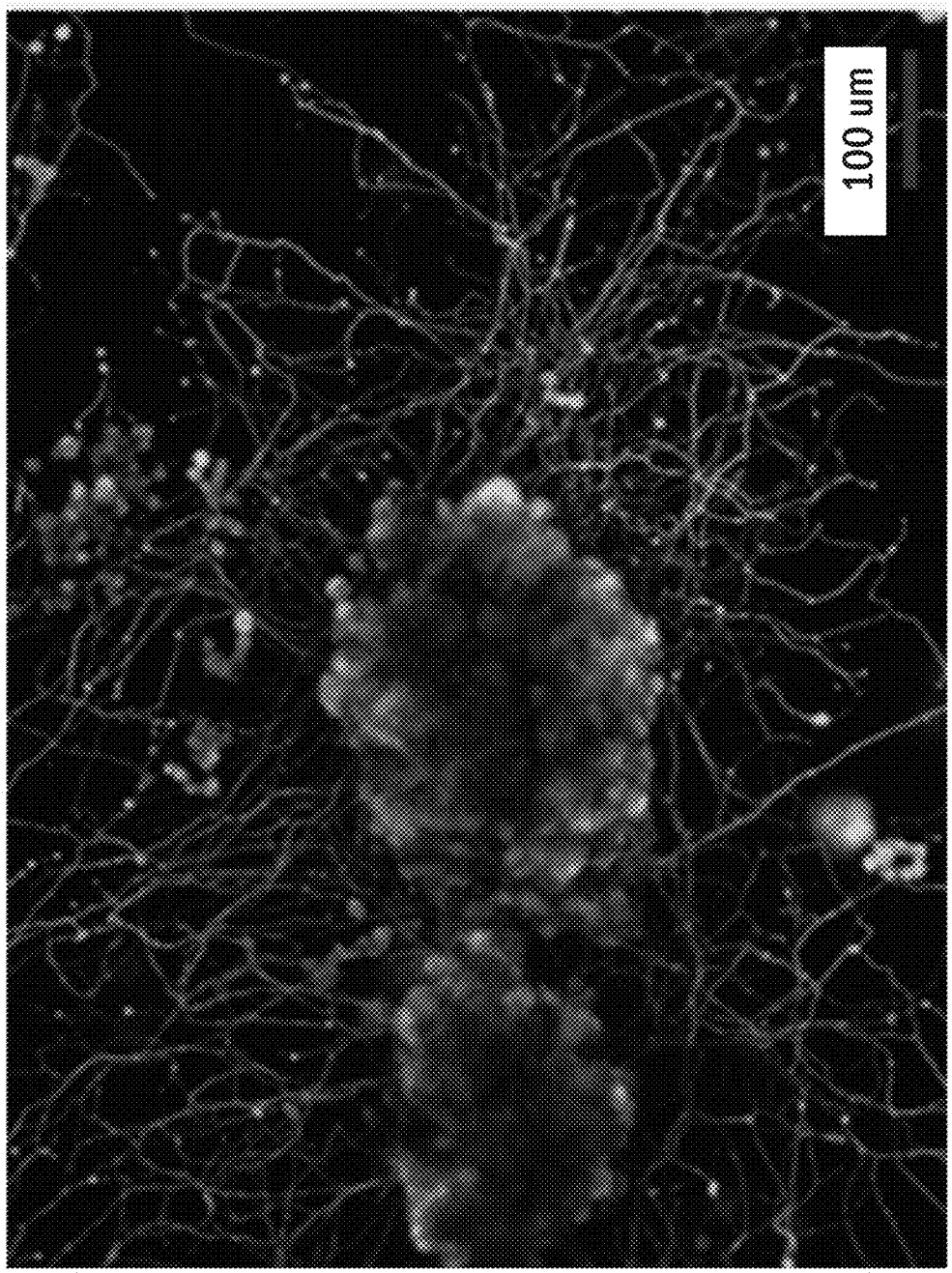
FIG. 9G 150mv/cm, 14 DAYS

TUBULIN/PHALLOIDIN/DAPI
100mv/cm, 14 days

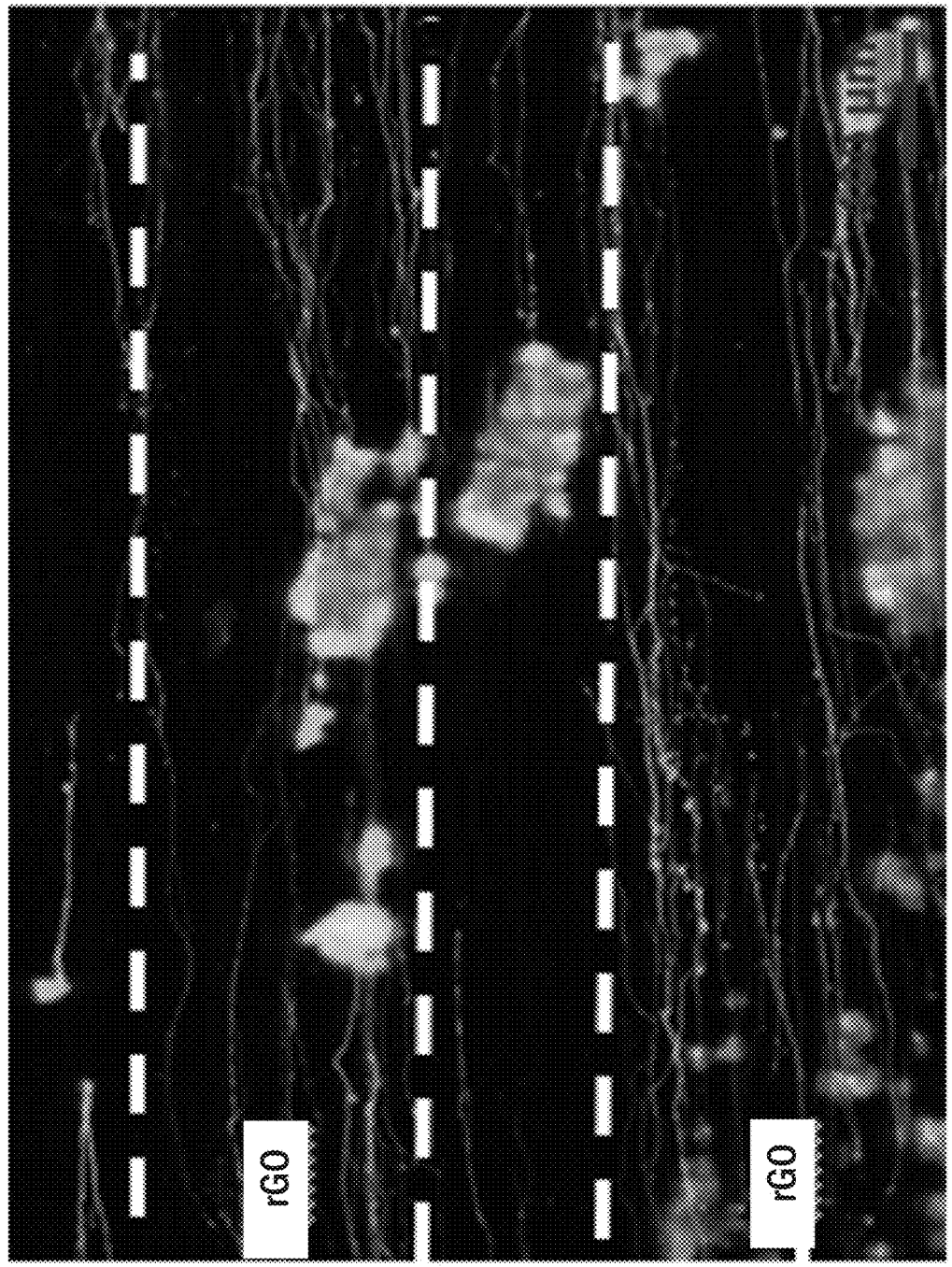

TUBULIN/PHALLOIDIN/DAPI
150mv/cm, 14 days

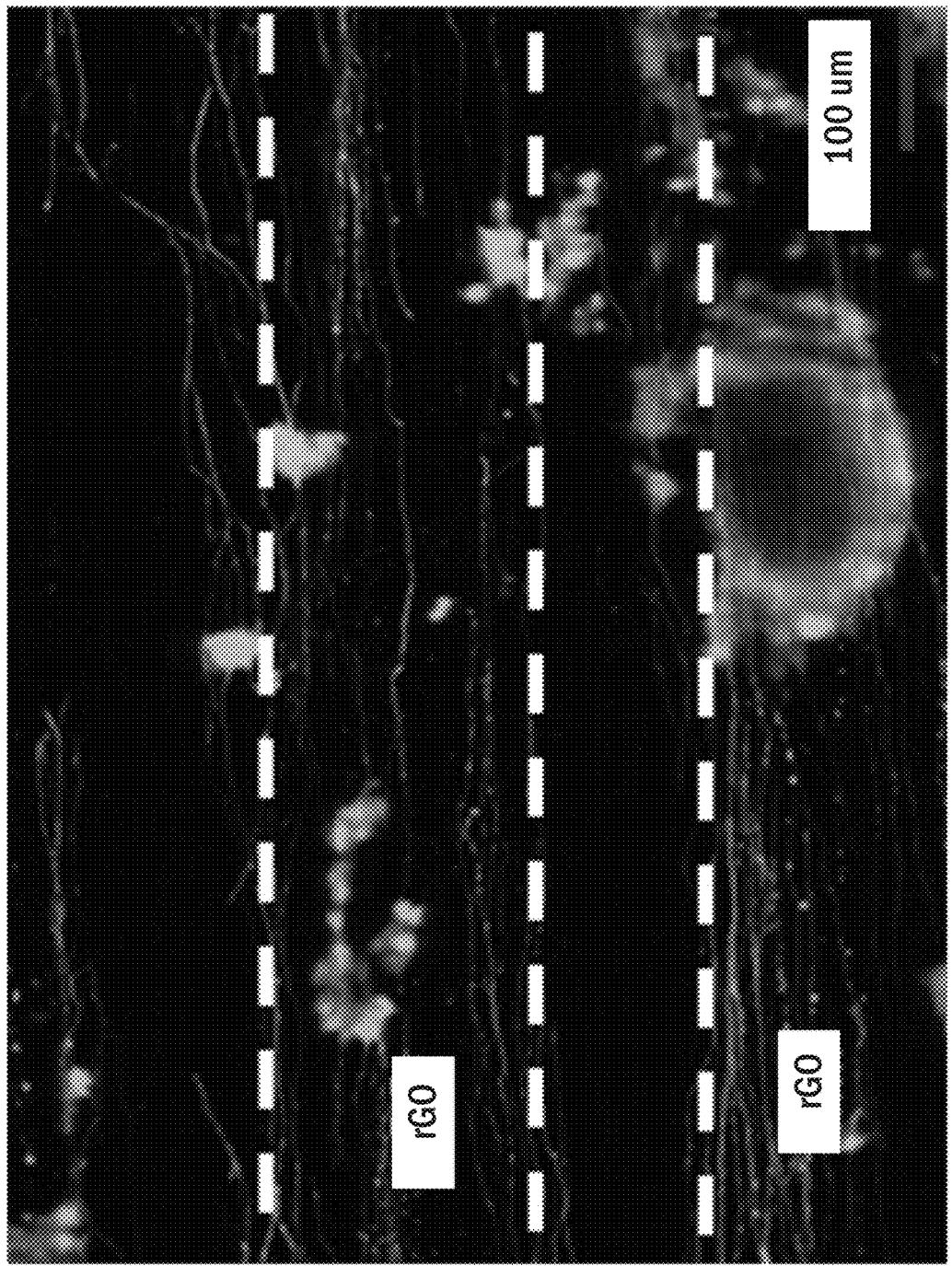

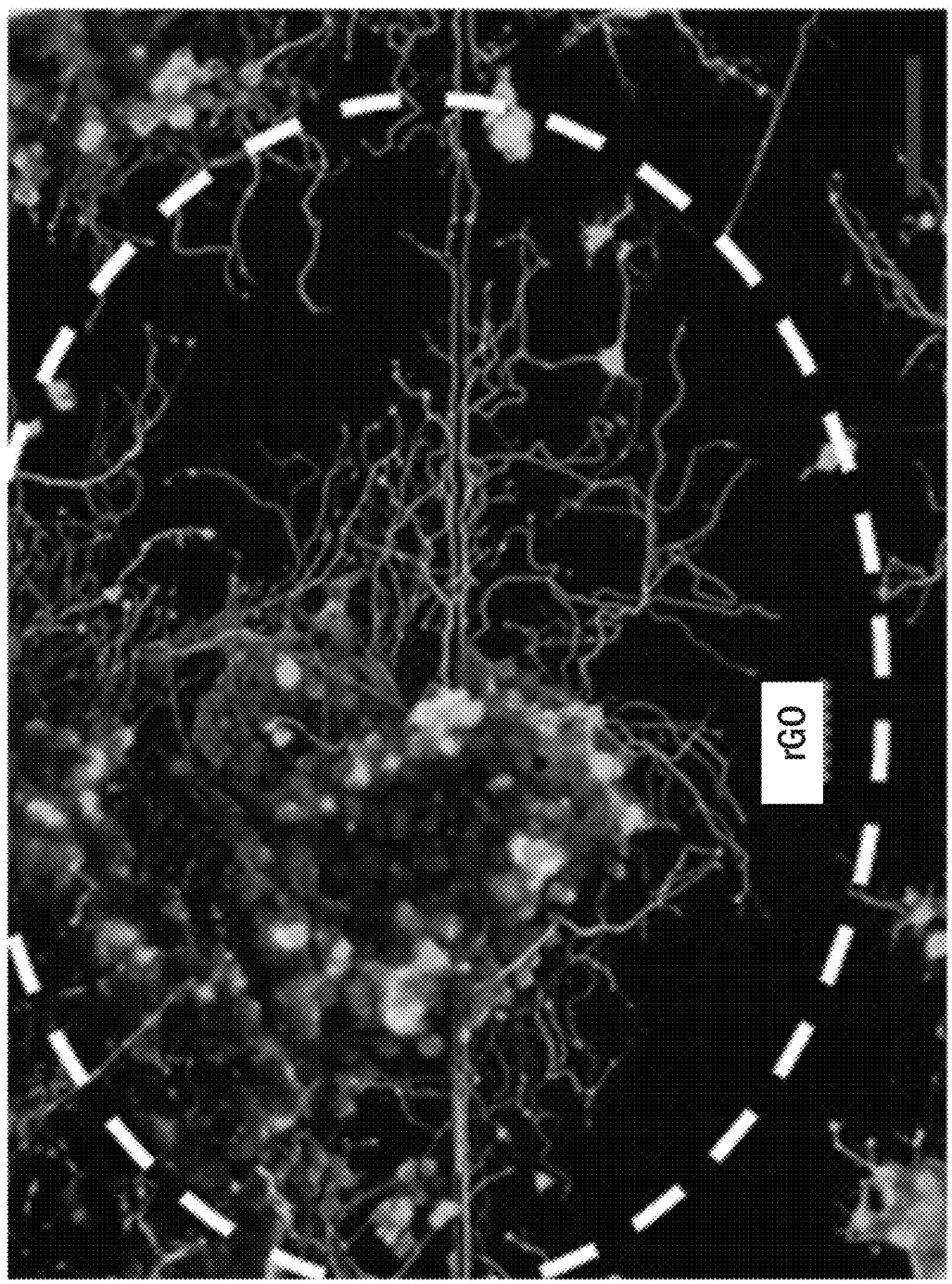
FIG. 9L 100mv/cm, 14 days

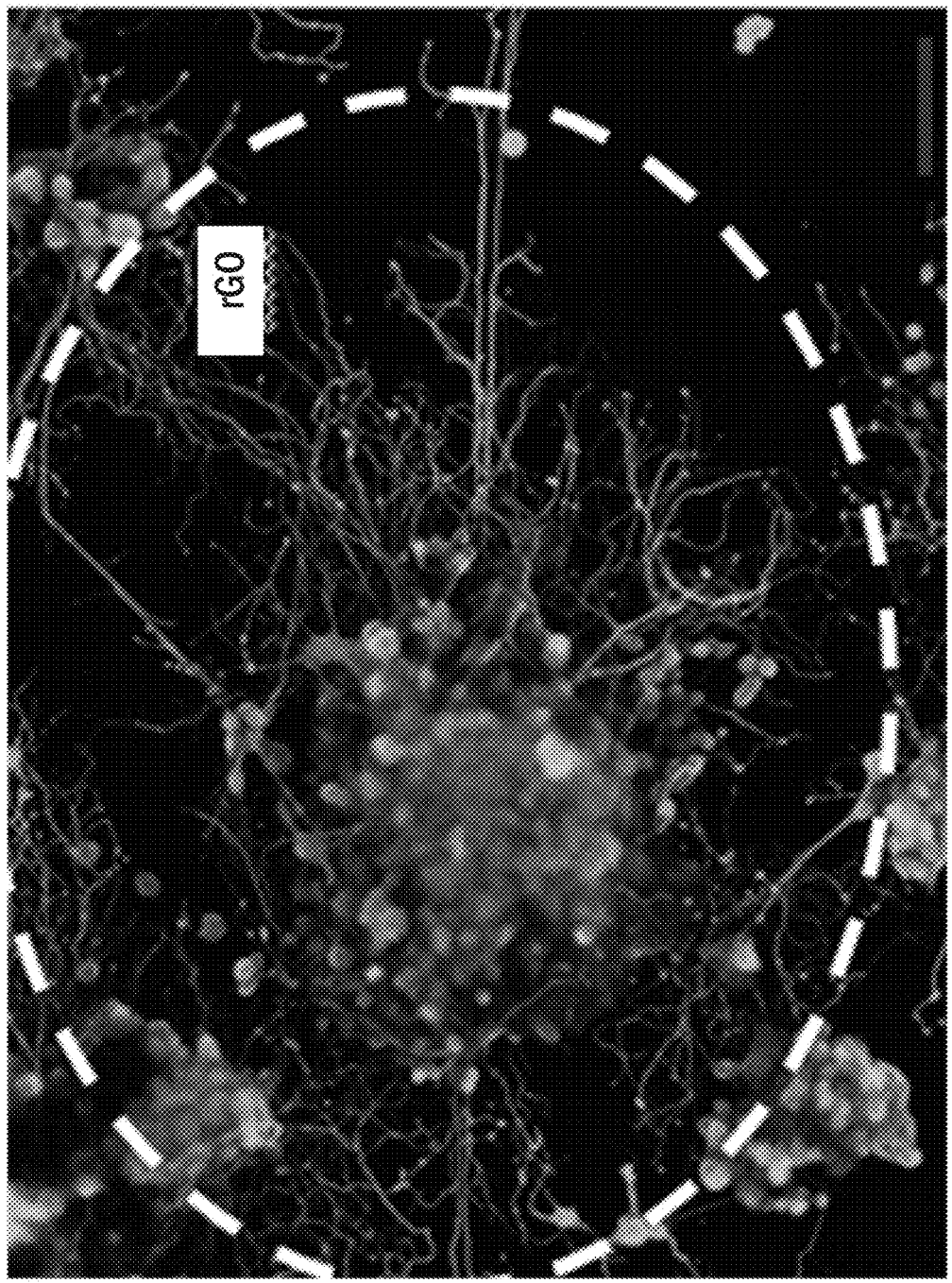
FIG. 9N 150mv/cm, 14 days

β-TUBULIN/DAPI/PHALLOIDIN
WITHOUT ES

β-TUBULIN/DAPI/PHALLOIDIN WITHOUT ES

β-TUBULIN/DAPI/PHALLOIDIN
ES=50mV/cm

β-TUBULIN/DAPI/PHALLOIDIN
ES=50mV/cm

β-TUBULIN/DAPI/PHALLOIDIN
ES=100mV/cm

β-TUBULIN/DAPI/PHALLOIDIN
ES=100mV/cm

β-TUBULIN/DAPI/PHALLOIDIN
ES=150mV/cm

β-TUBULIN/DAPI/PHALLOIDIN
ES=150mV/cm

β-TUBULIN/DAPI/PHALLOIDIN
ES=200mV/cm

β-TUBULIN/DAPI/PHALLOIDIN
ES=200mV/cm

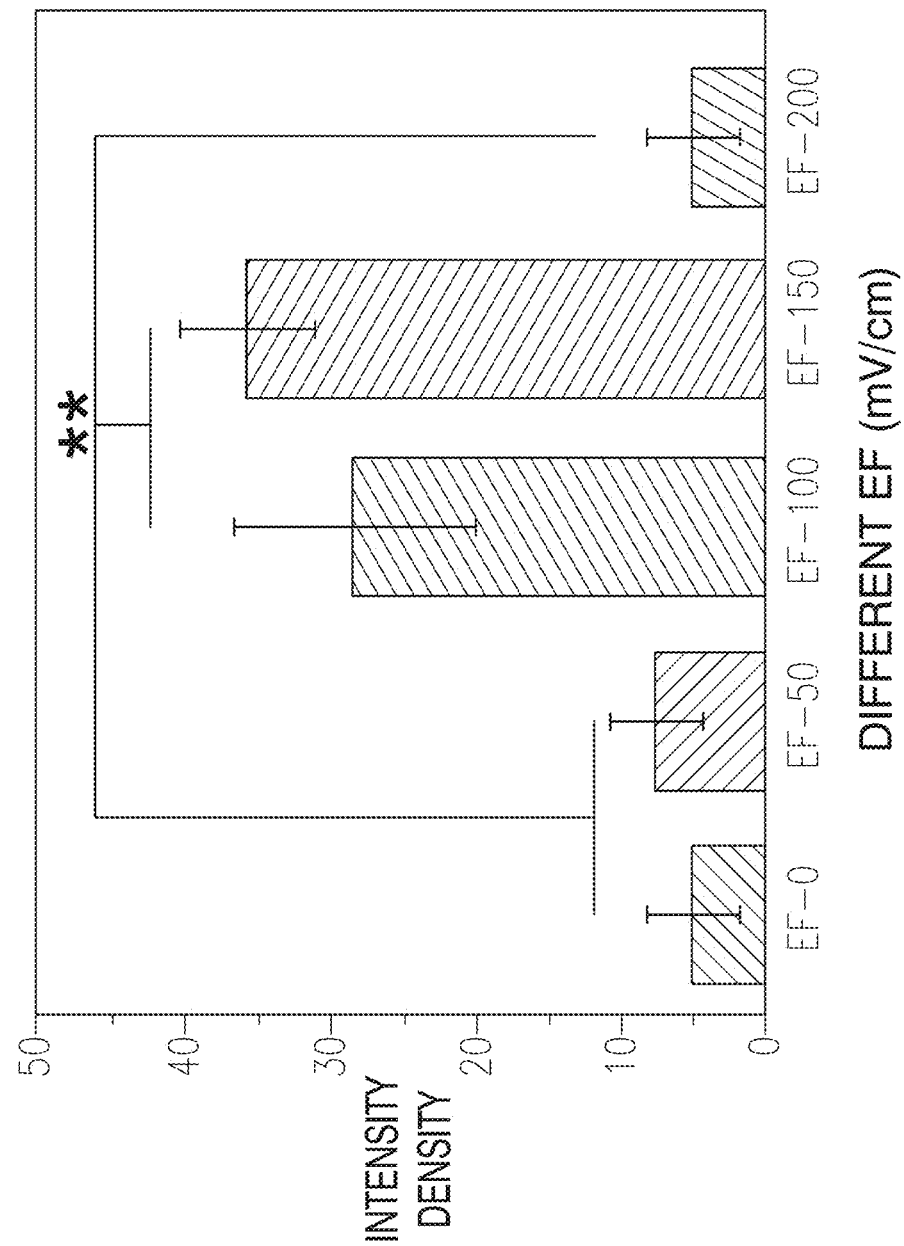

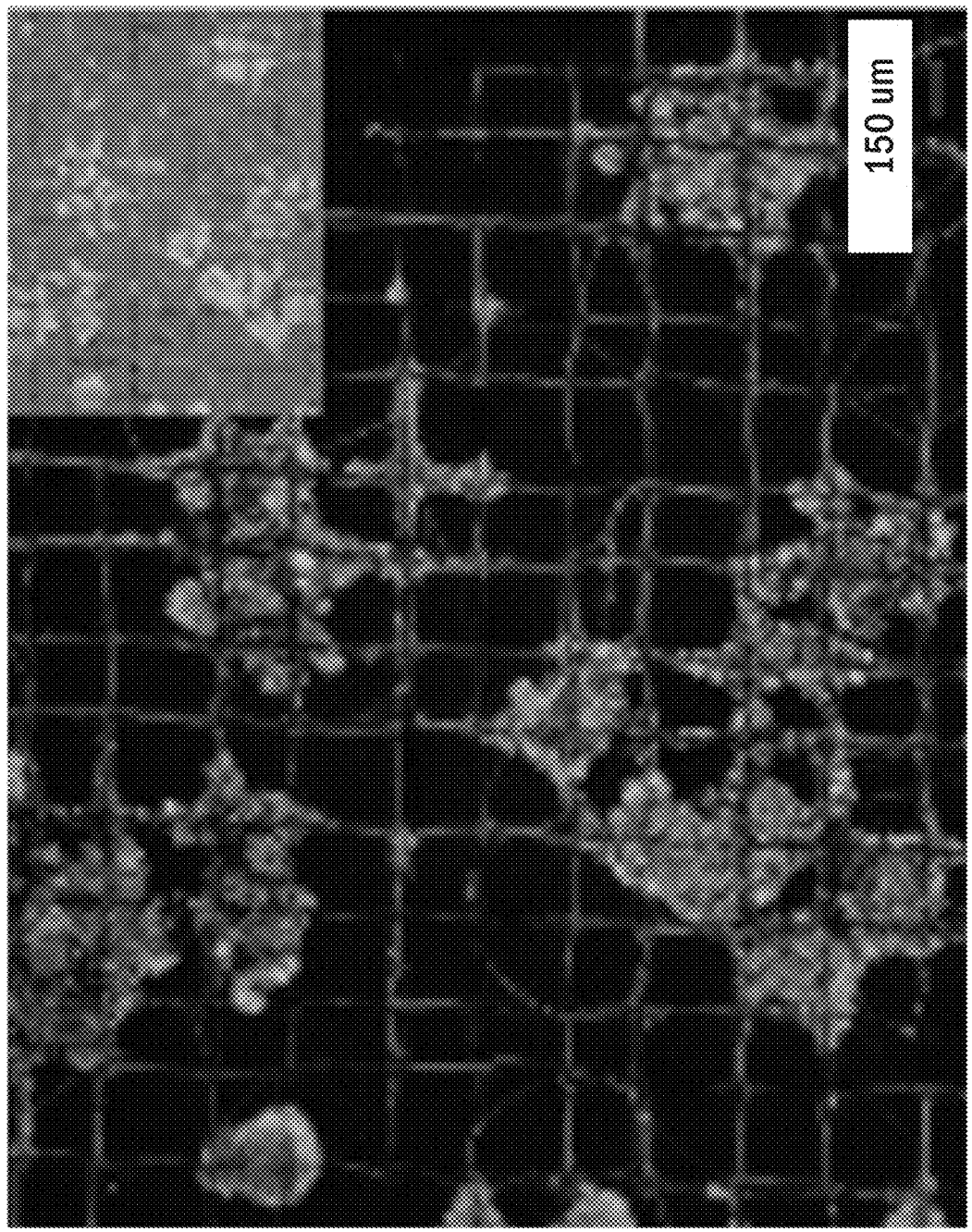
FIG. 15A1
D=16 um

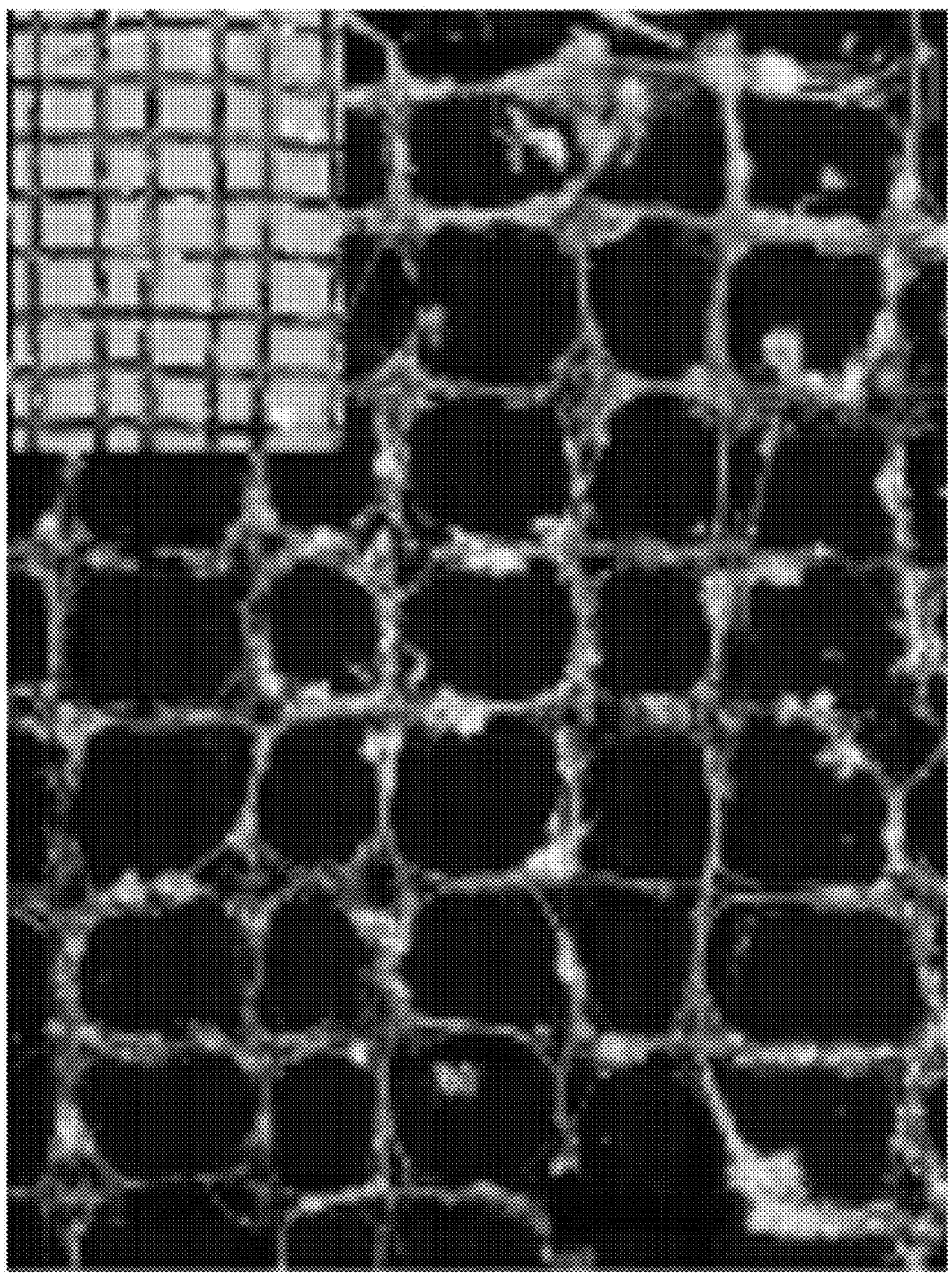
FIG. 15A2
D=72 um

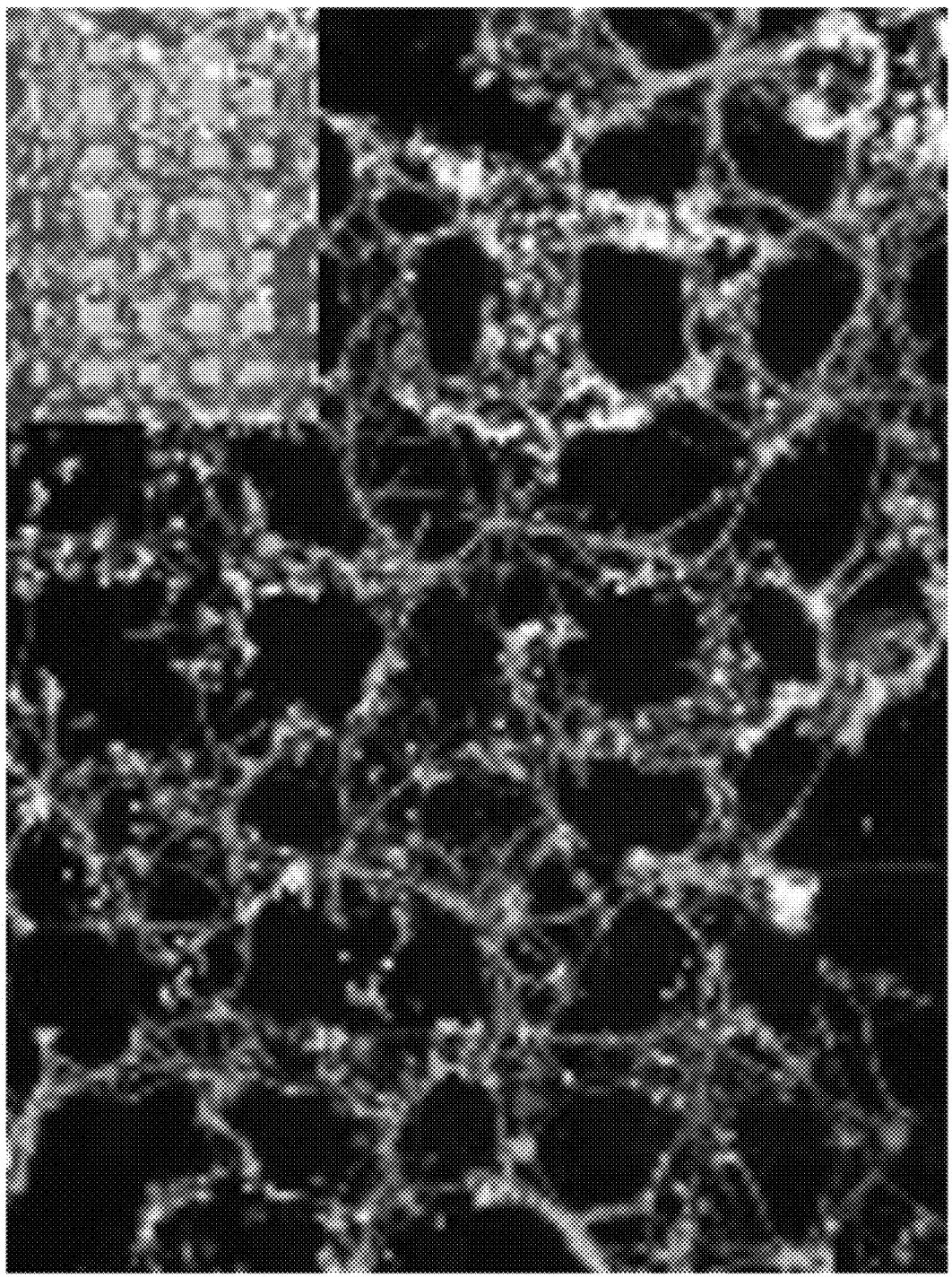
FIG. 15A3
D=149 um

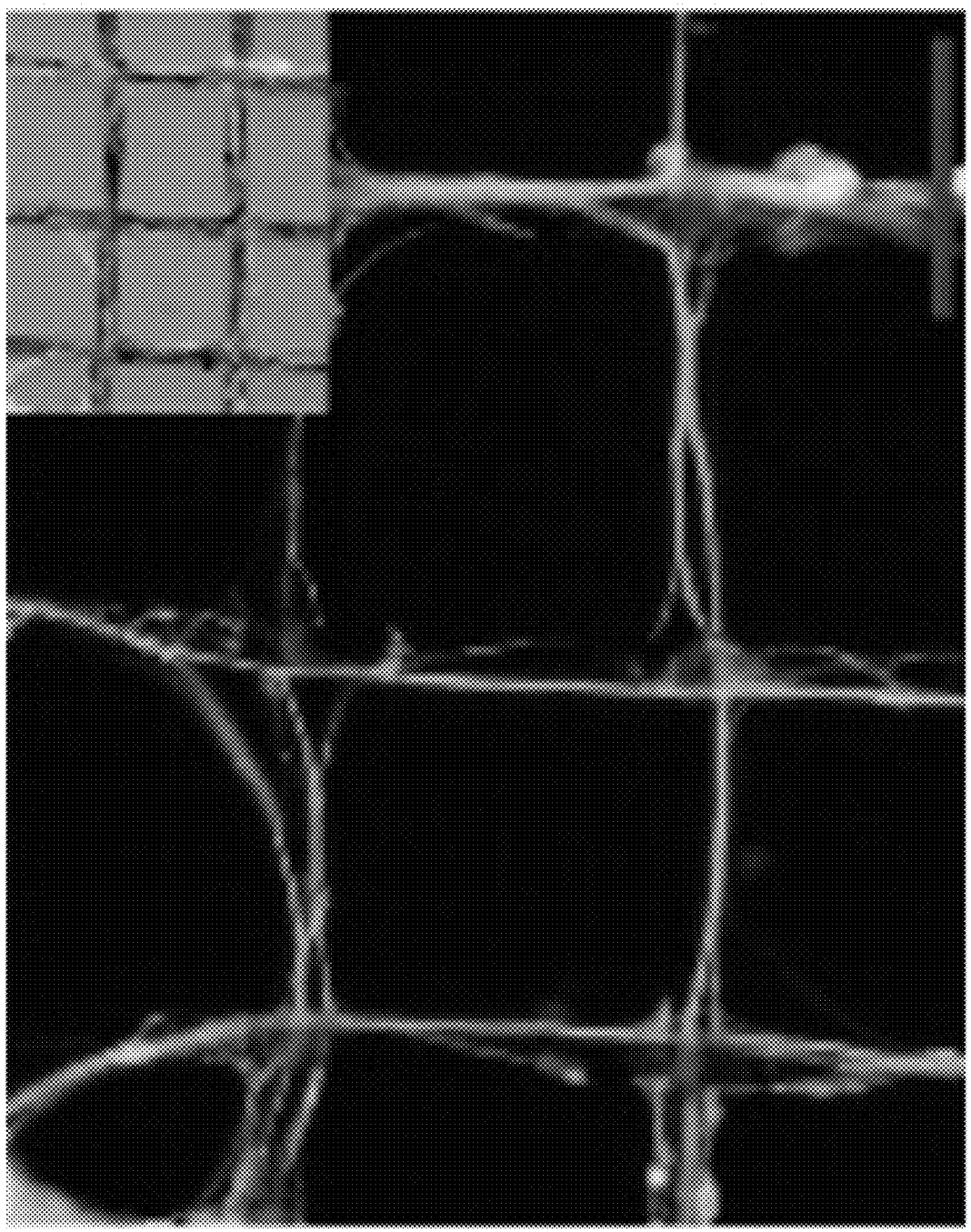
FIG. 15A4
D=16 um

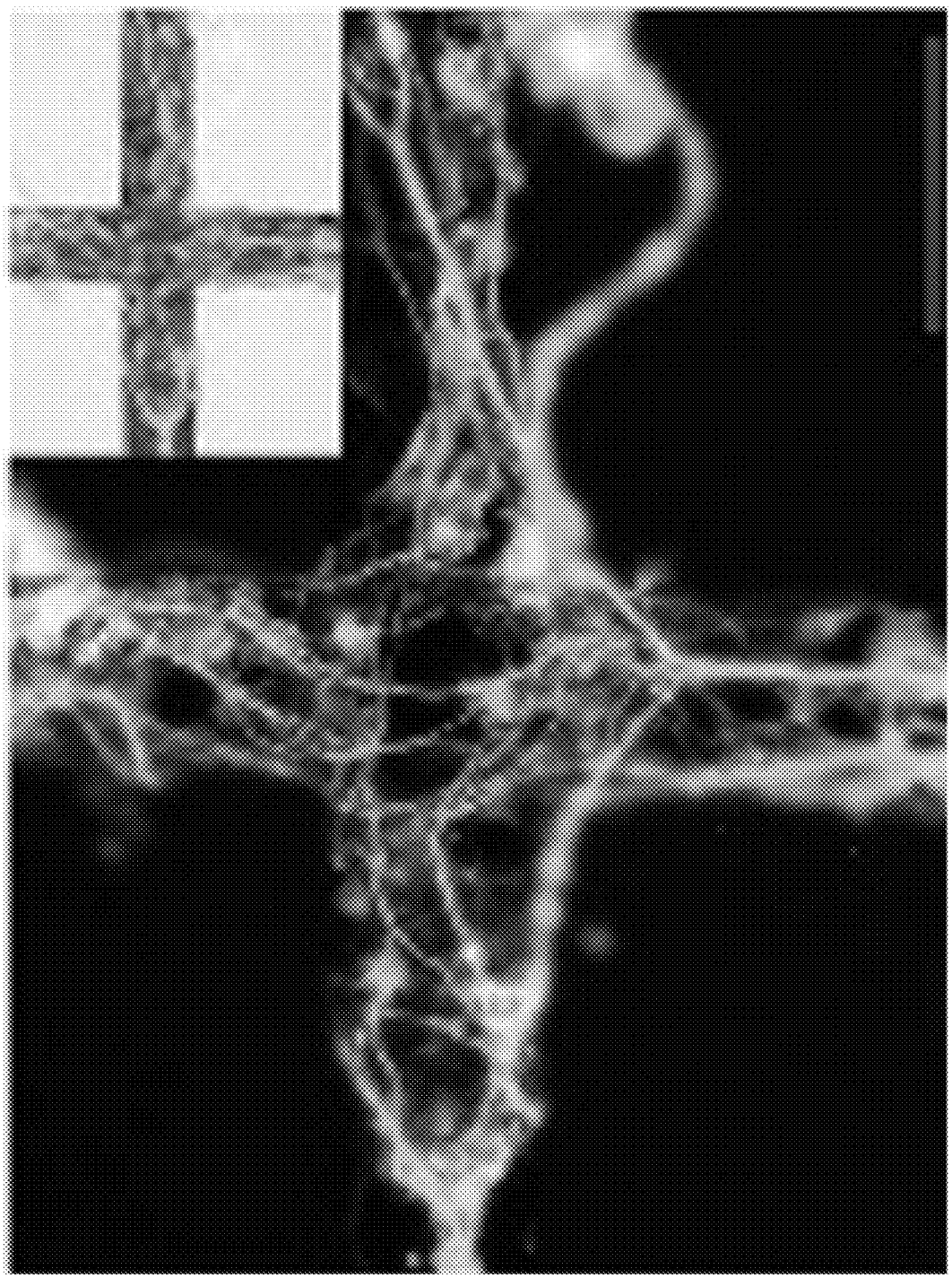
FIG. 15A5
D=72 um

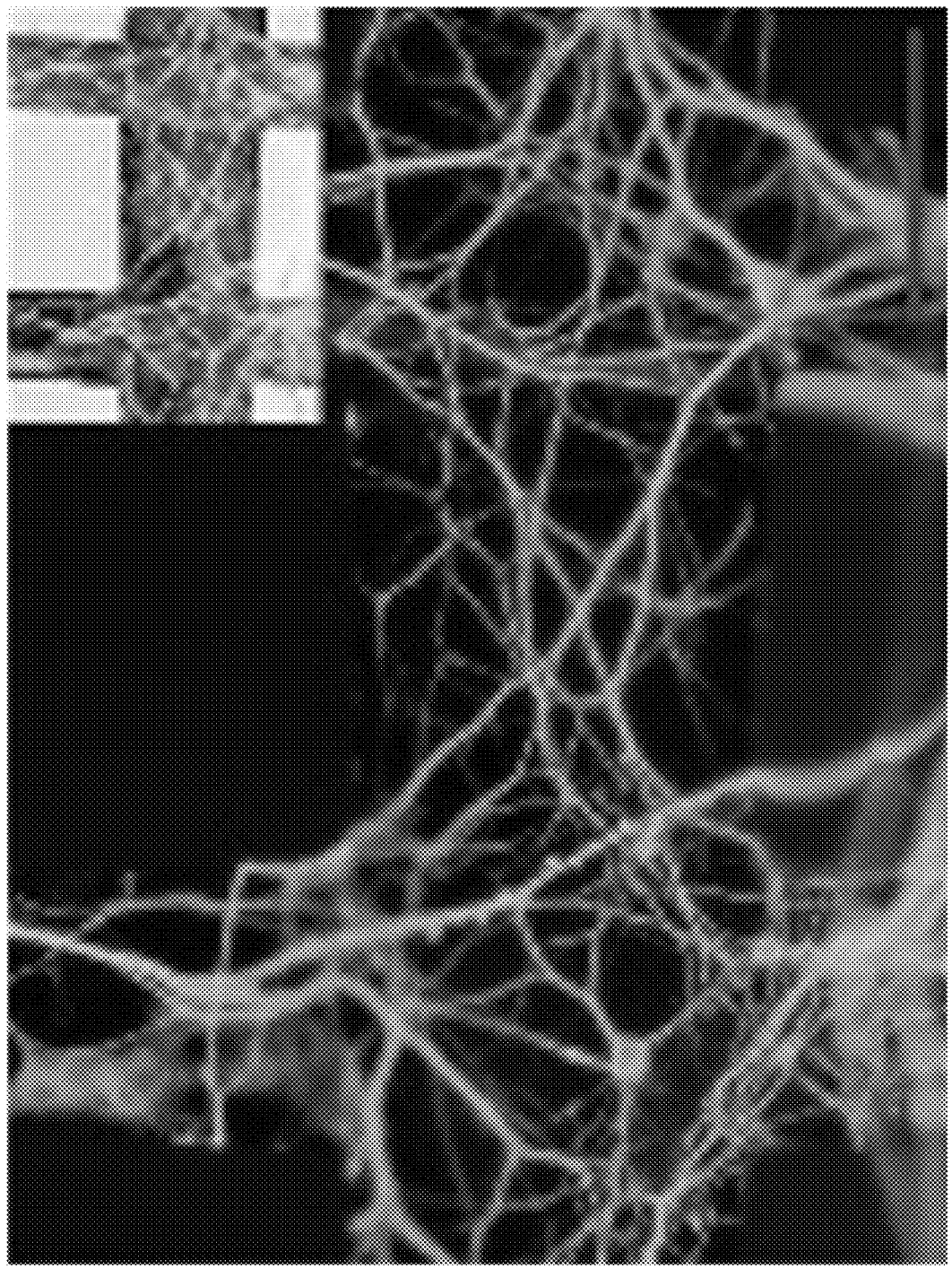
FIG. 15A6
D=149 um

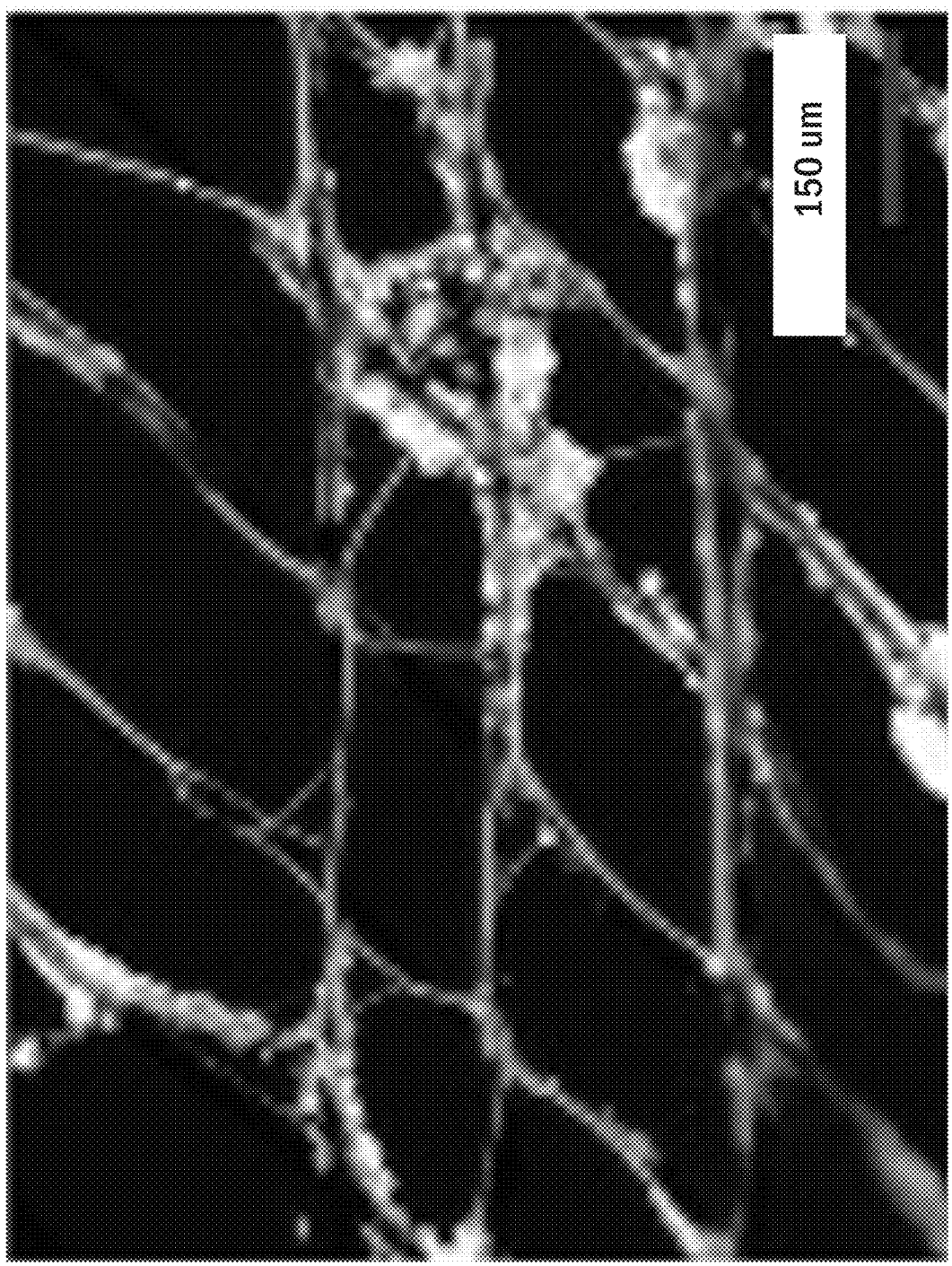
FIG. 15B1
45° w/ES

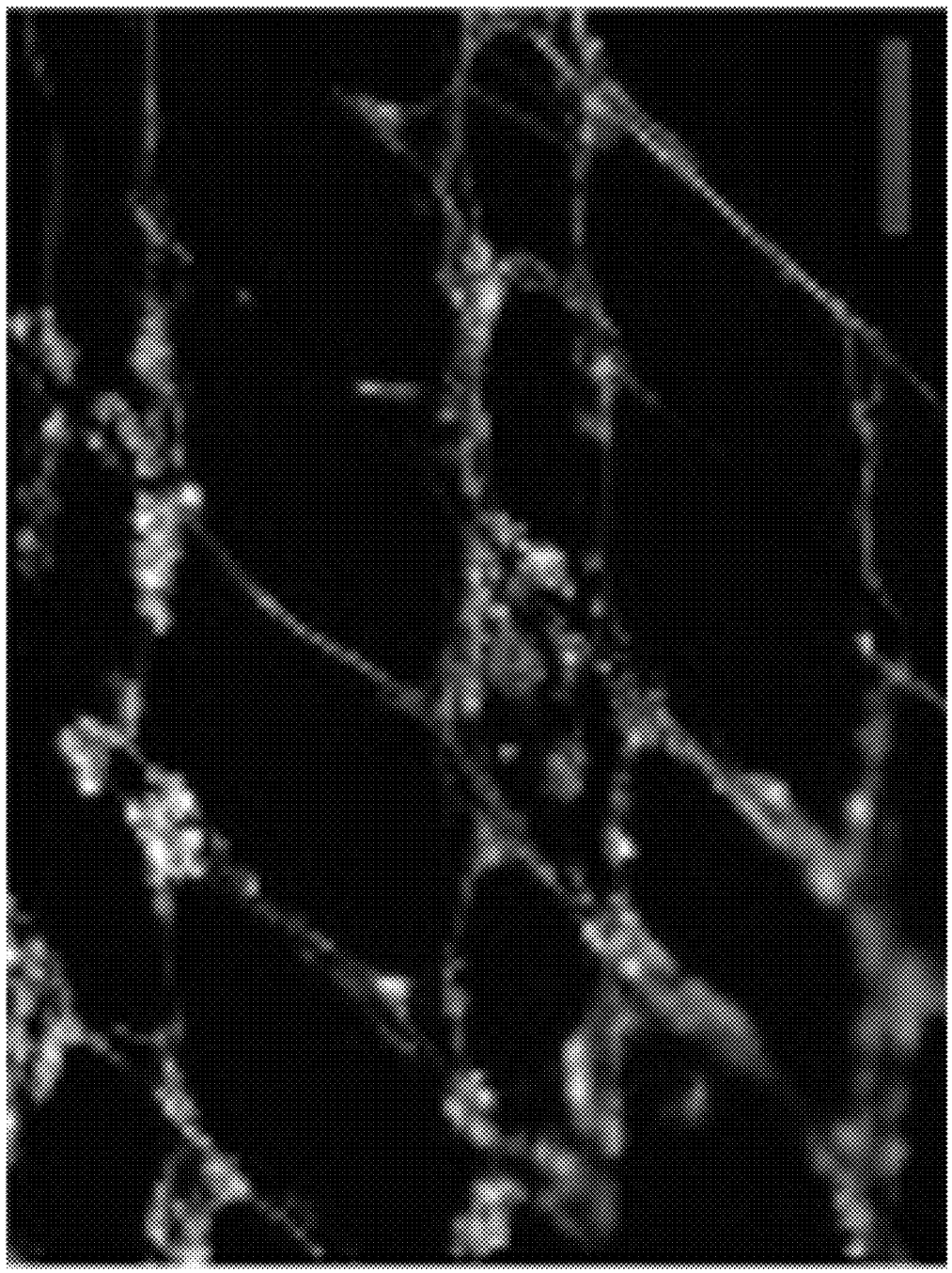
FIG. 15B2
45° w/o ES

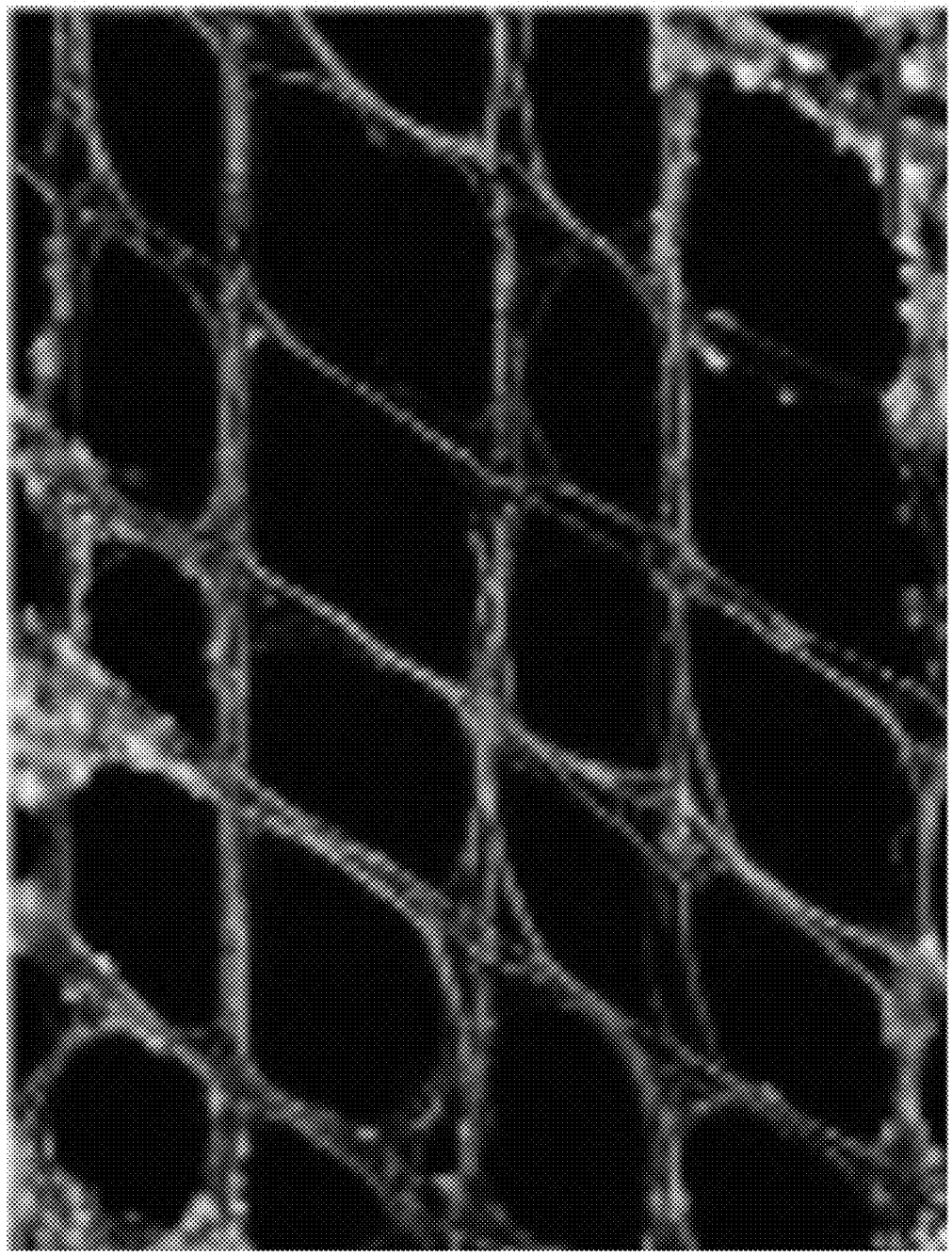
FIG. 15B3
60° w/ES

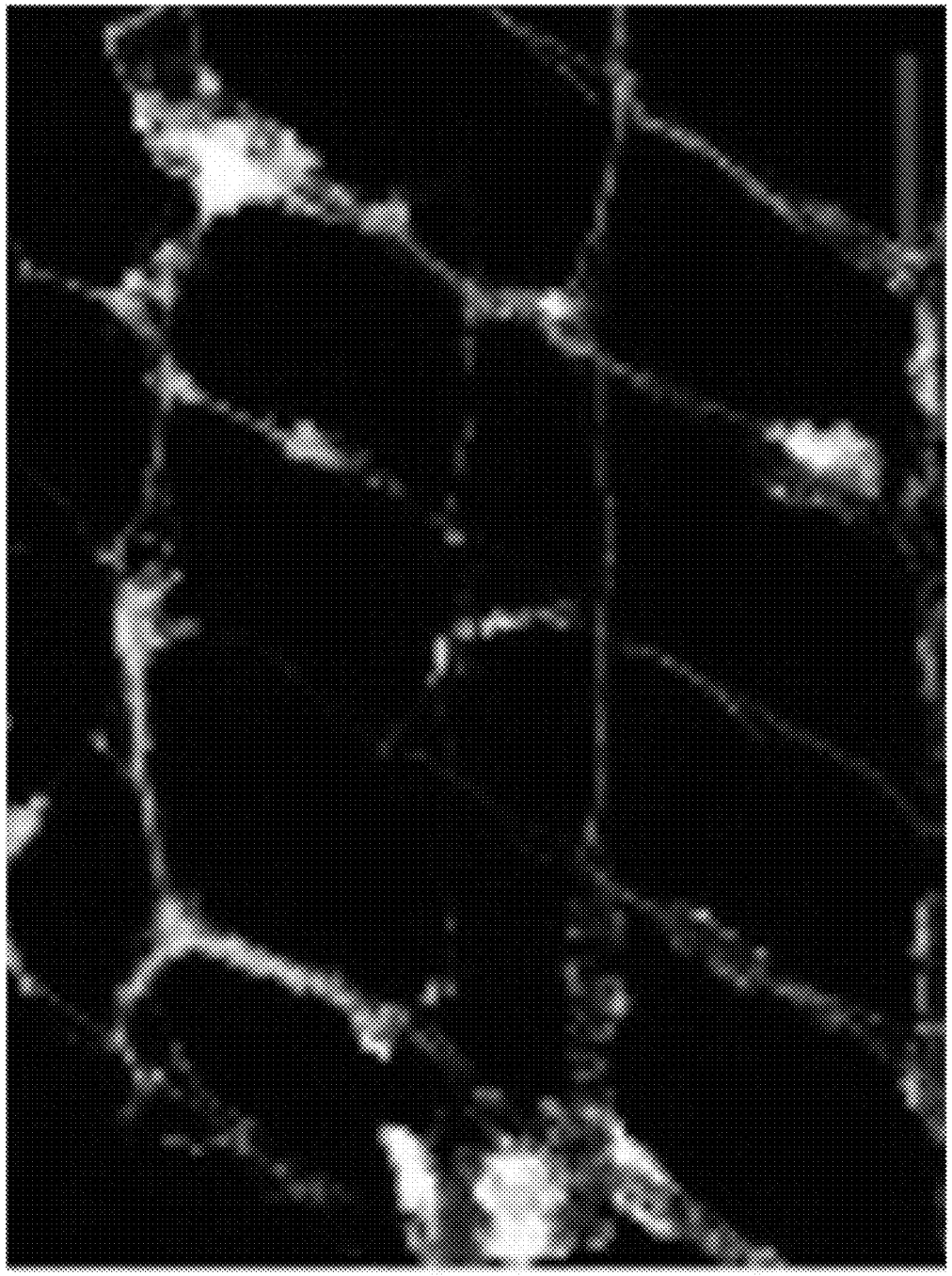
FIG. 15B4 60° w/o ES

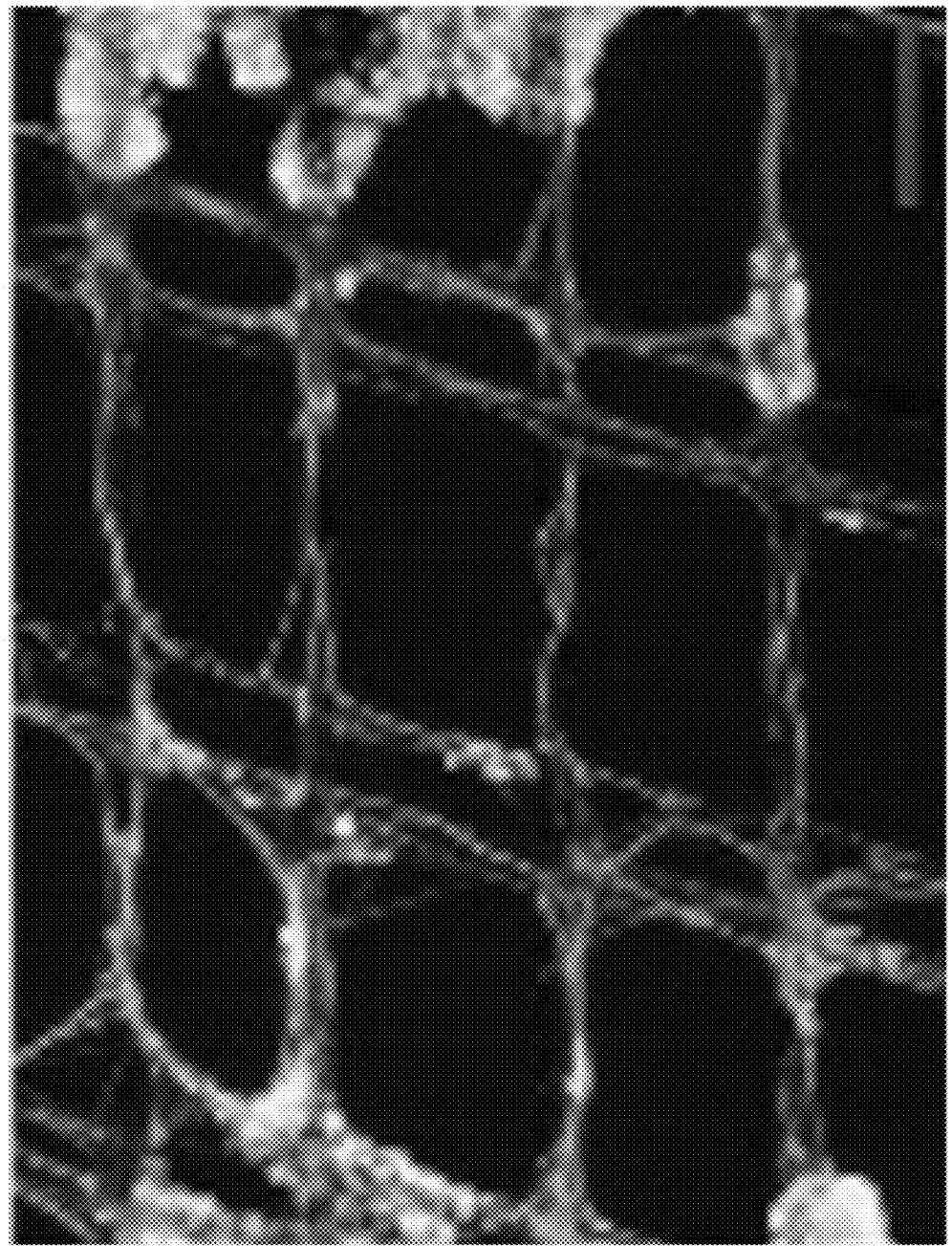
FIG. 15B5
75°w/ES

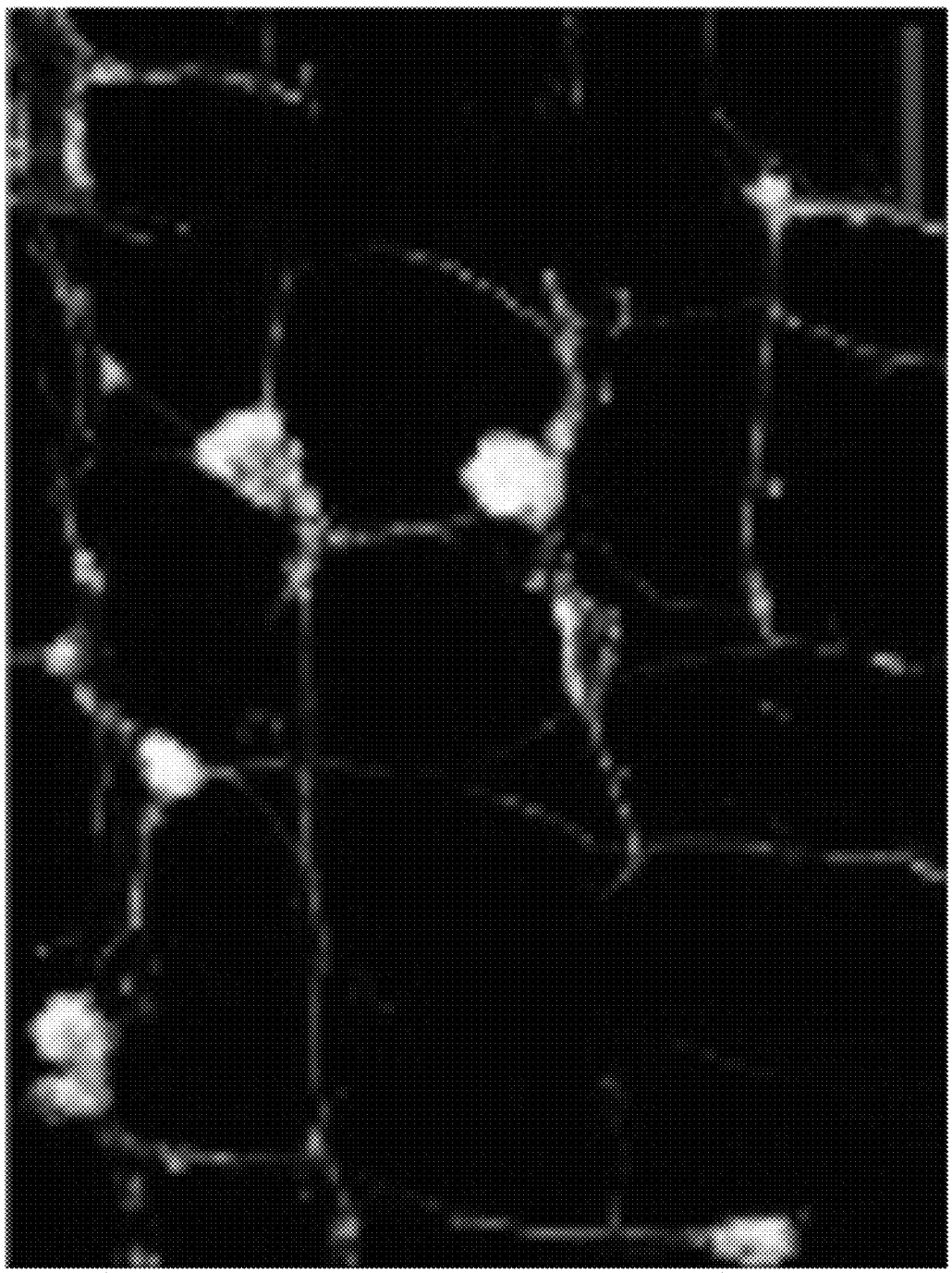
FIG. 15B6
75° w/o ES

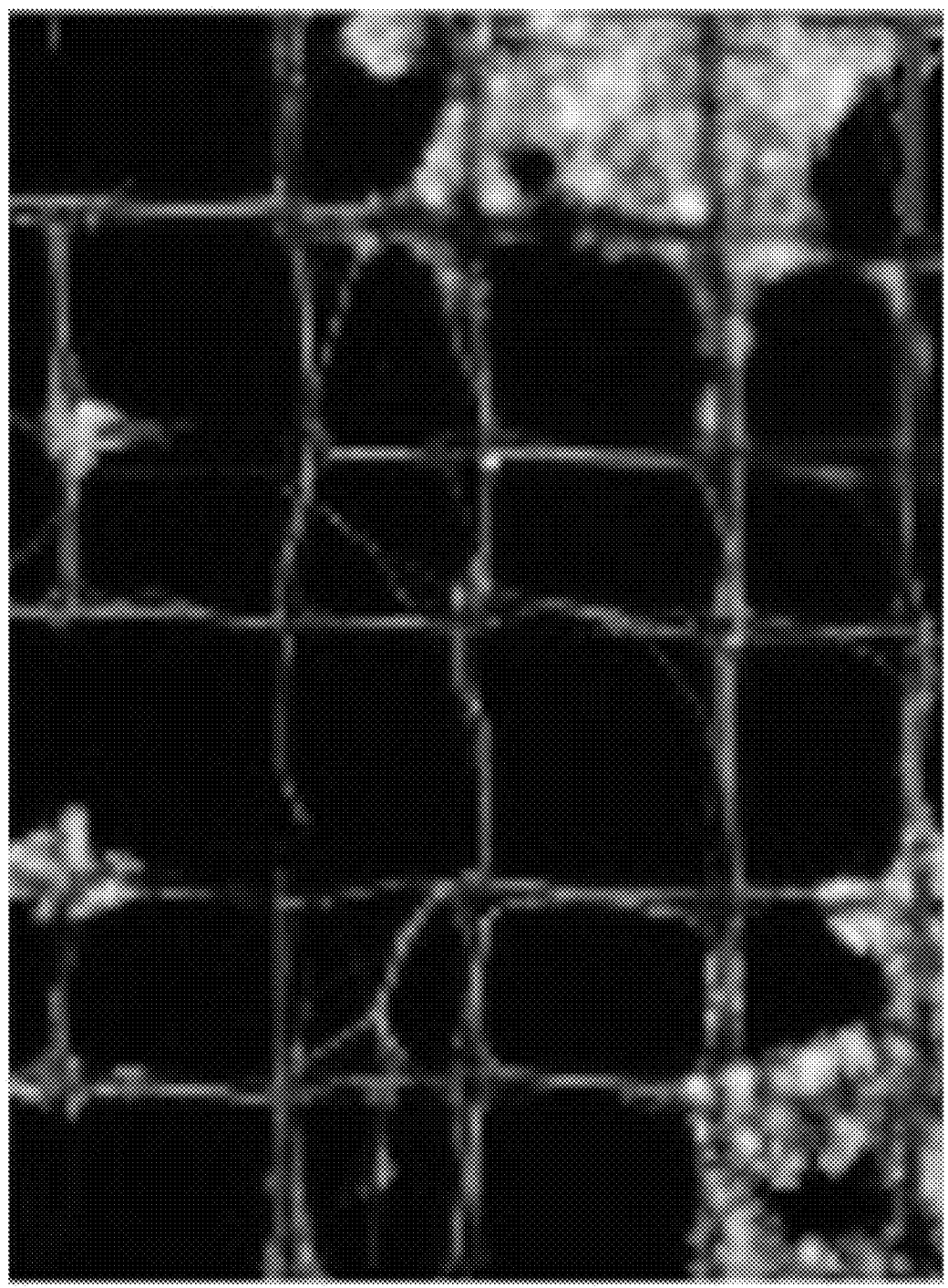
FIG. 15B7
90°w/ES

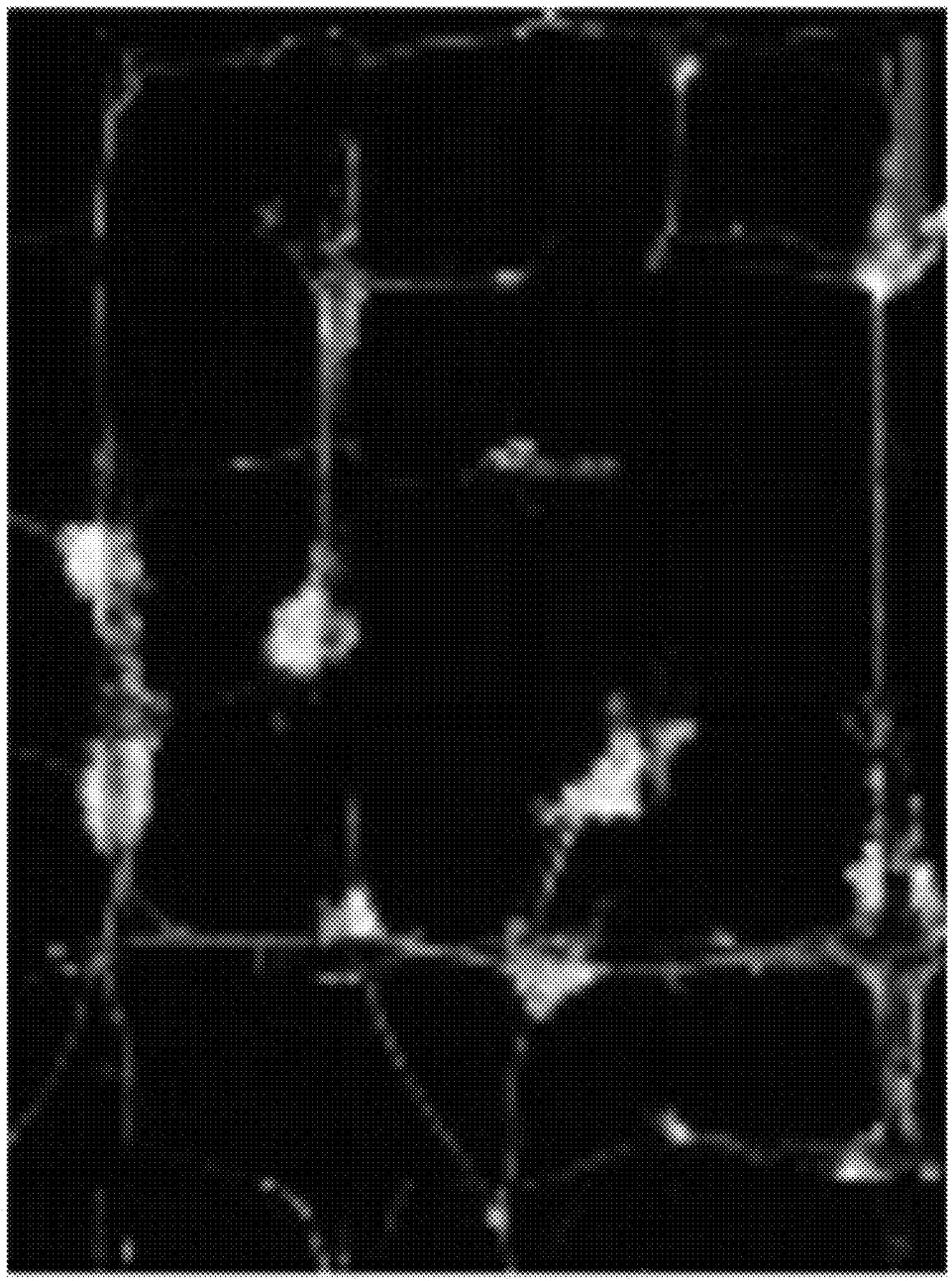
FIG. 15B8
90° w/o ES

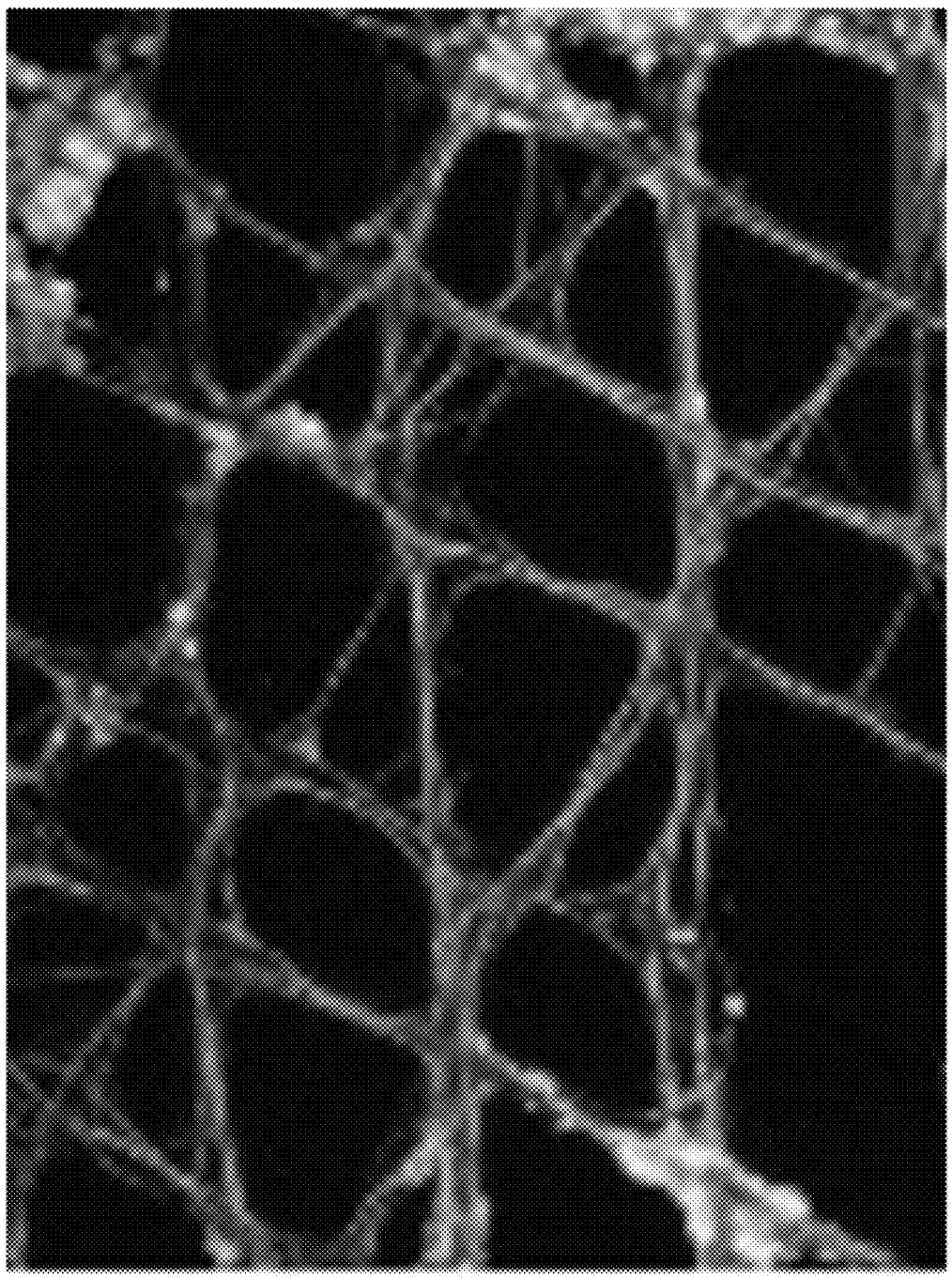
FIG. 15B9
HYBRID w/ES

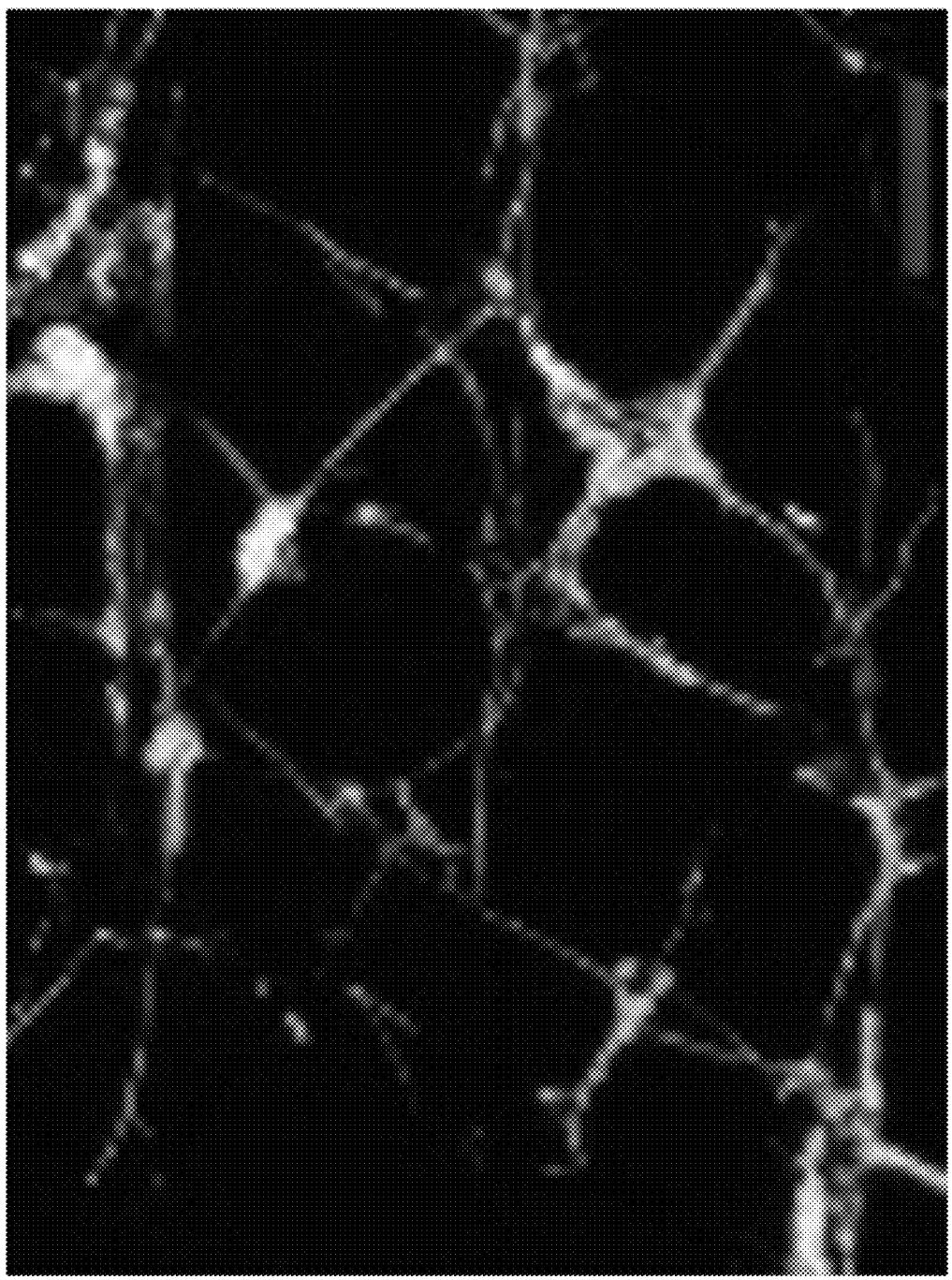
FIG. 15B10
HYBRID w/o ES

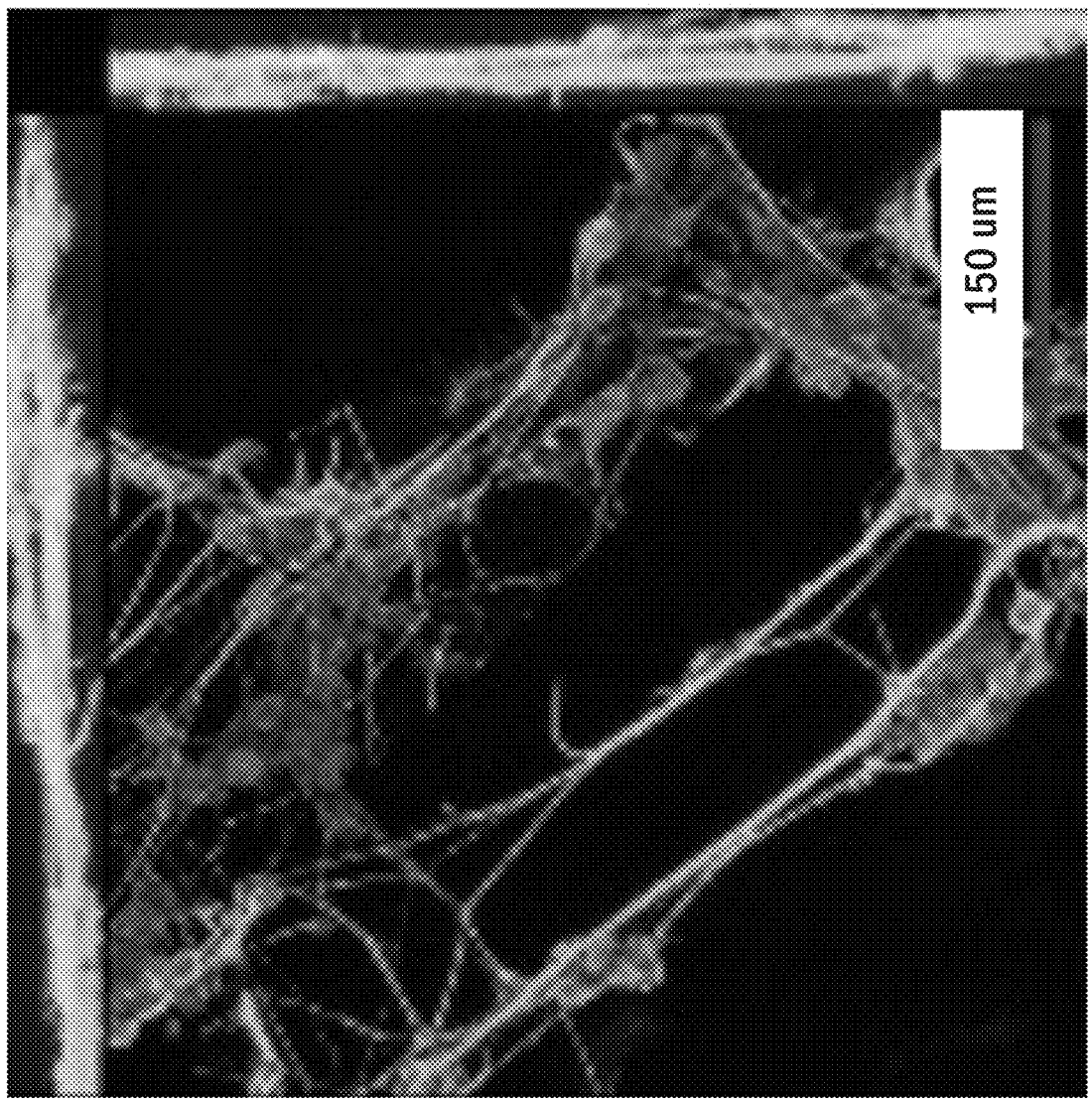
FIG. 15C1

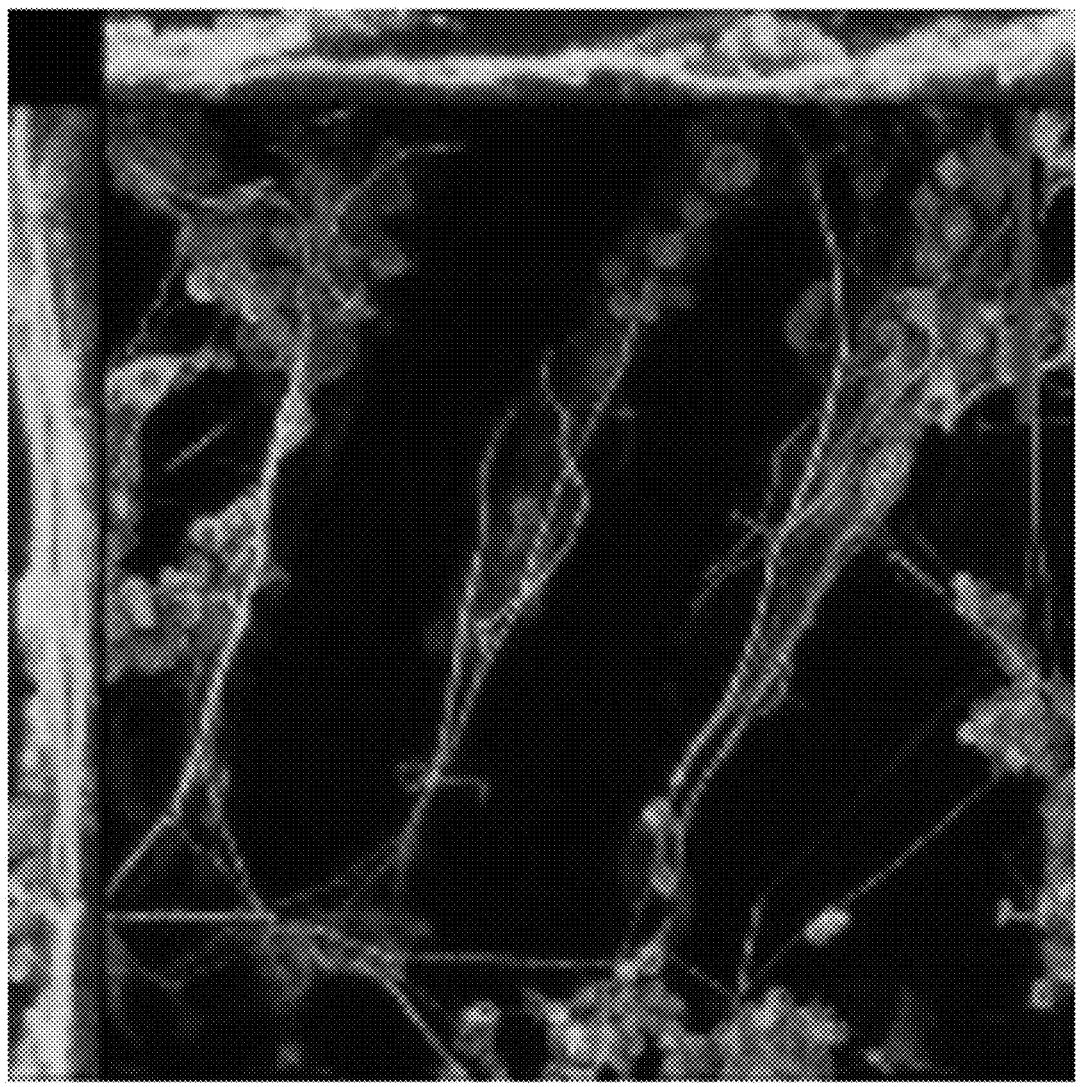
FIG. 15C2

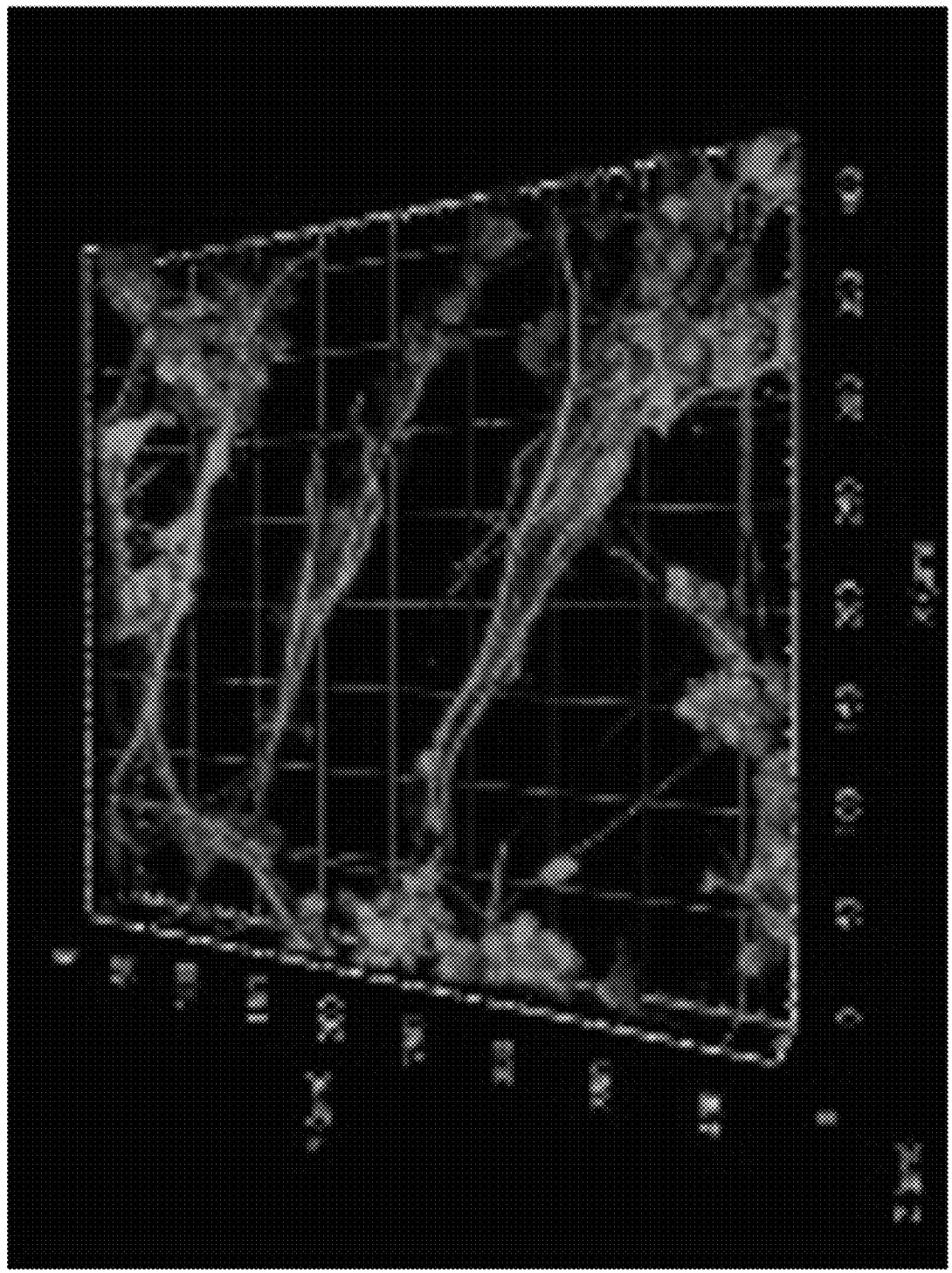
FIG. 15C3

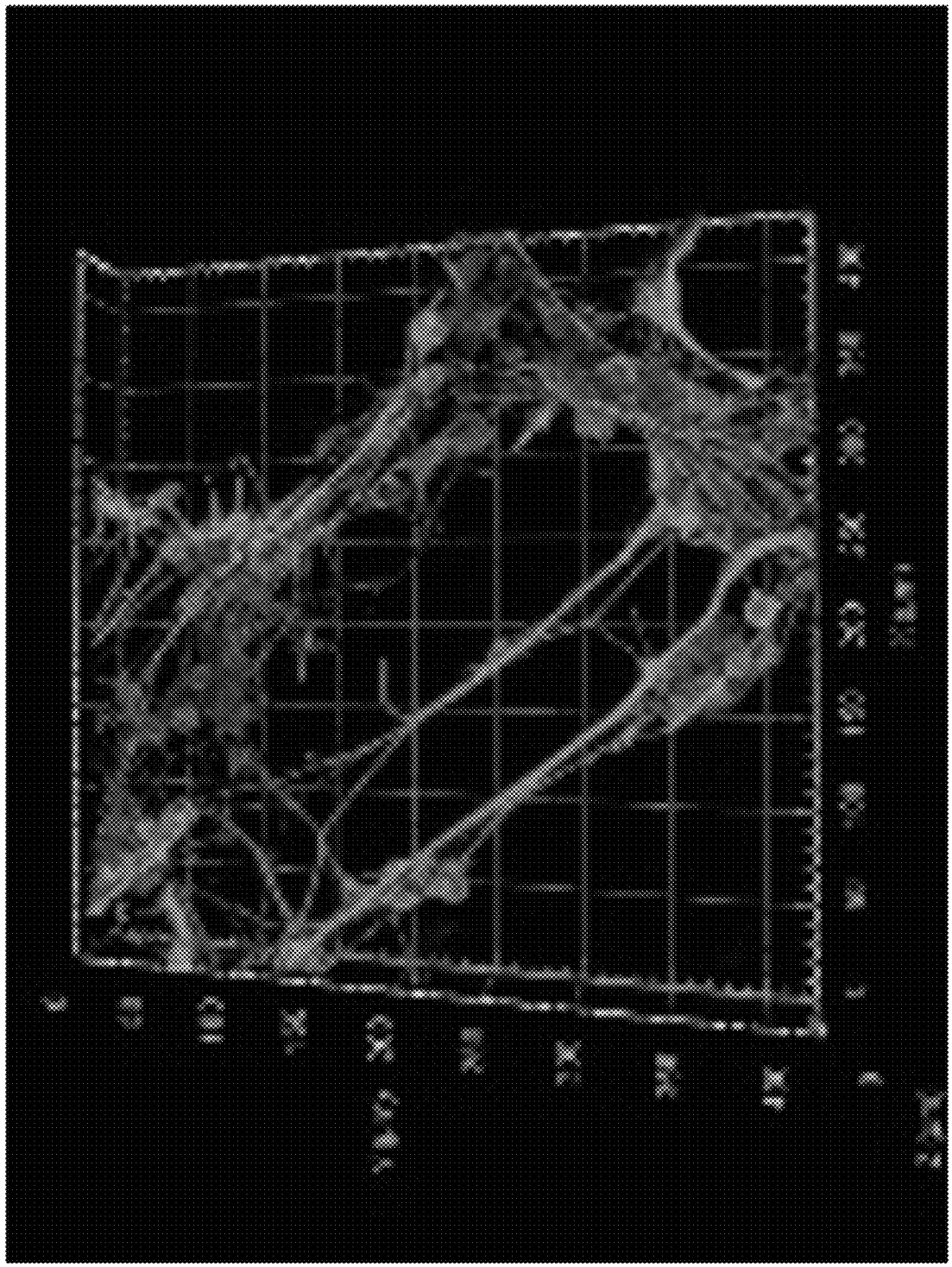
FIG. 15C4

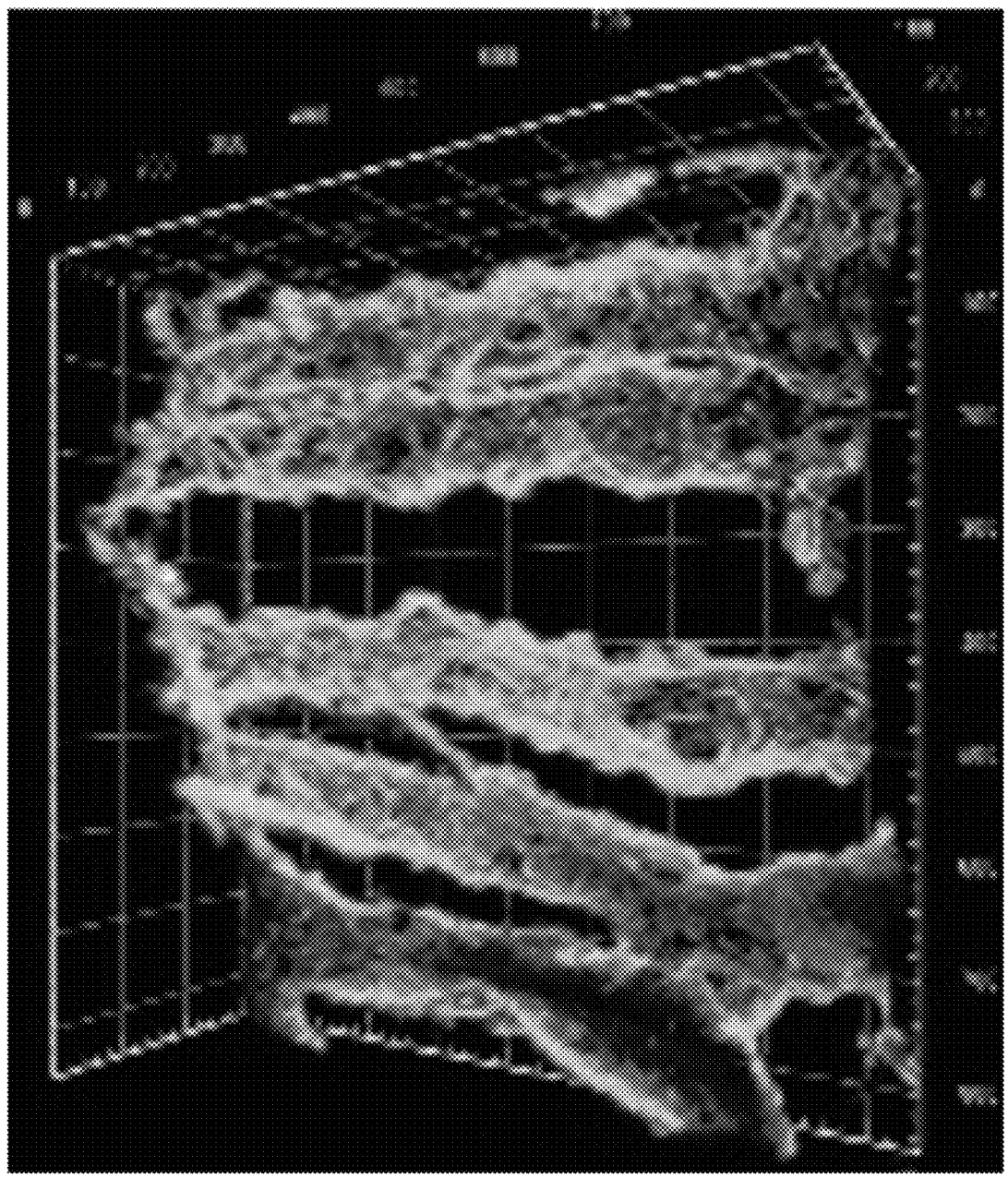
FIG. 15D1

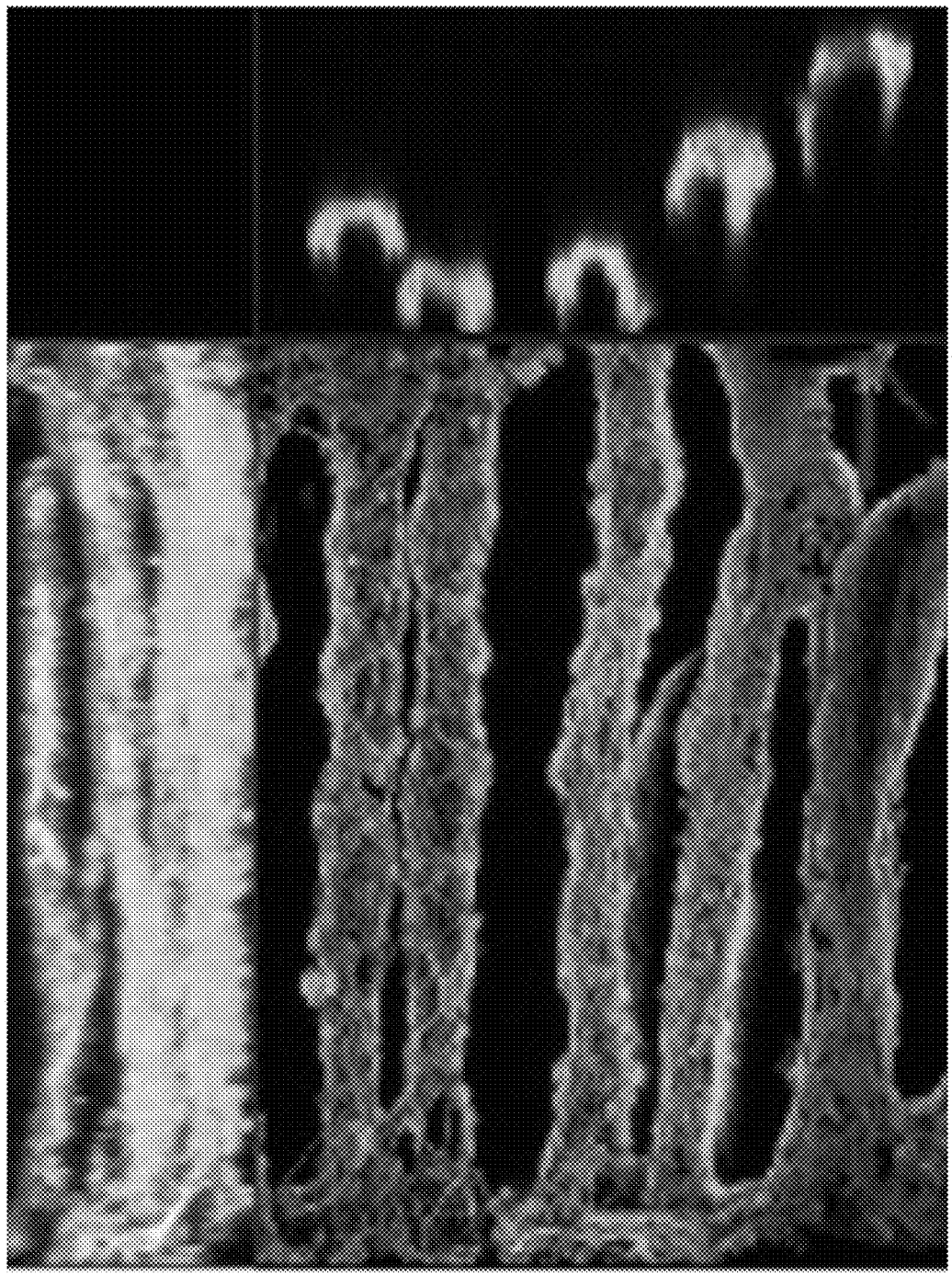
FIG. 15D2

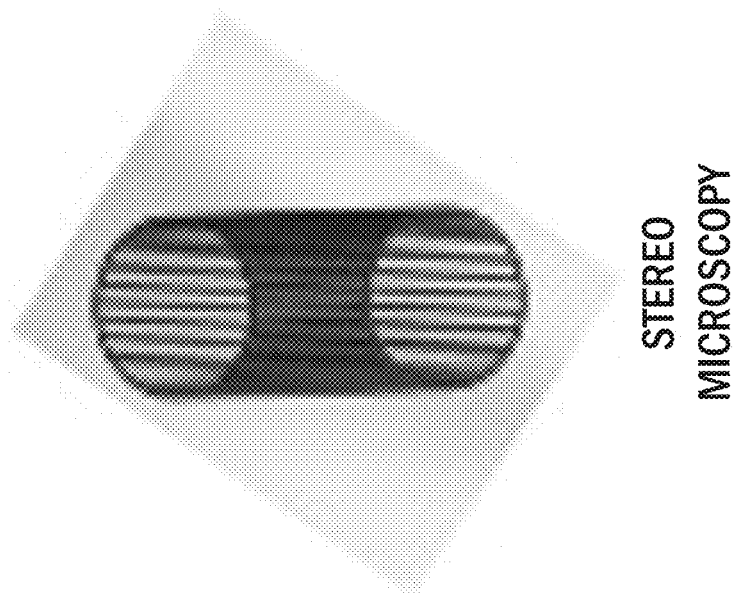
FIG. 15D3 STEREO MICROSCOPY

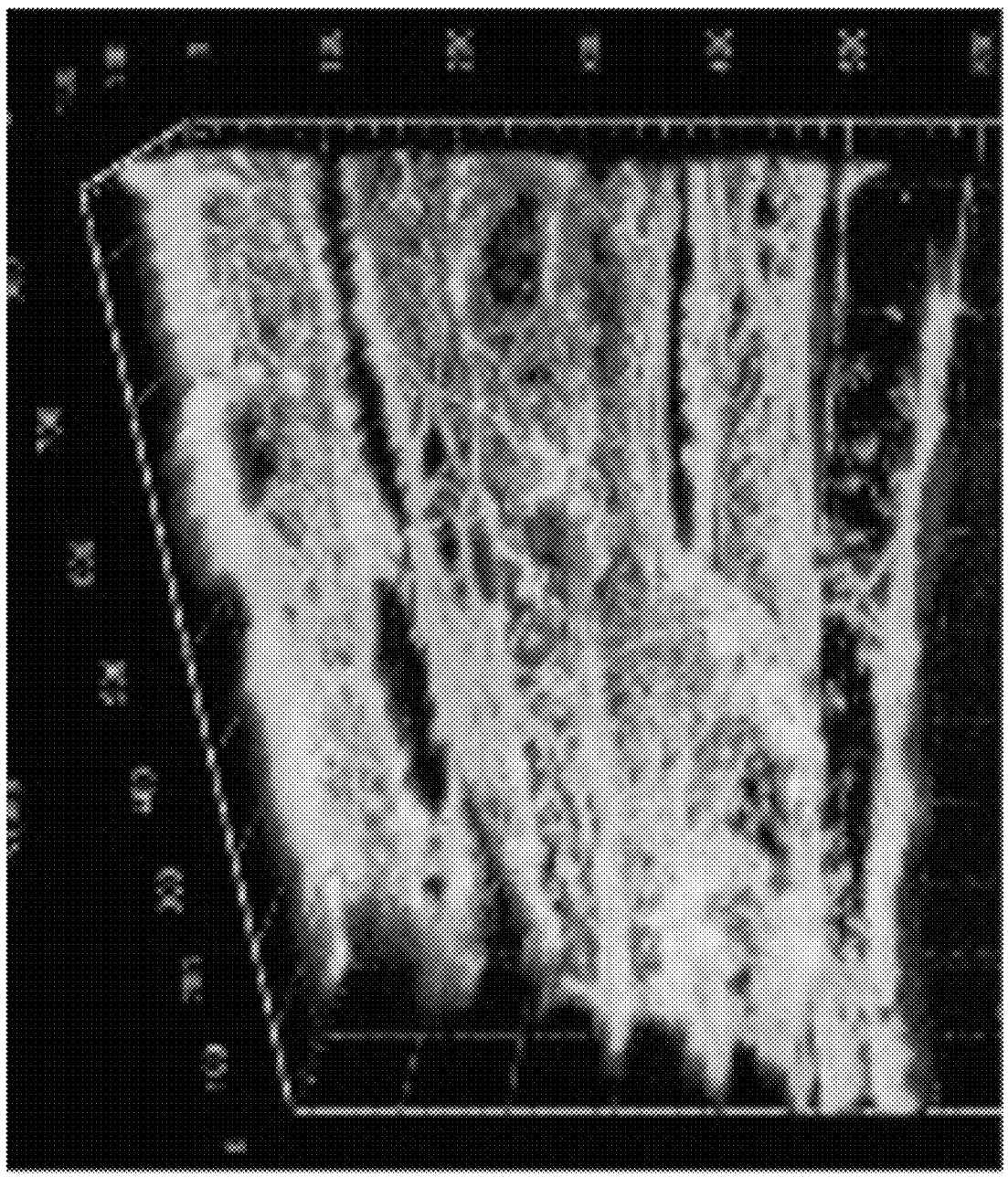
FIG. 15D4

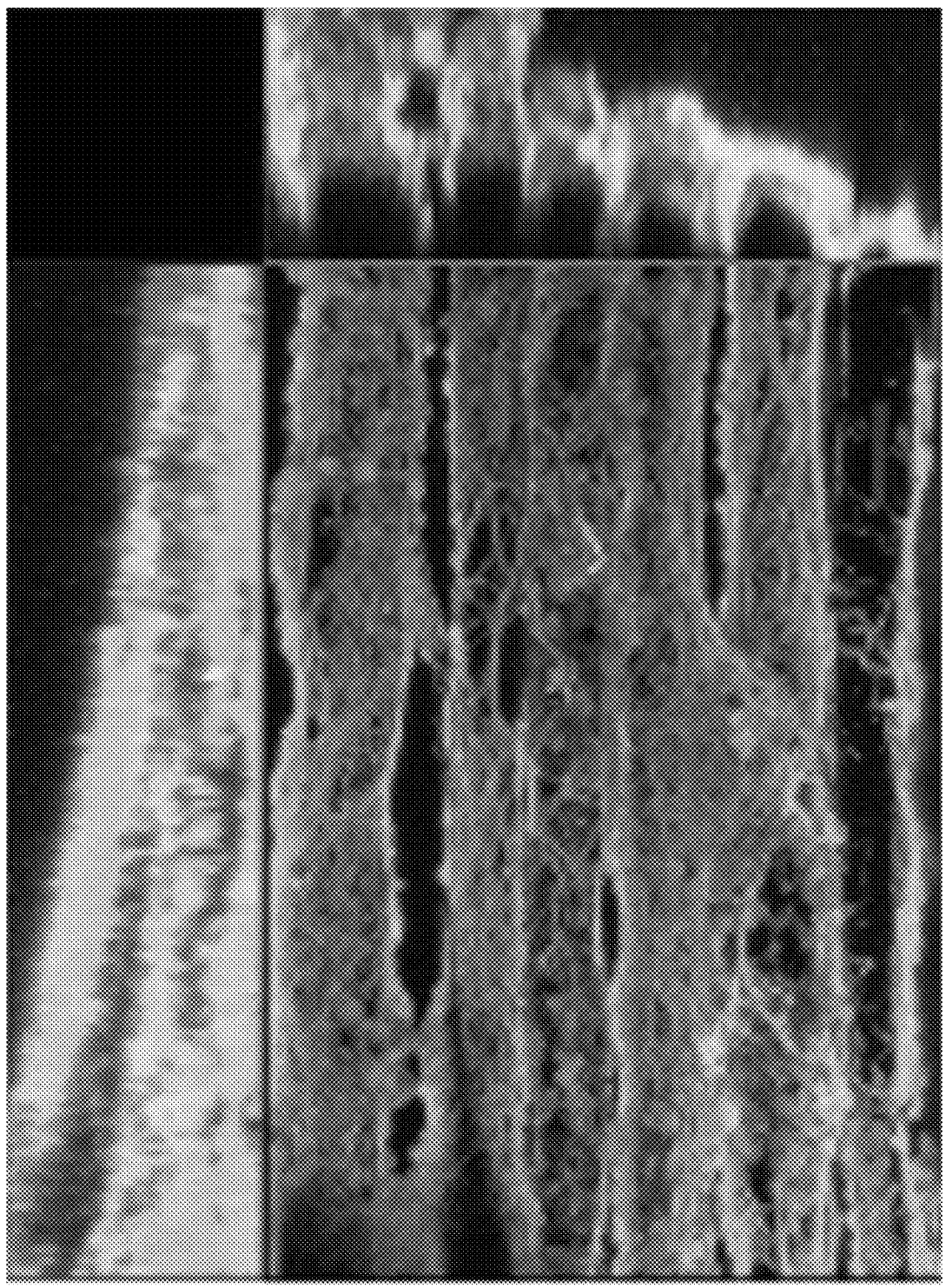
FIG. 15D5

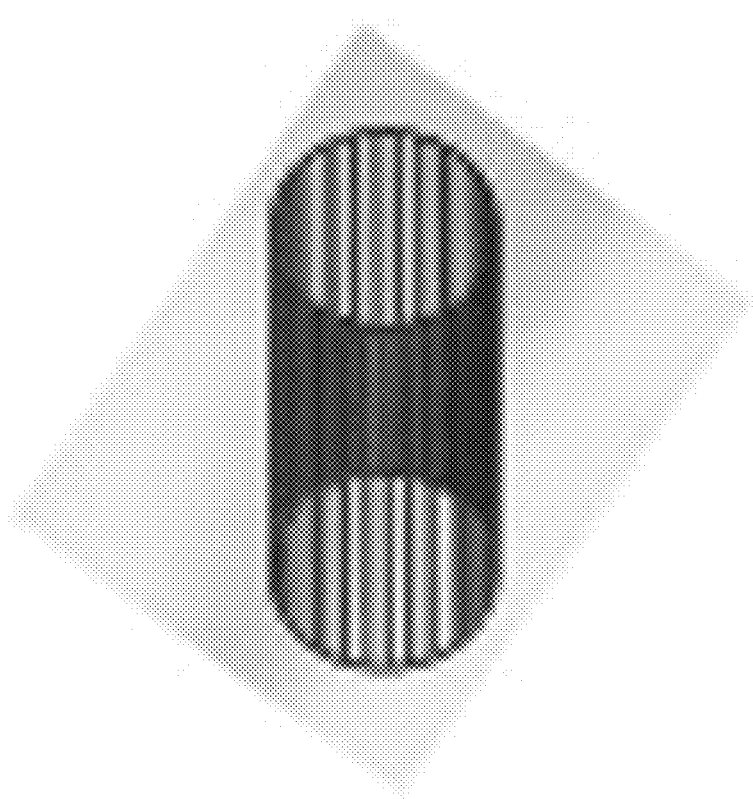
FIG. 15D6

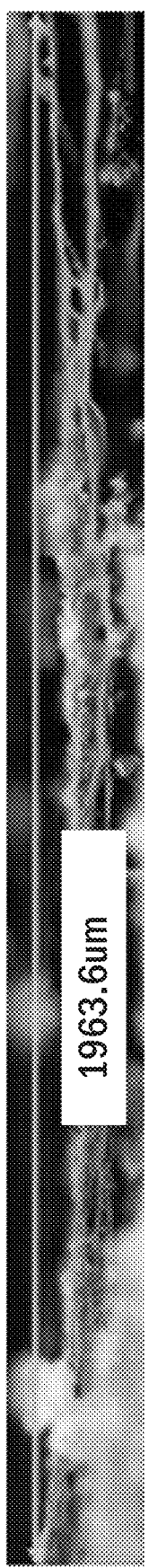
FIG. 15D7
STEREO MICROSCOPY
1963.6um

CONDUCTIVE SCAFFOLDS FOR GUIDED NEURAL NETWORK FORMATION

CROSS-REFERENCE TO RELATED APPLICATIONS

This application is a U.S. PCT National Phase entry under 35 U.S.C. 371 of International Patent Application No. PCT/US2021/045117 filed Aug. 6, 2021, which claims priority to U.S. Provisional Patent Application Ser. No. 63/063,158 filed Aug. 7, 2020, the entire disclosures of both of which being is-incorporated herein by reference.

STATEMENT REGARDING FEDERALLY SPONSORED RESEARCH

This invention was made with government support under Grant Number AR067859 awarded by the NIH. The government has certain rights in the invention.

FIELD OF THE INVENTION

The present invention relates generally to conductive scaffolds of micro and/or nanofibers with printed micropatterns that may be used to guide neural network formation. Efforts have been made to fabricate scaffolds that can potentially offer guidance niches to neuron cells for directing the extension of axons and dendrites to form neural networks or reinstall the desirable conduction functions of damaged nervous tissue. To facilitate the establishment of a functional neural network, applying electrical stimulation through conductive scaffolds is a viable strategy.

BACKGROUND OF THE INVENTION

Patients experiencing central nerve and/or peripheral nerve injury often face the risk of losing their functions. Peripheral nerve damage often occurs due to physical conflict, accidents or surgical intervention. The most significant clinical challenge associated with peripheral nerve damage is the "nerve gap," which cannot be repaired by direct end-to-end suturing. The use of autografts, a "gold standard" in clinical surgery, is restricted due to their limited availability, especially for large gaps, and the morbidity of donation site. Alternatively, allografts can be used; however, systemic immunosuppression and disease transmission remain high risks despite the possible withdrawal by pharmacological control.

To overcome the limitations associated with conventional strategies, efforts have been made to develop biomaterial-based nerve grafts that are expected to effectively promote nerve regeneration. Scaffold-guided regeneration of neural networks has become a promising approach to repair degenerative brain disease, spinal cord injury, and peripheral nerve disorders. Despite the demonstrated capability of bridging the distal and proximal peripheral nerves, it remains a significant challenge for current artificial nerve conduits to achieve the desired physiological functions, e.g., limited or no transmission of electrical stimuli. Thus, it is highly desirable to develop a new generation of nerve grafts that can not only facilitate the establishment of distal-proximal connections, but also can restore the proper signal-transmission functionality of healed nerves. As such, certain electrically conductive materials that can deliver electrical stimulation (ES) to neuron cells will be beneficial to modulate the cellular behaviors and consequently encourage the development of a functional connection.

Within the past decade, some conductive materials (e.g., poly(3,4-ethylene dioxythiophene) (PEDOT), polypyrrole (PPY), polyaniline (PANT), poly(p-phenylene-vinylene) (PPV) and polythiophene (PT)) have exhibited certain electrical properties and attracted special attention in the field of tissue engineering applications. However, factors such as poor processability and biocompatibility, limited electrical conductivity and uncontrollable mechanical properties of these conductive materials currently limit their efficacy in tissue engineering and regenerative medicine applications.

Graphene, a novel carbon nanomaterial, has drawn great attention in recent years, owing to its fascinating 2D honeycomb nanostructure and exceptional physicochemical properties, including large surface area, superior mechanical properties, excellent electrical and thermal conductivity, and unparalleled topographical features. In recognition, intensive research has been done on graphene as a potential material for regenerative medicine and tissue engineering. Early studies have demonstrated its superior cytocompatibility for cell culture. In addition, numerous studies have shown that graphene can promote the adhesion, growth, proliferation, and differentiation of various cells, including neural stem cells, embryonic stem cells, pluripotent stem cells, and mesenchymal stem cells. Moreover, studies have also revealed that high electrical conductivity of graphene could modulate neural cell mobility and differentiation under an electric field. Thus, cumulative evidence has suggested the strong potential of graphene as a novel carbon nanomaterial for nerve tissue engineering. Despite the recognized potential of graphene-based scaffolds for neural regeneration, the poor dispersibility of pure graphene in solvents makes the processing of graphene into tissue engineering scaffolds very difficult via conventional fabrication technologies.

SUMMARY

The present invention relates to the development of unique conductive scaffolds for guided neural network formation under electrical stimulation and enables the formation of 3D neural networks similar to native tissue networks.

Graphene itself is insoluble and has poor dispersion capacity, thus it is difficult to handle for further processing to fabricate conductive scaffolds. On the other hand, graphene oxide is soluble in water and can be easily processed. In addition, nerve cells are sensitive to electrical stimulation. Thus, this invention of fabricating conductive scaffolds will not only provide nerve cells with the platform to attach, migrate, and proliferate, but also controllably guide their development into the neural network under the topological and electrical stimulation.

With the methods of the present invention, the fabricated conductive scaffolds made from the reduction of graphene-oxide (GO) exhibit high conductivity and flexibility for any arbitrary configurations. The scaffolds of the present invention also require minimal graphene oxide for fabrication and are suited to mass production, with potential for automation. Furthermore, controllable degradation can be varied depending on the substrate scaffold, and the inventive scaffolds generally have good handling capacity (i.e., flexible and stretchable). The approach of the present invention enables creation of a hierarchical neural network structure with biological functions. Applications of such patterned conductive scaffolds include, but are not limited to, use as engineered conduits for guiding the differentiation and outgrowth of neural cells in peripheral nerve damage or in large-volume spinal cord injury in conjunction with electrical stimulation.

Current extracellular matrix (ECM)-like analogs involved in tissue engineering often miss the unique temporal and spatial complexity of physicochemical and electrical niches compared to their natural counterparts, which deliver regulatory instruction to cells for differentiation and tissue morphogenesis. The combination of ECM-like fibrous matrices with graphene-derived patterns is an innovative approach to effectively modulate cell behavior due to its high conductivity and biocompatibility. Direct deposition of GO onto elastic nanofiber matrices via inkjet printing forms a bio-circuit. In contrast to extensive efforts in promoting neural cell differentiation and neurite growth using graphene, the current invention (i.e., coating on the substrate surface) effectively overcomes the limitation of poor dispersibility of pure graphene on fabricated scaffolds, which exhibit no or very poor conductivity, while reducing the use of graphene. 3D printing and near-field electrostatic printing (NFEP) enable fabrication of 3D conductive scaffolds.

3D printing, especially NFEP, enables the fabrication of 3D constructs with high resolution, controllability, and reproducibility. Different from traditional 3D printing techniques, which have limited control over the architecture refinement, typically at the millimeter scale, and are applicable to those meltable or sinterable materials, but not those temperature-deactivate biological materials, NFEP can endow the printed constructs with improved resolution and better controlled 3D architecture out of diverse materials including biological materials. Coating of graphene oxide or reduced graphene oxide (rGO) onto such scaffold surface yields the generation of 3D conductive scaffolds with well-controlled hierarchical structures for guided 3D nerve network development under electrical stimulation, which has not been achieved with existing scaffolds.

Further advantages to the inventive approach of fabricating conductive scaffolds include simple setup for easy scaleup, broad applicability for any arbitrary substrates (e.g., foam, fiber, sphere, membrane, hydrogel, 3D printed construct, etc.), high controllability of reduced graphene oxide thickness, and reliability of the conductivity GO coating or deposition in accordance with the present invention offers a convenient approach for handling graphene-derived materials to functionalize scaffolds. After reduction, the rGO perfectly inherits the electrical conductivity of graphene. Procedures in accordance with embodiments of the present invention enable the scaffolds to provide electrical conductivity and the favorable chemical environment needed by nerve cells. Moreover, an electrically conductive scaffold that can deliver electrical stimulation to neurons/nerve cells are capable of modulating the cellular behaviors for desirable neural functions.

With the aid of an inkjet printer, arbitrary conductive patterns of rGO with a high resolution and high reproducibility can be developed on any fibrous matrices while providing the biomimetic substrate for tissue growth. Such conductive matrices may see versatile applications in regenerative medicine, aiming to promote cell-fiber interactions for the regulation of cell phenotype, direct tissue regeneration via contact guidance, support stem-cell proliferation and differentiation on the matrix surface, and allow the formation of 3D tissues with cells embedded among the fibers.

The utility of substrates fabricated from 3D printing or NFEP, a technology combining electrostatic spinning and 3D printing, benefits from high reproducibility to enable development of customized, complex, conductive 3D geometries with well-controlled micro and macrostructures, which can not only fit to the defect size but also have good control over the 3D network architecture of neural networks.

Furthermore, the present invention addresses the challenges associated with the fabrication of conductive scaffolds from graphene and/or its derivatives, while offering improved fidelity and cost-effectiveness. The fabrication process can be automated easily for scale-up and mass production. For instance, the coating process can be carried out by a robotic arm with programmed procedures.

In conjunction with inkjet printing and NFEP, it becomes possible to generate conductive scaffolds with the capability of guiding neural network formation on biomimetic substrates or in 3D constructs under electrical stimulation. Meanwhile, the method of the present invention also has a high degree of freedom, a relatively low barrier for processing, and strong error-tolerance during manufacturing.

The scaffolds of the present invention can serve as engineered conduits for guiding the differentiation and outgrowth of neural cells for treatment of peripheral nerve damage or large-volume spinal cord injury under the electrical stimulation. The scaffolds could also locally deliver various biomolecules in conjunction with electrical stimulation for facilitated nervous system regeneration. 2D conductive scaffolds/membranes can be further fabricated into a nerve conduit or nerve grafts using sheet rolling, matrix molding, and other bio-manufacturing approaches and used for facilitated nerve regeneration under electrical stimulation. 3D microfiber conductive scaffolds (e.g., those derived from near-field electrostatic printing) can be utilized for advanced nerve repair via capture of anatomical accuracy and complex geometries, as well as through programmable incorporation of biomimetic physical and biochemical functionalities in conjunction with electrical stimulation. With the aid of advanced, patient-specific scanning technology (e.g., magnetic resonance imaging and computed tomography), this approach has the potential to produce customized biomedical devices that possess the geometries to match inherent tissue anatomies. Besides nervous repair, the conductive scaffolds made in accordance with embodiments of the present invention may also see potential applications in bone, chronic wound, muscle, cardiac and vascular repair, as 2D matrices or 3D constructs.

Additionally, the high elasticity and strong mechanical properties of some substrate materials, such as poly(L-Lactide-co-s-Caprolactone) (PLCL) fibrous structures, may offer the ability to be used as wearable bio-conductive devices or biosensors.

In an embodiment of the present invention an electrically-conductive scaffold can be fabricated that includes a biomimetic matrix, and an electrically-conductive pattern of reduced graphene oxide on the biomimetic matrix. Such an electrically-conductive scaffold can be made by obtaining a biomimetic matrix and then providing the biomimetic matrix with an electrically-conductive pattern of reduced graphene oxide.

BRIEF DESCRIPTION OF FIGURES

For a more complete understanding of the present disclosure, reference is made to the following drawings, in which:

FIG. 6A is a collection of stereomicroscopic images of graphene oxide printed stripes with different widths, before reduction;

FIG. 6B is a collection of stereomicroscopic and SEM images of graphene oxide-printed stripes with different widths, after reduction;

FIG. 6C is a collection of stereomicroscopic images of graphene oxide-printed patterns, before reduction;

FIG. 6D is a collection of stereomicroscopic images of graphene oxide-printed patterns, after reduction;

FIG. 8B shows the recovery testing results for the substrate materials of FIG. 8A;

FIGS. 9D-9G are a series of epifluorescent images of PC12 cells cultured on nanofiber matrices with and without electrical stimulation after culturing for 7 and 14 days, under the conditions represented in FIG. 9A;

FIGS. 9H-9K are a series of epifluorescent images of PC12 cells seeded on inkjet-printed stripes on nanofiber matrices after 14 days of culturing under different electrical stimulation conditions;

FIGS. 9L-9O are a series of epifluorescent images of PC12 cells seeded on the inkjet-printed circle patterns on nanofiber matrices after 14 days of culturing under different electrical stimulation conditions;

FIG. 14K is a corresponding intensity plot of the images of FIGS. 14A-14J; and

FIGS. 15A-1 to 15A-6, FIGS. 15B-1 to 15B-10, FIGS. 15C-1 to 15C-4, and a fourth group that includes FIGS. 6D-1, 6D-2, 6D-4, 6D-5 and 6D-7, are each a series of immunostaining images for neurites after 21 days culturing of PC12 cells seeded onto graphene oxide/reduced graphene oxide coated PLCL microfibers with various patterns, in accordance with embodiments of the present invention, FIG. 15D-3 being a cylindrical construct corresponding to FIGS. 6D-1 and 6D-2, and FIG. 15D-6 being a cylindrical construct corresponding to FIGS. 6D-4, 6D-5, and 6D-7.

DETAILED DESCRIPTION OF EXEMPLARY EMBODIMENTS

Figure 1:
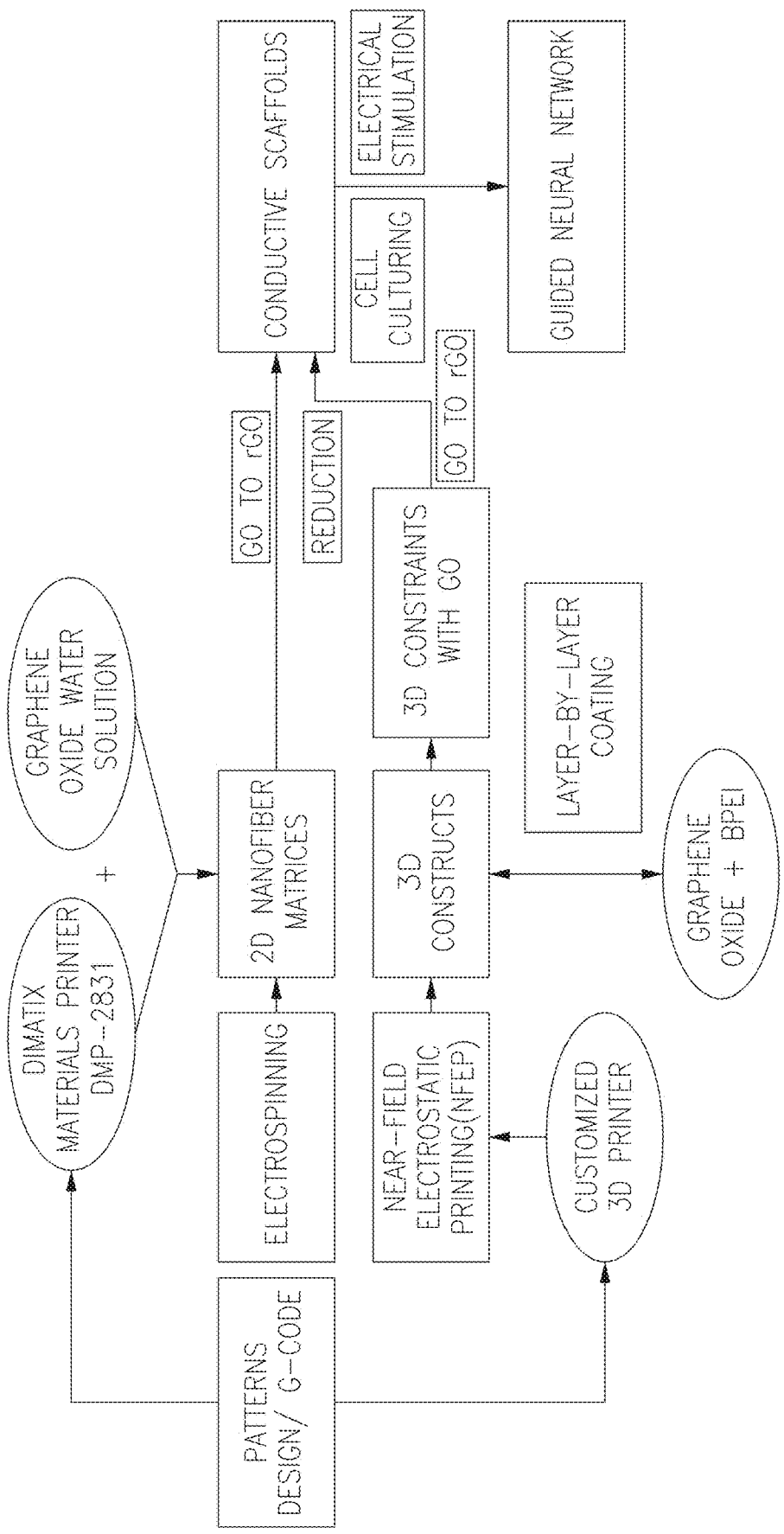
FIG. 1 is a schematic diagram of an exemplary system for making scaffolds in accordance with an embodiment of the present invention.

Reference will now be made to several embodiments of the present invention(s), examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

All terms defined herein should be afforded their broadest possible interpretation, including any implied meanings as dictated by a reading of the specification as well as any words that a person having skill in the art and/or a dictionary, treatise, or similar authority would assign thereto. The terms, "for example", "e.g.", "optionally", as used herein, are intended to be used to introduce non-limiting examples. The phrases "in one embodiment" and "in some embodiments" as used herein do not necessarily refer to the same embodiment(s), though they may. Furthermore, the phrases "in another embodiment" and "in some other embodiments" as used herein do not necessarily refer to a different embodiment, although they may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on." In addition, the terms "comprises" and "comprising" when used herein specify that certain features are present in that embodiment; however, this phrase should not be interpreted to preclude the presence or addition of additional steps, operations, features, components, and/or groups thereof.

Conductive scaffolds in accordance with the present invention may fabricated by depositing soluble graphene oxide on substrate surfaces, as well as by coating onto the 3D microfiber scaffolds layer-by-layer and then reducing into conductive reduced graphene oxide. With highly controllable deposition or coating to any arbitrary surface, the conductive scaffolds of the present invention can achieve various configurations, with potential for mass production.

In general, to obtain conductive scaffolds, a substrate made from synthetic materials such as PLCL, natural materials such as collagen, or hybrid materials such as PLCL/collagen is desirable, as the scaffold will need to take forms such as sponges, fibers, meshes, membranes, spheres, etc. On top of such a substrate, graphene oxide (GO) will be deposited from an aqueous solution in a layer-by-layer manner by alternating it with cationic polyelectrolyte, such as branched polyethylenimine (BPEI), in order to achieve different thicknesses and strong bonding. Upon reaching the desired thickness, the substrate with deposited GO will be reduced to reduced graphene oxide (rGO) with reductants such as ascorbic acid. Upon completion of the reduction, the scaffolds will be conductive for use in electrical stimulation.

Unique conductive features of the scaffolds can be afforded depending on the manufacturing technique. For example, applied inkjet printing can be used to achieve 2D spatial conductive patterns on biomimetic fibrous matrices. Specifically, a synthetic polymer of PLCL, which has demonstrated potential utility in nerve tissue engineering, may be electrospun into nonwoven nanofiber matrices to mimic the native tissue extracellular matrix (ECM). Then GO solution can be loaded into a printer cartridge as "ink" and be printed onto the fibrous matrices, which essentially serve as "paper." During printing, the GO solution is precisely deposited onto the matrix surface to generate a continuous layer of a GO pattern following a pre-designed pattern. After reducing the printed GO, a pattern of rGO can be formed on the fiber matrix. The obtained conductive patterns exhibited ability to promote the neurite ingrowth along the rGO printed area under electrical stimulation.

In another embodiment, 3D conductive scaffolds can be deposited on printed microfiber structures using near-field electrostatic printing (NFEP). An appropriate material is printed into different microfiber templates using NFEP. Various microfiber patterns may be designed accordingly, including those with different fiber overlay angles (45°, 60°, 75°, 90°), different fiber diameters (e.g., ranging from 15 μm to 150 μm) and complex structures (e.g., "spider web" or "cylinder" structures). Once the microfiber structure is fabricated, GO solution may be coated onto PLCL microfibers via layer-by-layer technique and in situ reduced into rGO. The obtained conductive scaffolds showed capability of inducing the neural network formation along the conductive microfibers under electrical stimulation. Both pattern and fiber diameter could regulate neural cell differentiation and neurite outgrowth under electrical stimulation.

Figure 2:
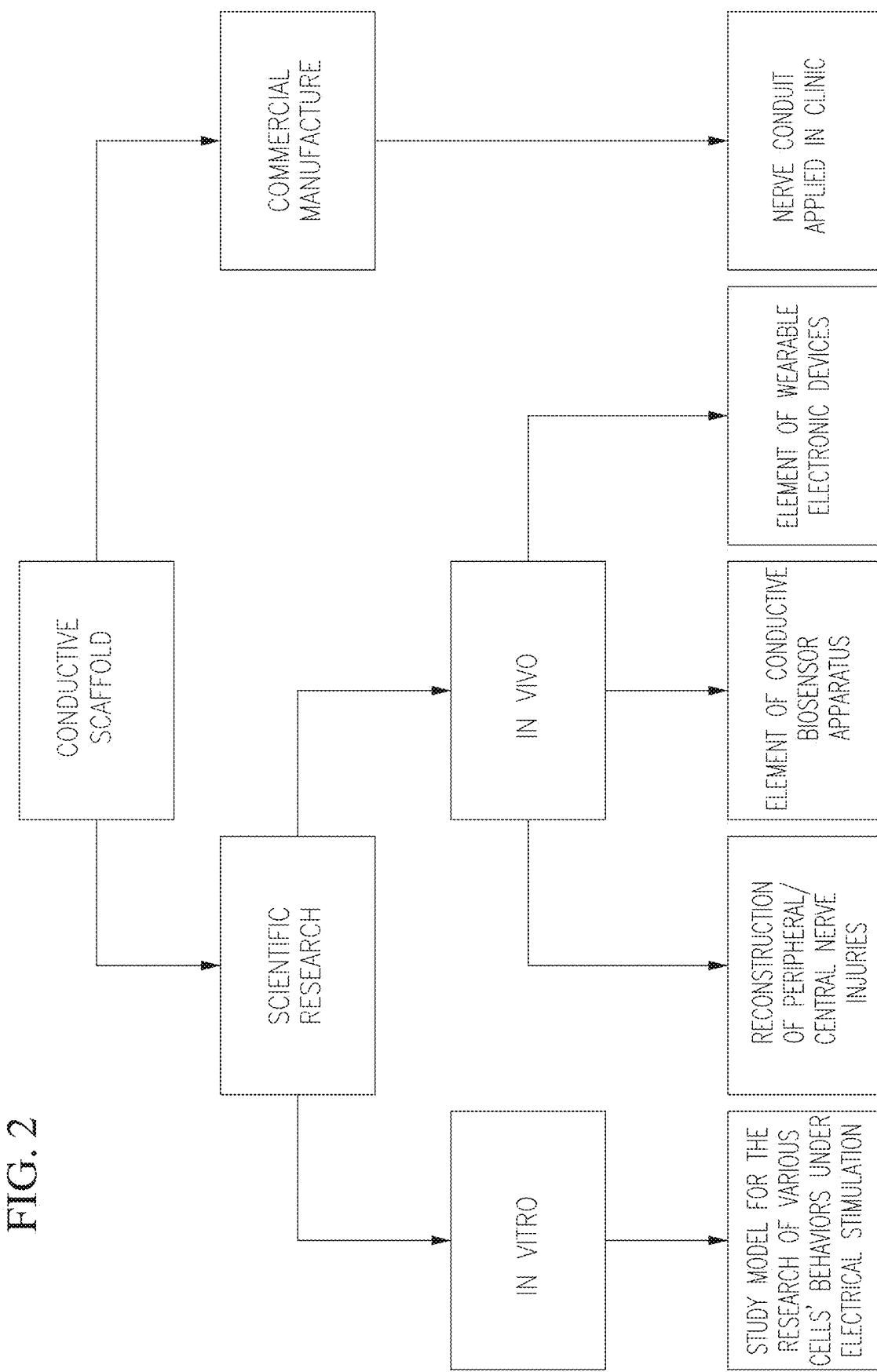
FIG. 2 is a flow diagram illustrating an exemplary method of making scaffolds in accordance with an embodiment of the present invention.

FIG. 1 illustrates schematically a system for producing scaffolds in accordance with the present invention, while FIG. 2 outlines the process for same.

Prototypes of conductive micropatterns on PLCL nanofiber matrices and conductive 3D PLCL microfiber scaffolds have been fabricated as described above. The scaffolds were then characterized by a scanning electron microscope (SEM) and optical microscope to observe the morphology and microstructure of the obtained scaffolds.

Figure 3:
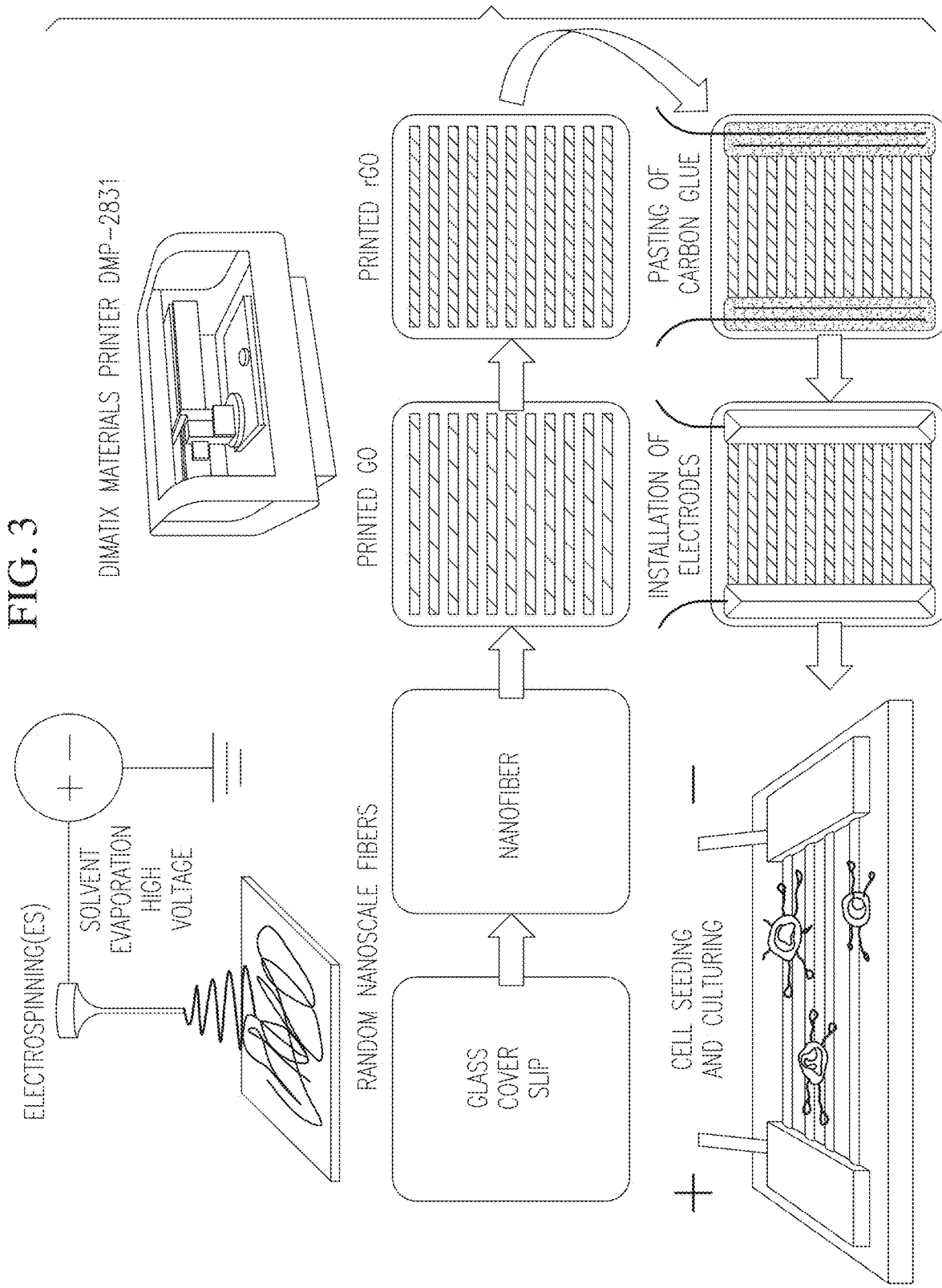
FIG. 3 is a schematic diagram of a 2D inkjet printing-based fabrication process for scaffolds with conductive micropatterns.

Prototypes of conductive micropatterns on PLCL nanofiber matrices are depicted in FIG. 3.

Figure 4:
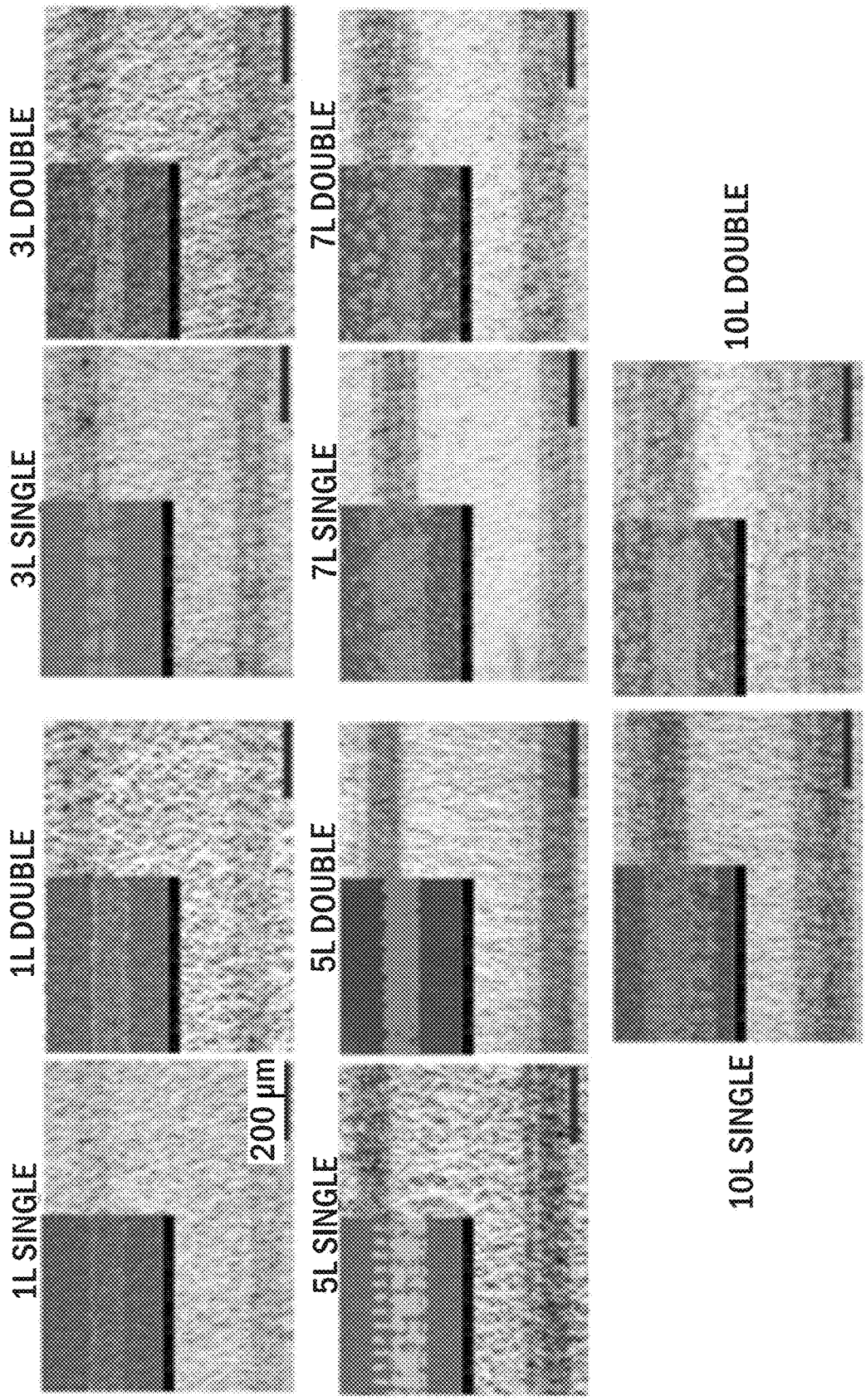
FIG. 4 is a series of stereomicroscope images and scanning Electron Microscope images of scaffolds made in accordance with embodiments of the present invention.
Figure 5:
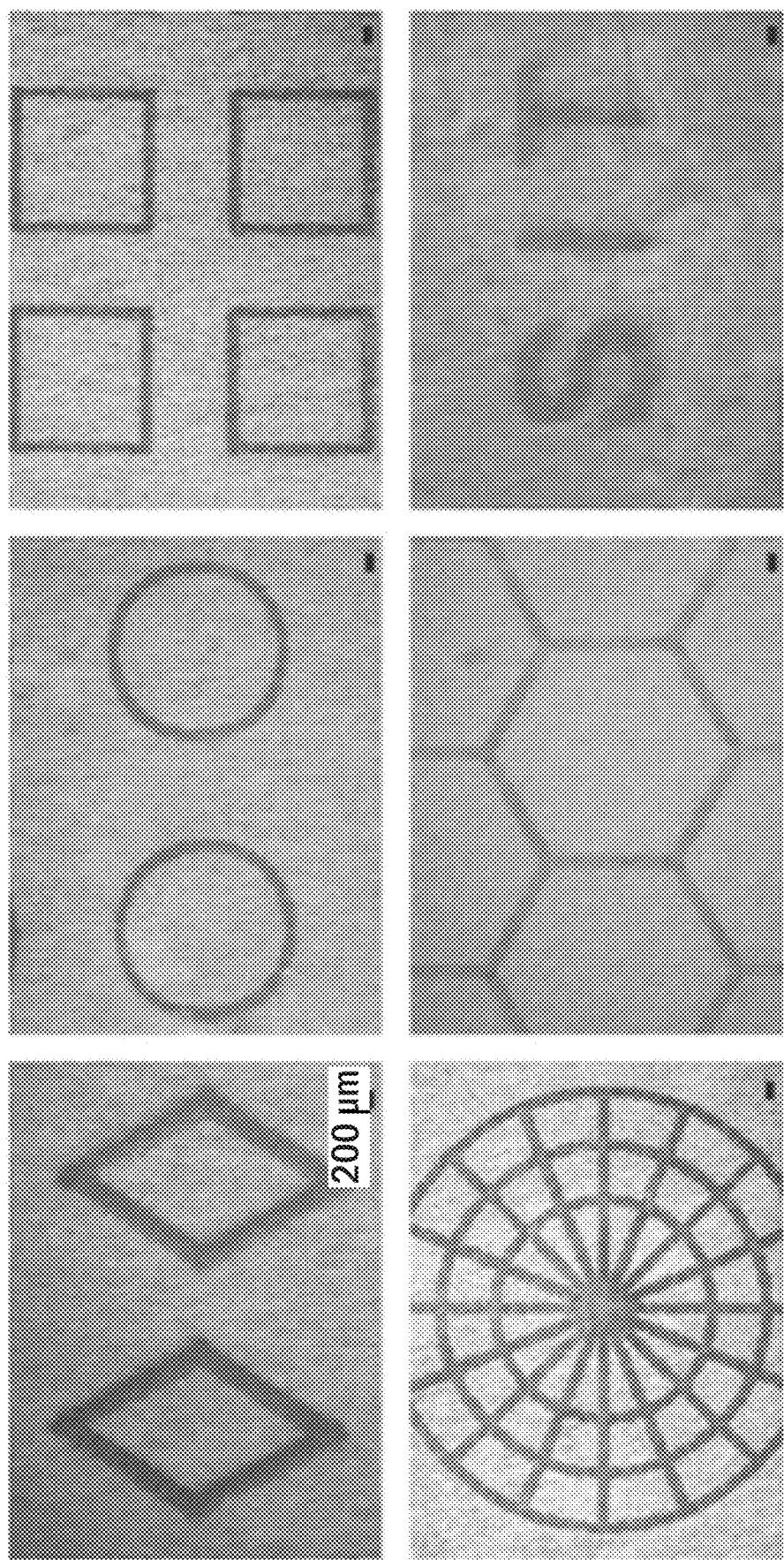
FIG. 5 is a collection of stereomicroscope images of different printing patterns on scaffolds made in accordance with embodiments of the present invention.

FIG. 4 shows stereomicroscope and SEM images of various resultant patterns, resulting from varying parameters on such scaffolds, with a scale bar of 200 μm. FIG. 5 shows further stereomicroscope images of resulting patterns, with a scale bar of 200 μm. FIG. 6 shows stereomicroscopic and SEM images of printed graphene oxide stripes of various widths, and complex shapes of patterns before and after reduction, with a scale bar of 200 μm.

Figure 10:
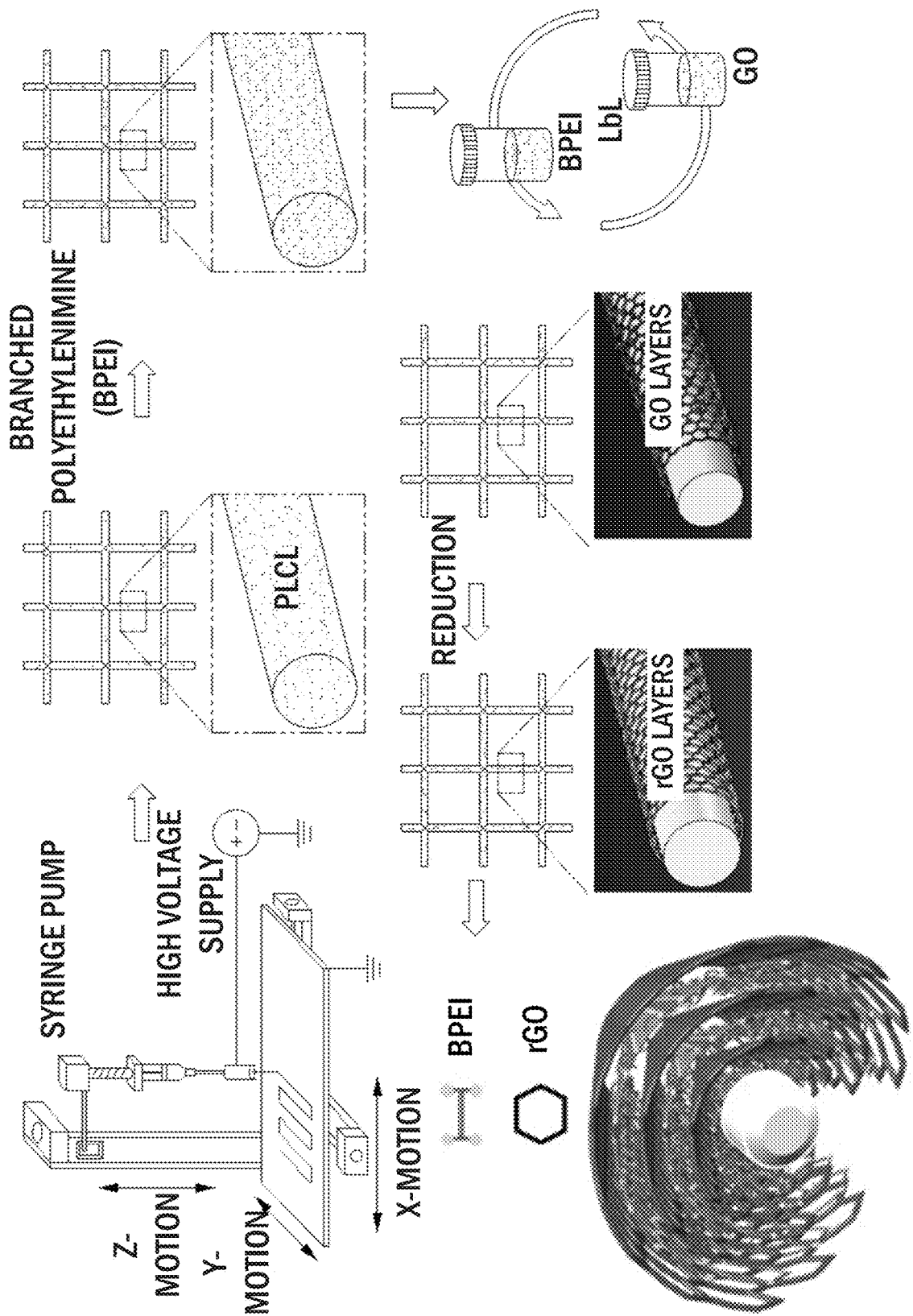
FIG. 10 is a series of schematic illustrations showing the production of 3D conductive microfiber scaffolds based on near-field electrostatic printed constructs.
Figures 11A, 11B, 11C, 11D:
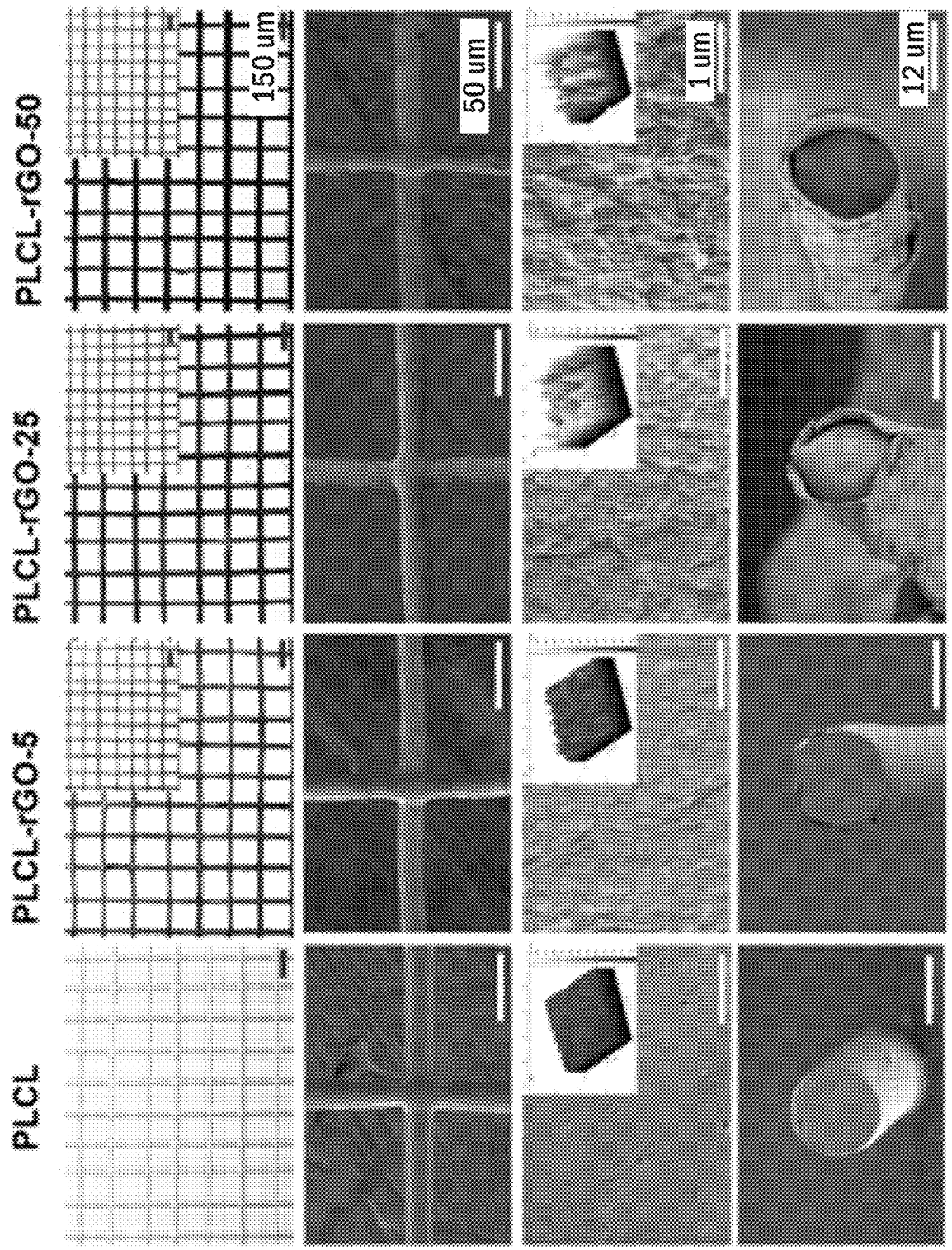
FIG. 11 is a series of images of PLCL microfibers coated with graphene oxide and those coated with reduced graphene oxide, taken with a stereomicroscope (FIG. 11A) or scanning electron microscope (FIGS. 11B-11D) with various magnifications.
Figure 12A:
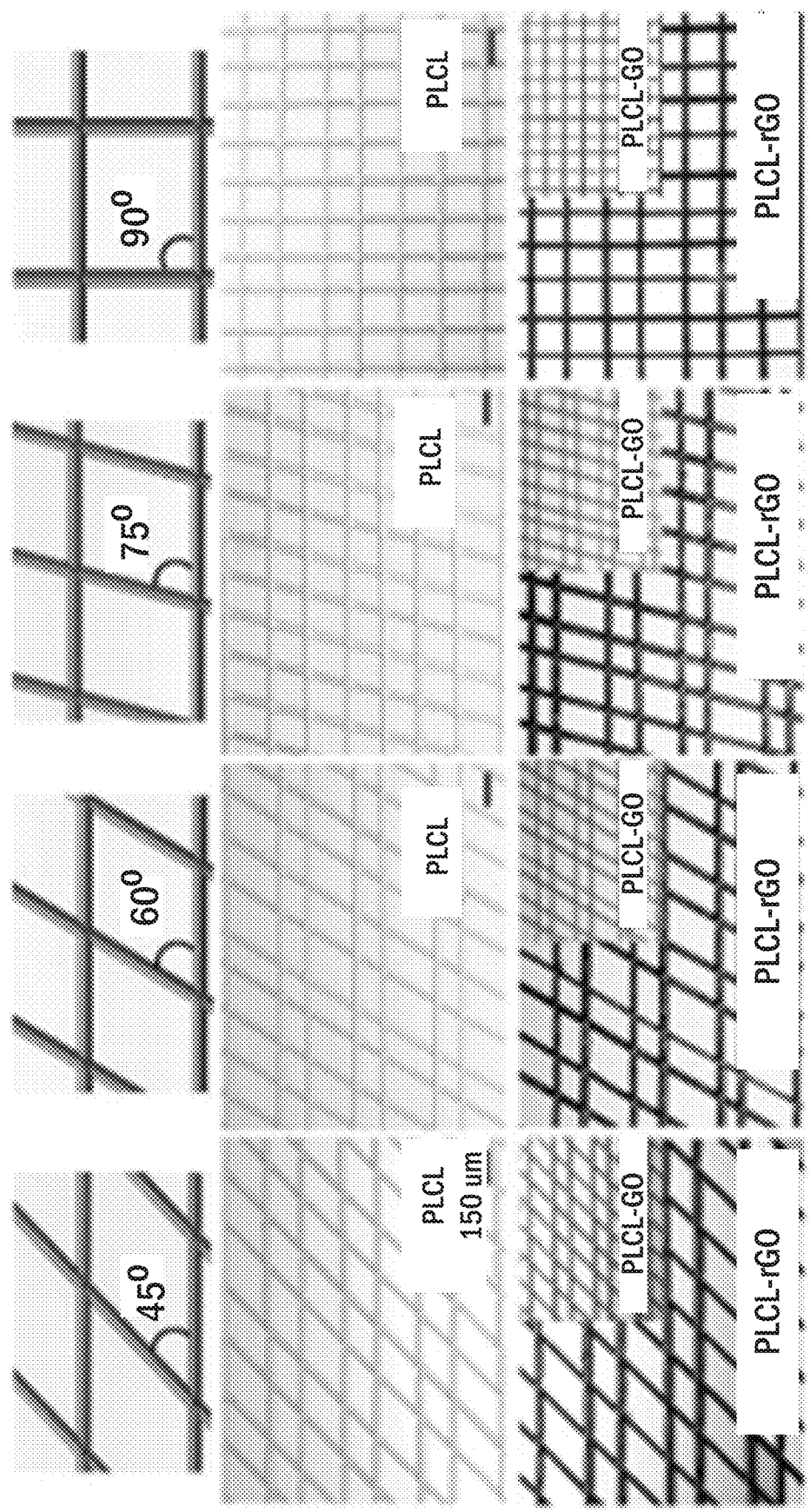
FIG. 12A is an illustration/morphology of microfibers with different angles, in accordance with an embodiment of the present invention.
Figure 12B:
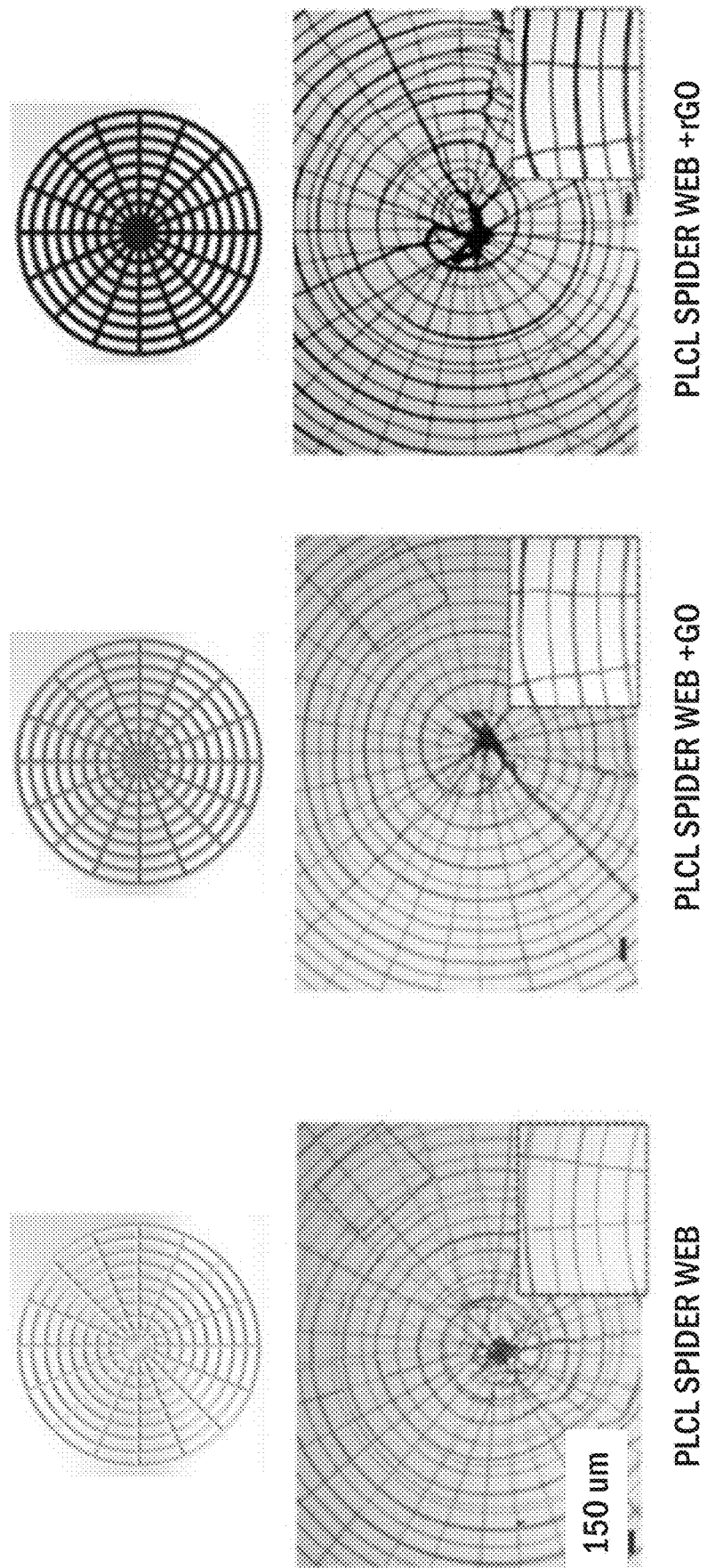
FIG. 12B is an illustration/morphology of microfibers in a spider web-like structure, in accordance with an embodiment of the present invention.
Figure 12C:
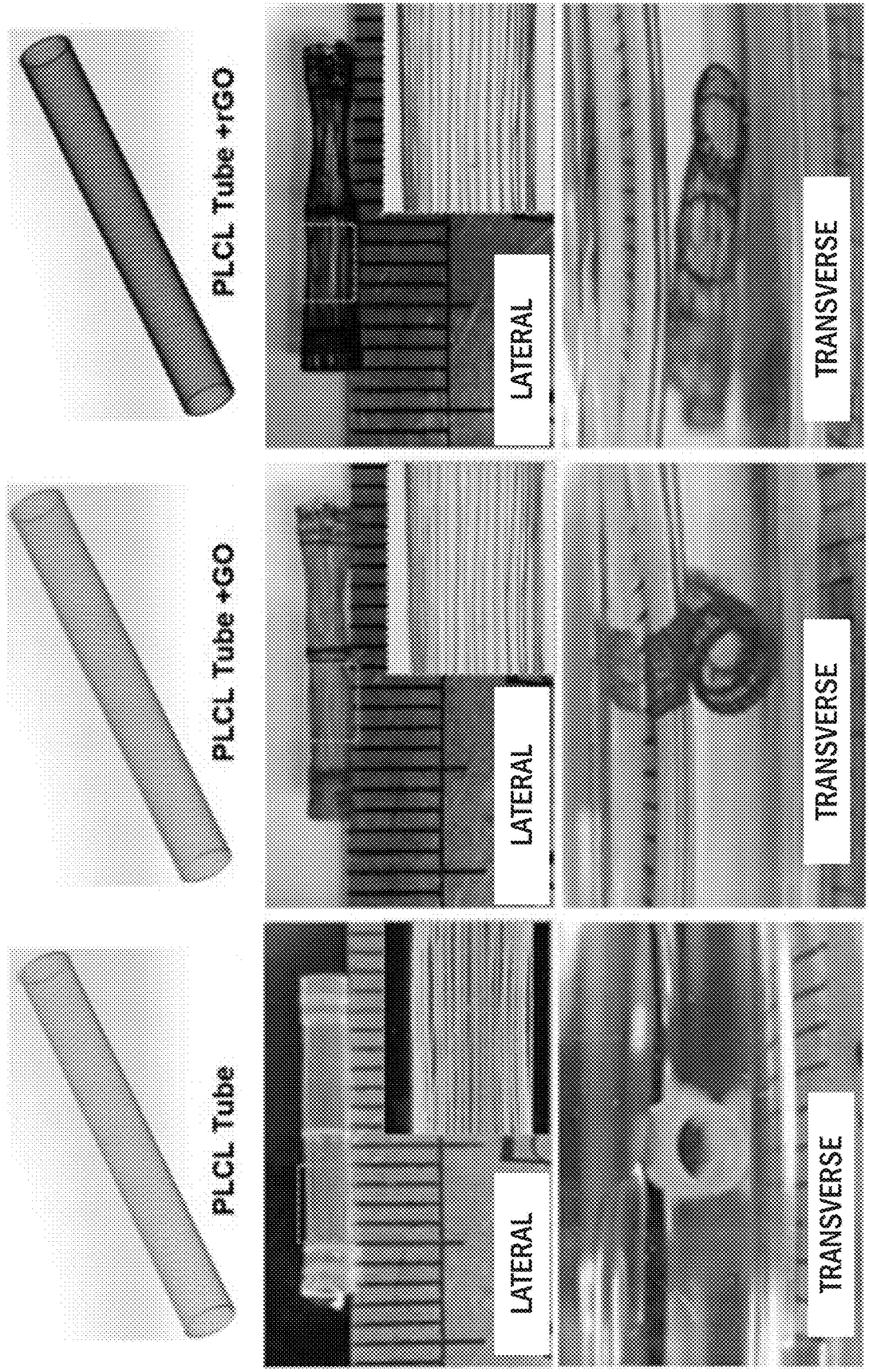
FIG. 12C is an illustration/morphology of microfibers in a large volume cylindrical construct structure, in accordance with an embodiment of the present invention.
Figure 12D:
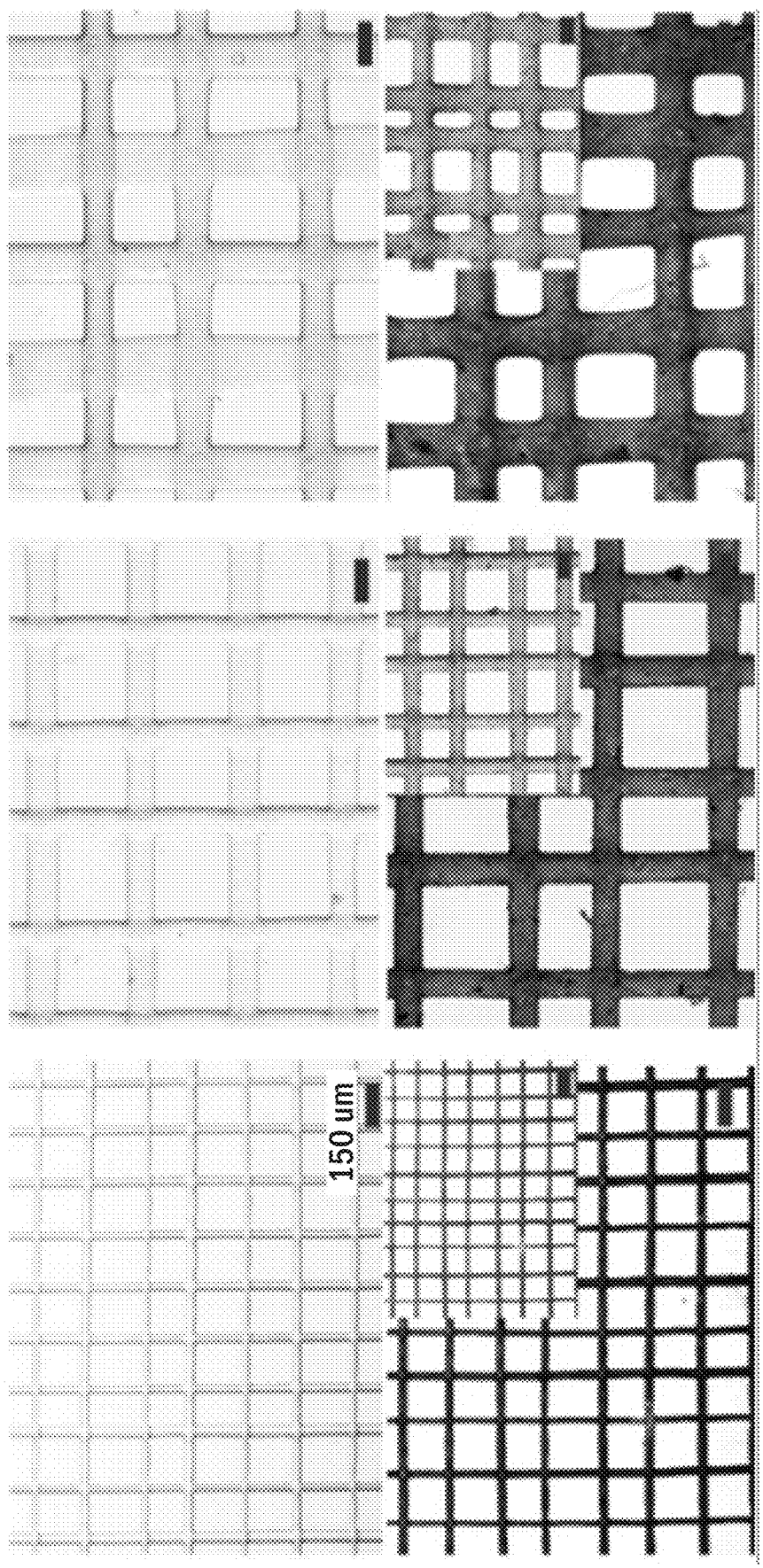
FIG. 12D is an illustration/morphology of microfibers with different diameters, in accordance with an embodiment of the present invention.

FIG. 10 illustrates schematically the production of 3D conductive microfiber scaffolds manufactured with near-field electrostatic printed constructs. FIG. 11 shows the morphology of graphene oxide/reduced graphene oxide coated PLCL microfibers with varying coating layers, via stereomicroscopy (FIG. 11A; scale bar: 150 μm) and scanning electron microscopy at various magnifications, wherein the depicted scale bars are 500 μm, 1 μm and 12 μm, respectively, for FIGS. 11B-11D.

FIG. 12 is an illustration of morphology of various printing patterns of microfibers made in accordance with an embodiment of the present invention, showing microfibers with different angles (FIG. 12A), spider web-like structures (FIG. 12B), large volume cylindrical constructs (FIG. 12C) and with different diameters (FIG. 12D), wherein all scale bars represent 150 μm.

The coating of GO/rGO layers on the surface of arbitrary substrates may yield conductive scaffolds exhibiting exceptional unique topographical features and excellent electrical conductivity. In view of dominant efforts to guide neural network formation via scaffold topography on a planar substrate such as silicon wafer, the current invention develops unique conductive scaffolds for neural network formation under electrical stimulation and enables the formation of 3D neural networks similar to the native tissue network. More specifically, hierarchical neural network structure with biological functions may be established.

Figure 7A:
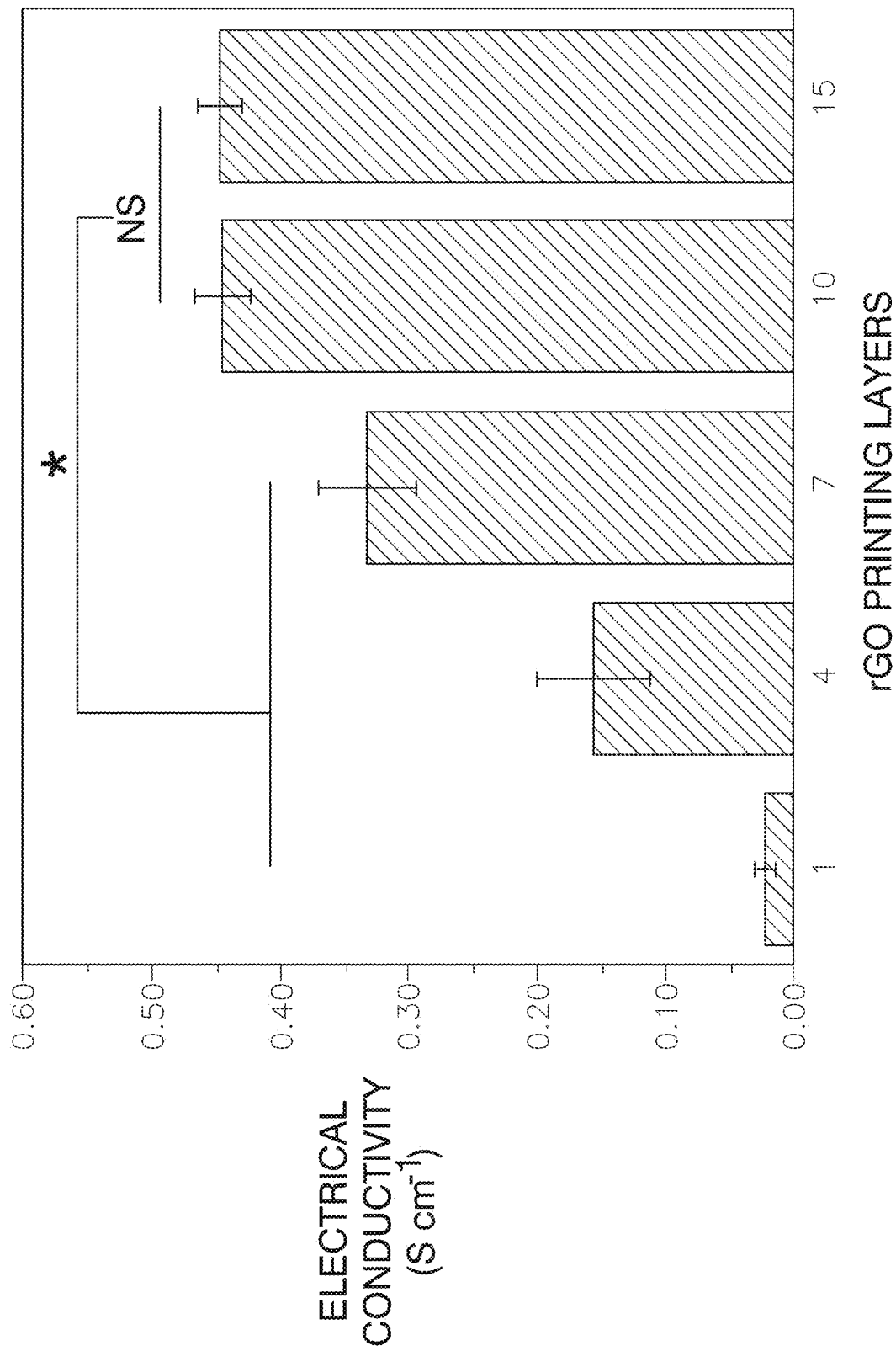
FIG. 7A is a bar graph displaying the measured electrical conductivity of rGO stripes with various printed layers in accordance with an embodiment of the present invention.
Figure 7B:
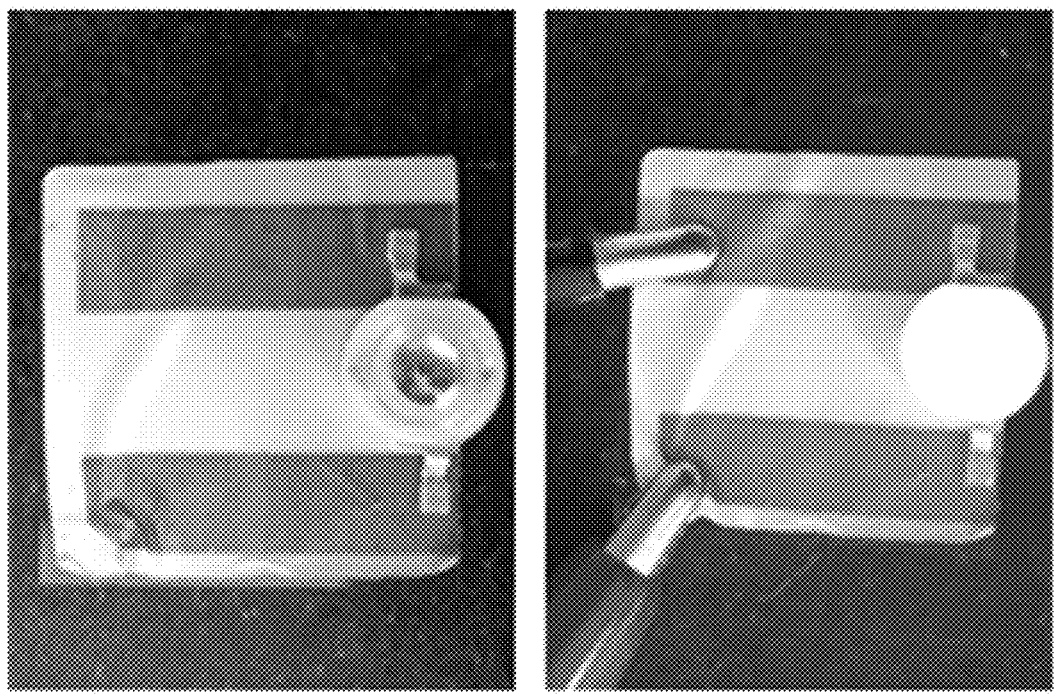
FIG. 7B is a pair of macroscopic views of a lit-up LED bulb between two 4-layer rGO stripes.

The electric conductivity of the prepared scaffolds was also measured, through a customized resistance measurement apparatus. Quantitative measurements of electrical conductivity for the different rGO printing layers are shown in FIG. 7A for inkjet-printed scaffolds. FIG. 7B shows macroscopic views of lighting up an LED lamp with 4 layers of rGO printing.

Figure 8A:
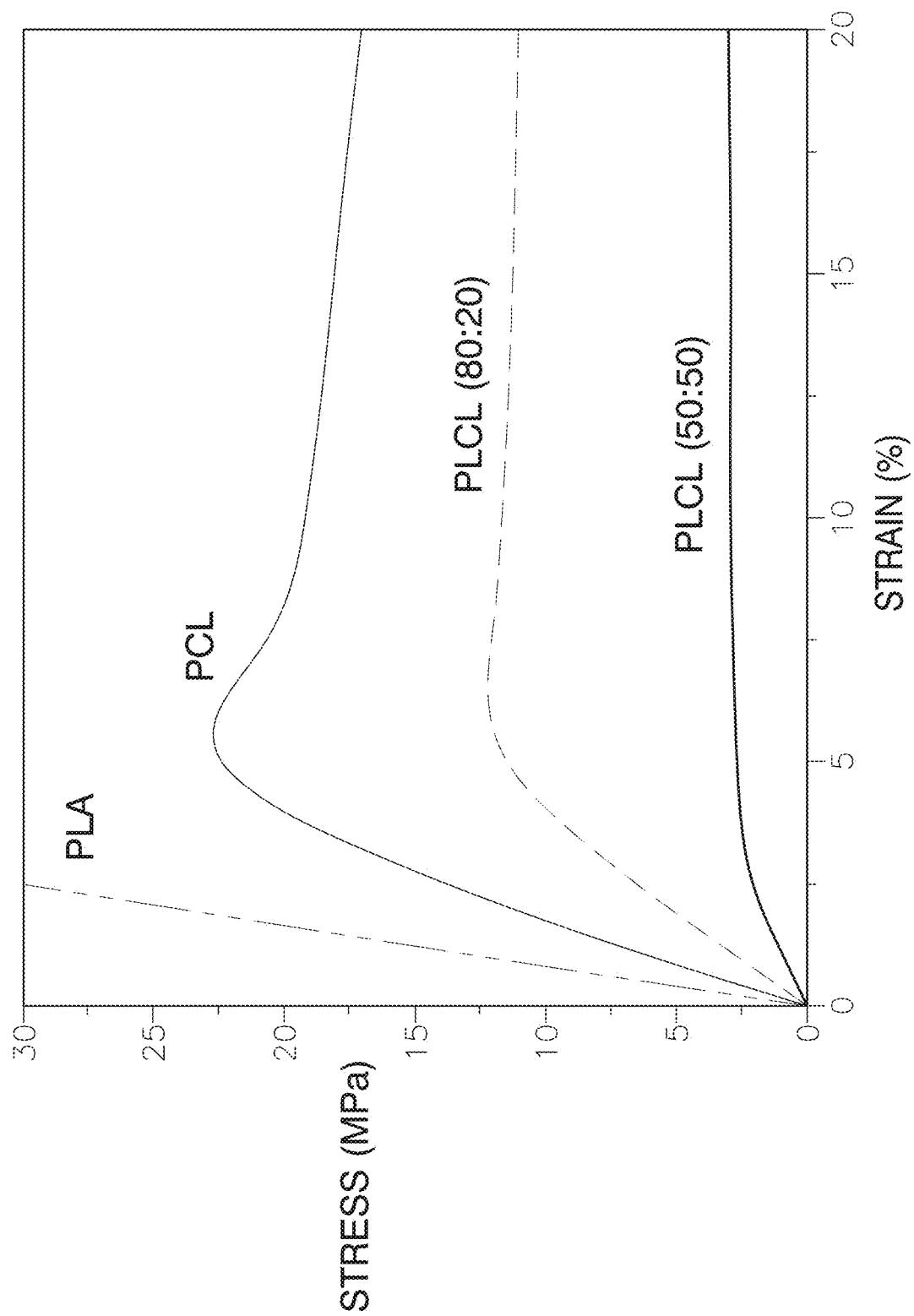
FIG. 8A is a bar graph displaying the measured stress-strain curve of exemplary materials that could be utilized as substrate materials for inkjet printing in accordance with an embodiment of the present invention.
Figure 9A:
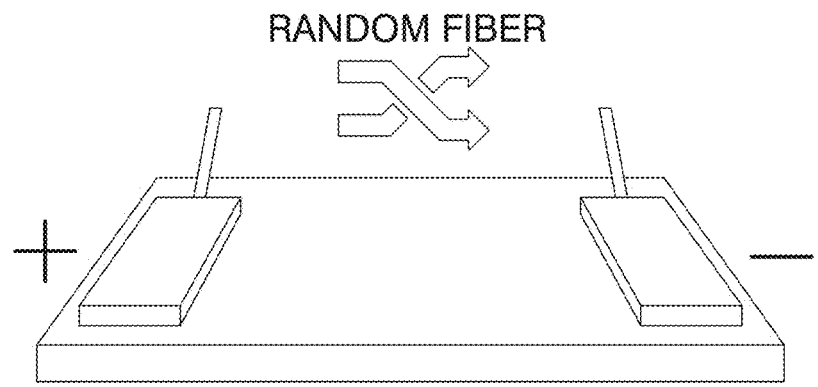
FIGS. 9A-9C are schematic illustrations of conditions for different rGO printed patterns, which figures correspond to FIGS. 9D-9G, FIGS. 9H-9K, and FIGS. 9L-9O, respectively.
Figure 9B:
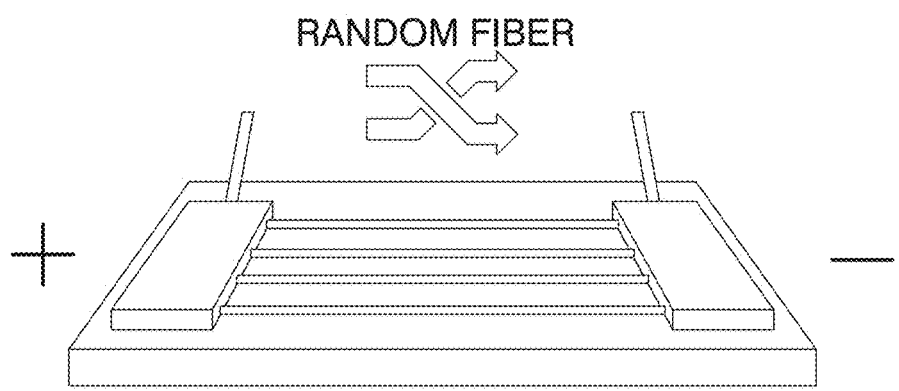
Figure 9C:
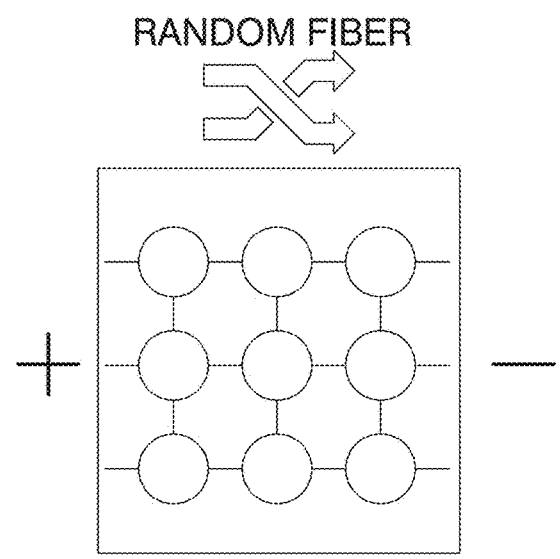
Figure 9F:
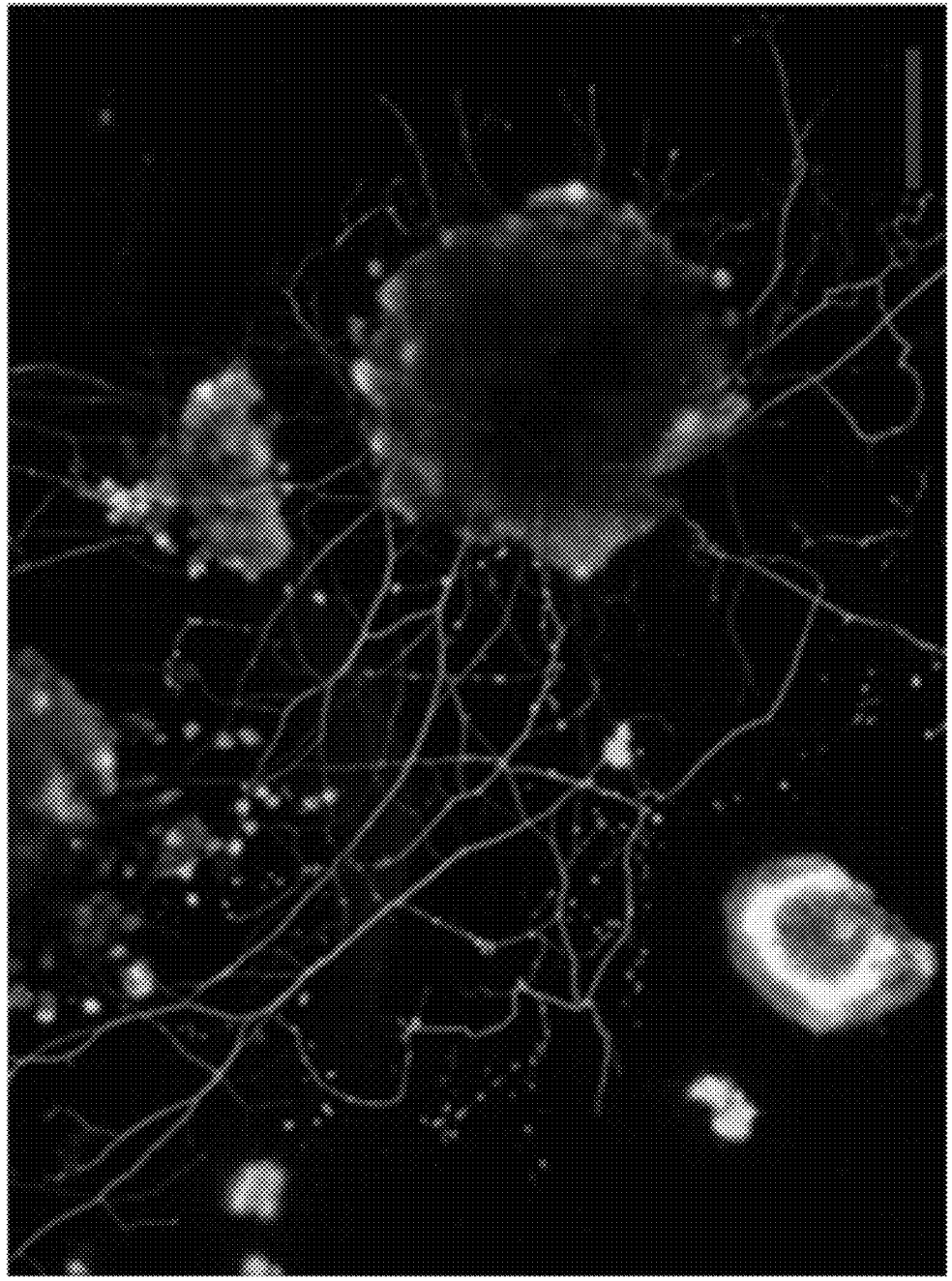
Figure 9H:
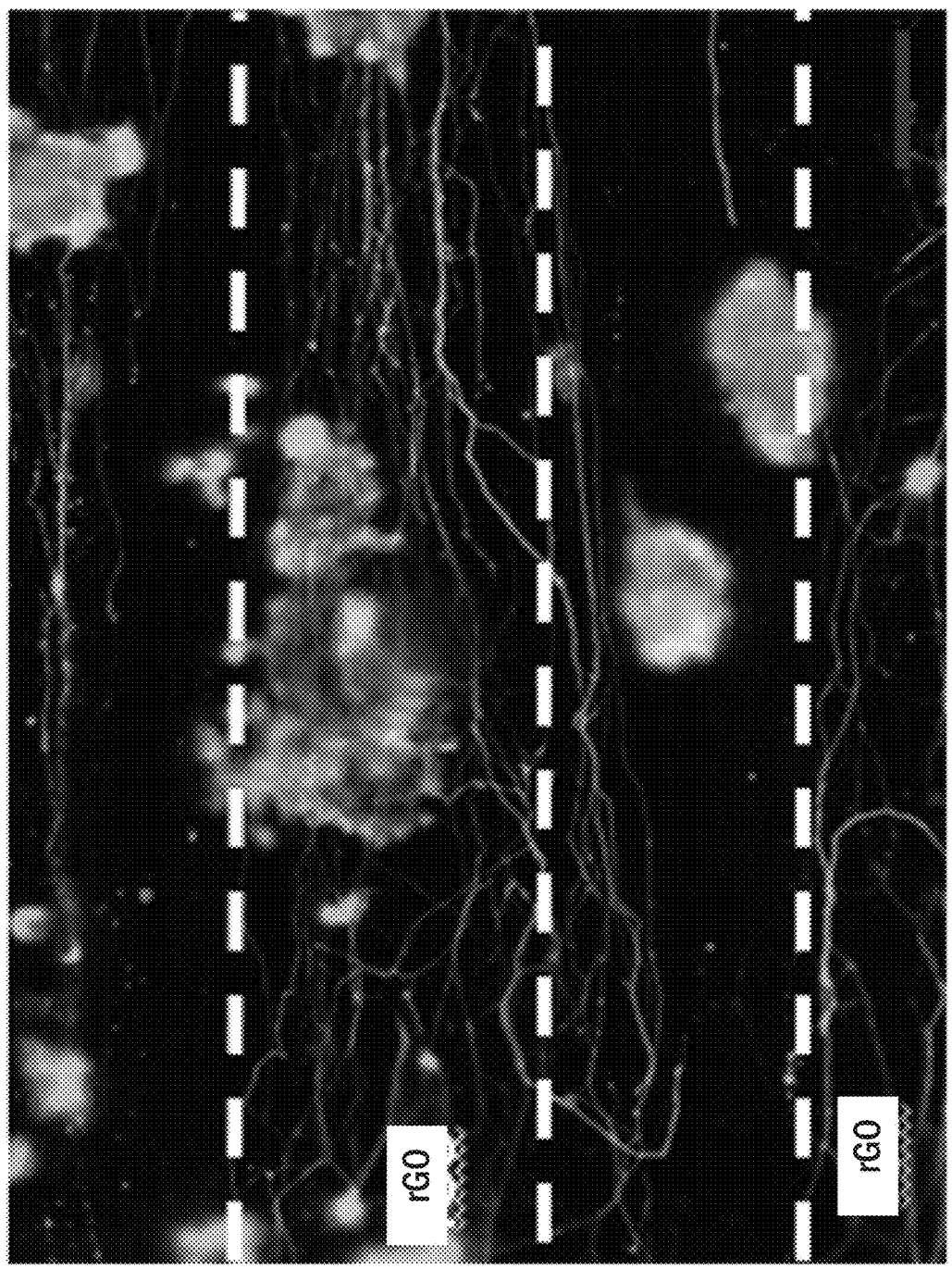
Figure 9J:
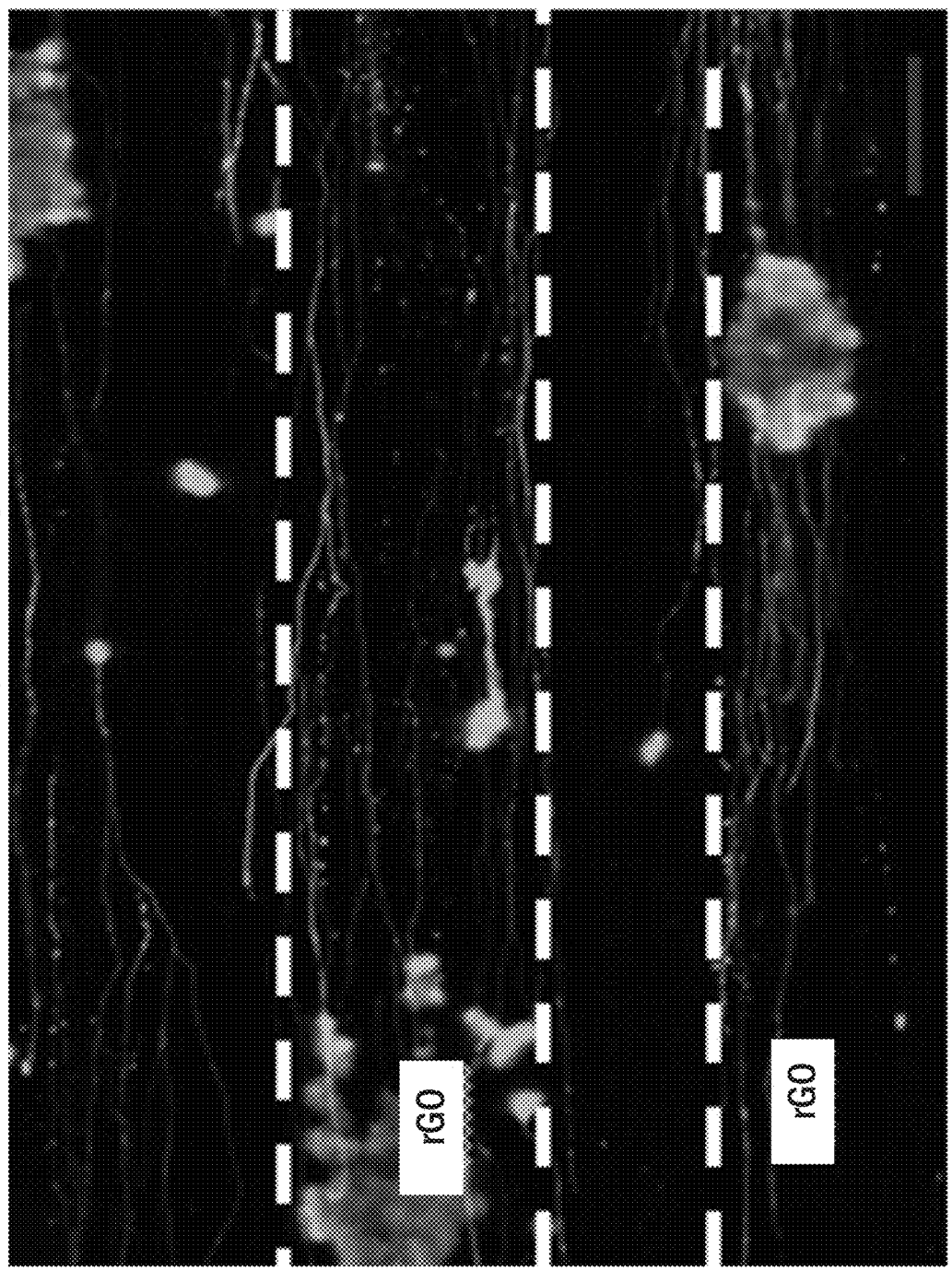
Figure 9M:
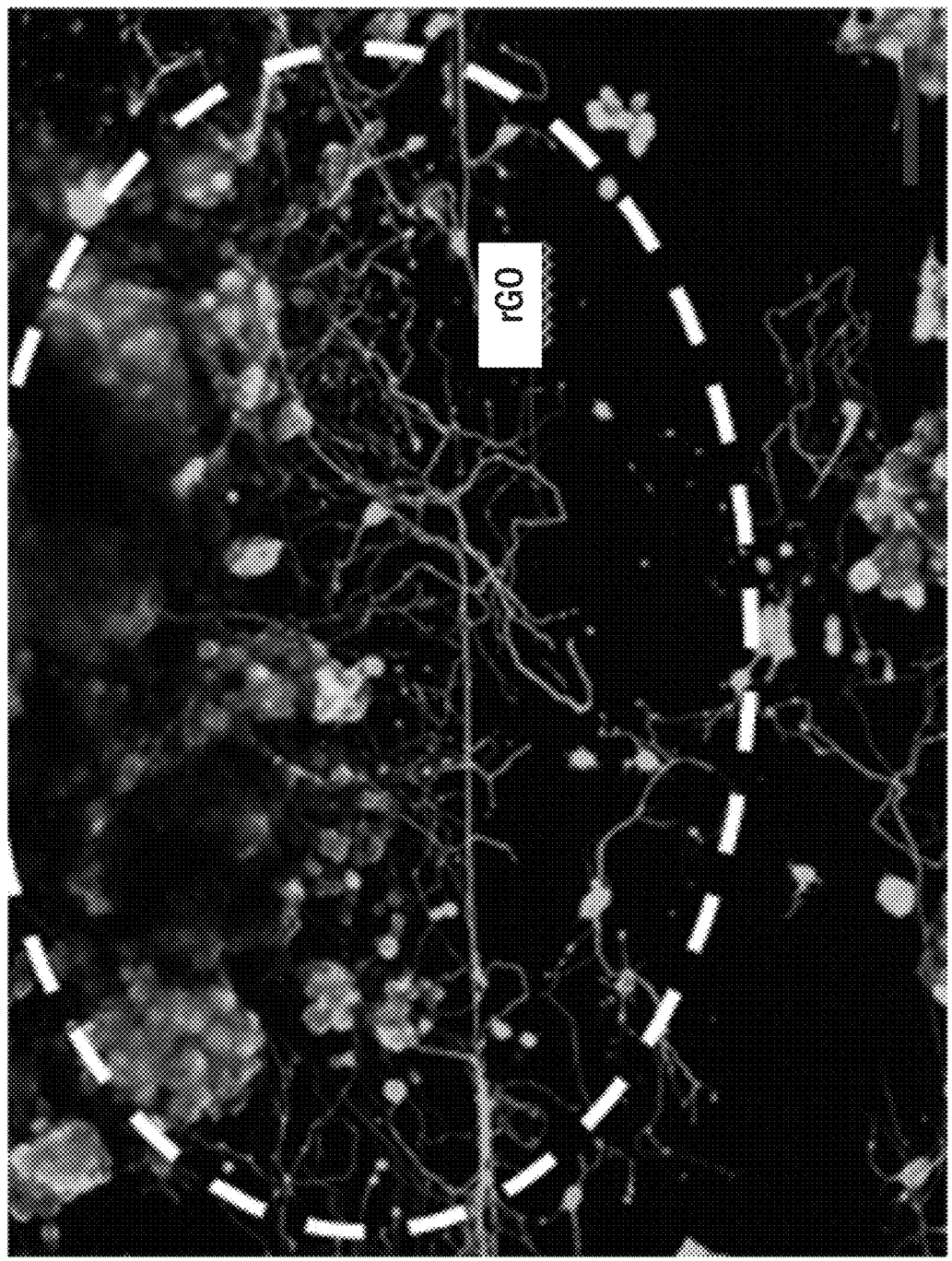
Figure 90:
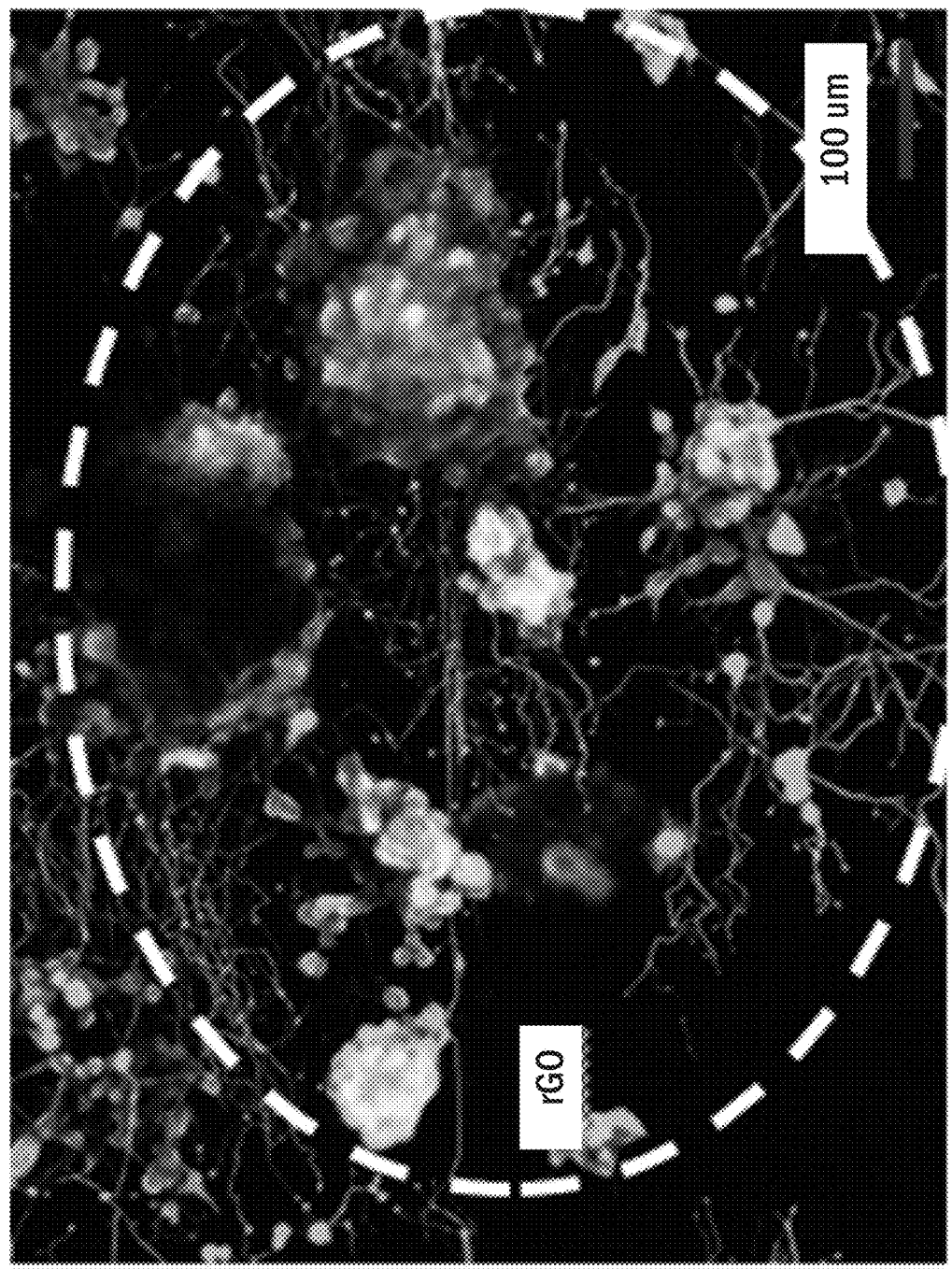

The mechanical properties of PLCL (50:50) as an inkjet printing substrate was also measured through comparison with other substrate materials (i.e., polylactic acid (PLA), polycaprolactone (PCL), and PLCL (80:20)). FIG. 8A shows the stress-strain curve for the materials. The quantitative measurements of recovery testing for the substrate materials are illustrated in FIG. 8B.

Figure 13:
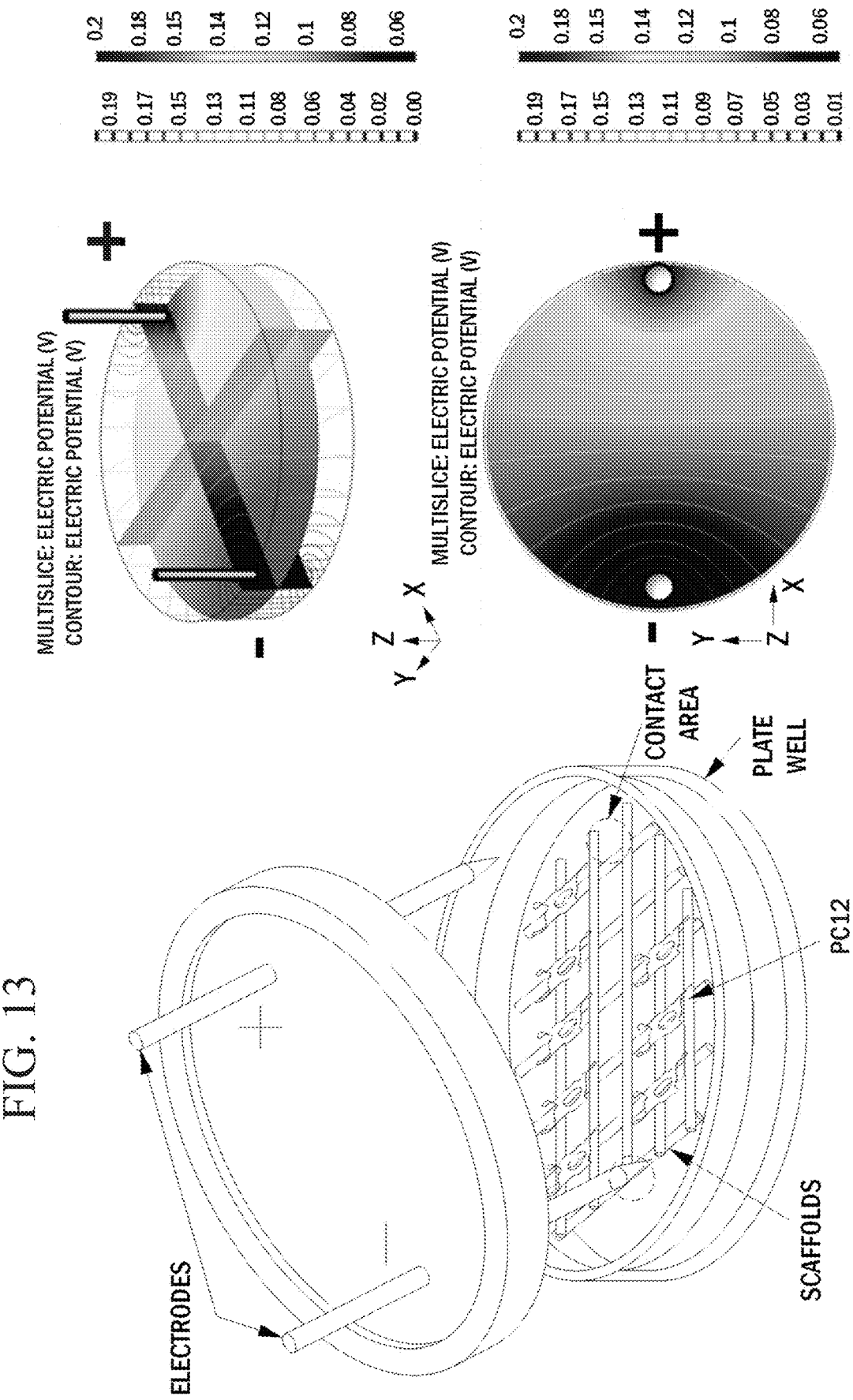
FIG. 13A is a schematic illustration of an electrical stimulation apparatus used in connection with an embodiment of the present invention.
FIGS. 13B and 13C are color maps of applied electrical stimulation in accordance with an embodiment of the present invention.
Figure 14A:
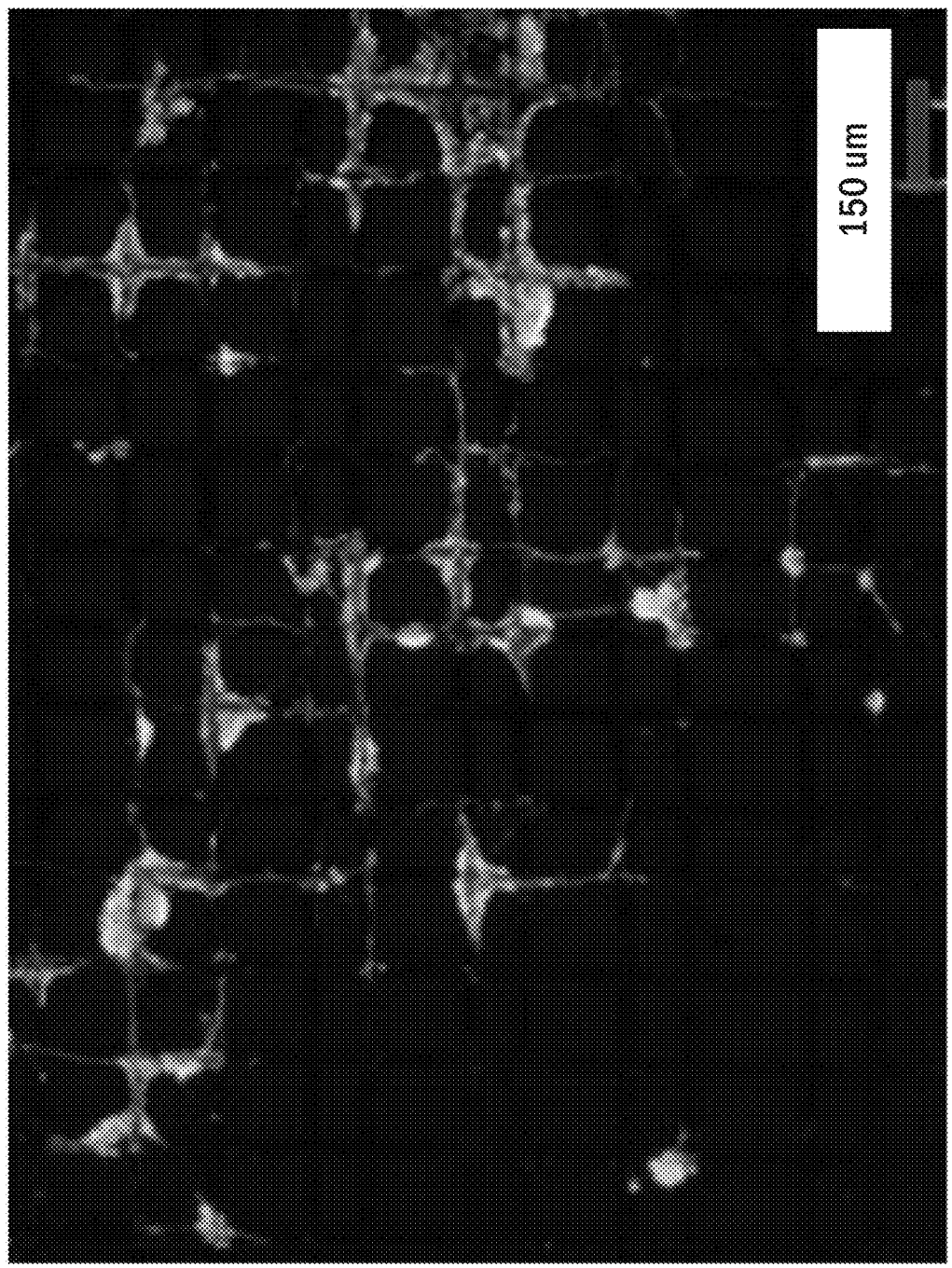
FIGS. 14A-14J are a series of immunostaining images and a corresponding intensity plot of PC12 cells seeded onto graphene oxide/reduced graphene oxide coated PLCL microfibers with different levels of electrical stimulation, in accordance with an embodiment of the present invention.
Figure 14B:
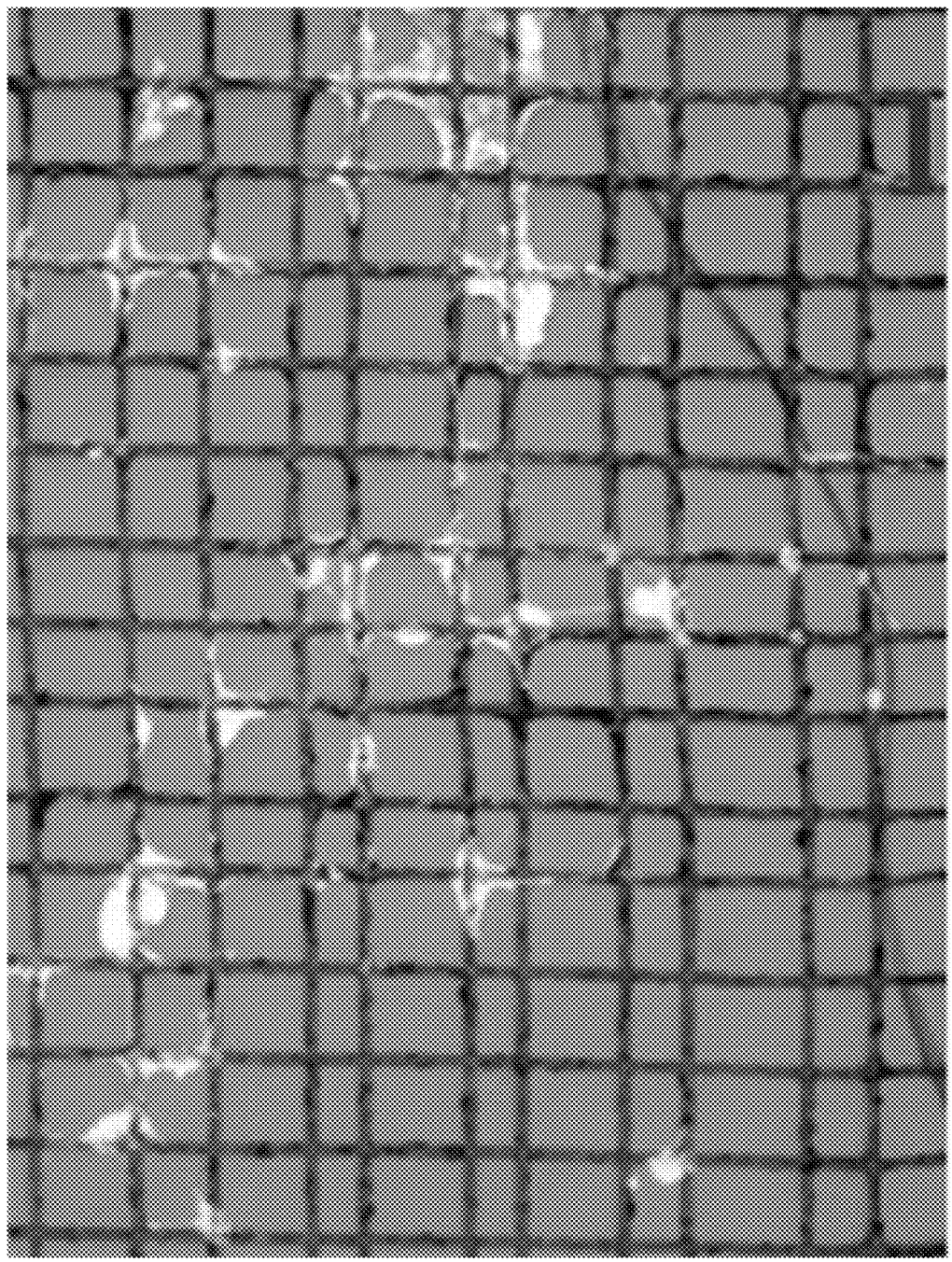
Figure 14C:
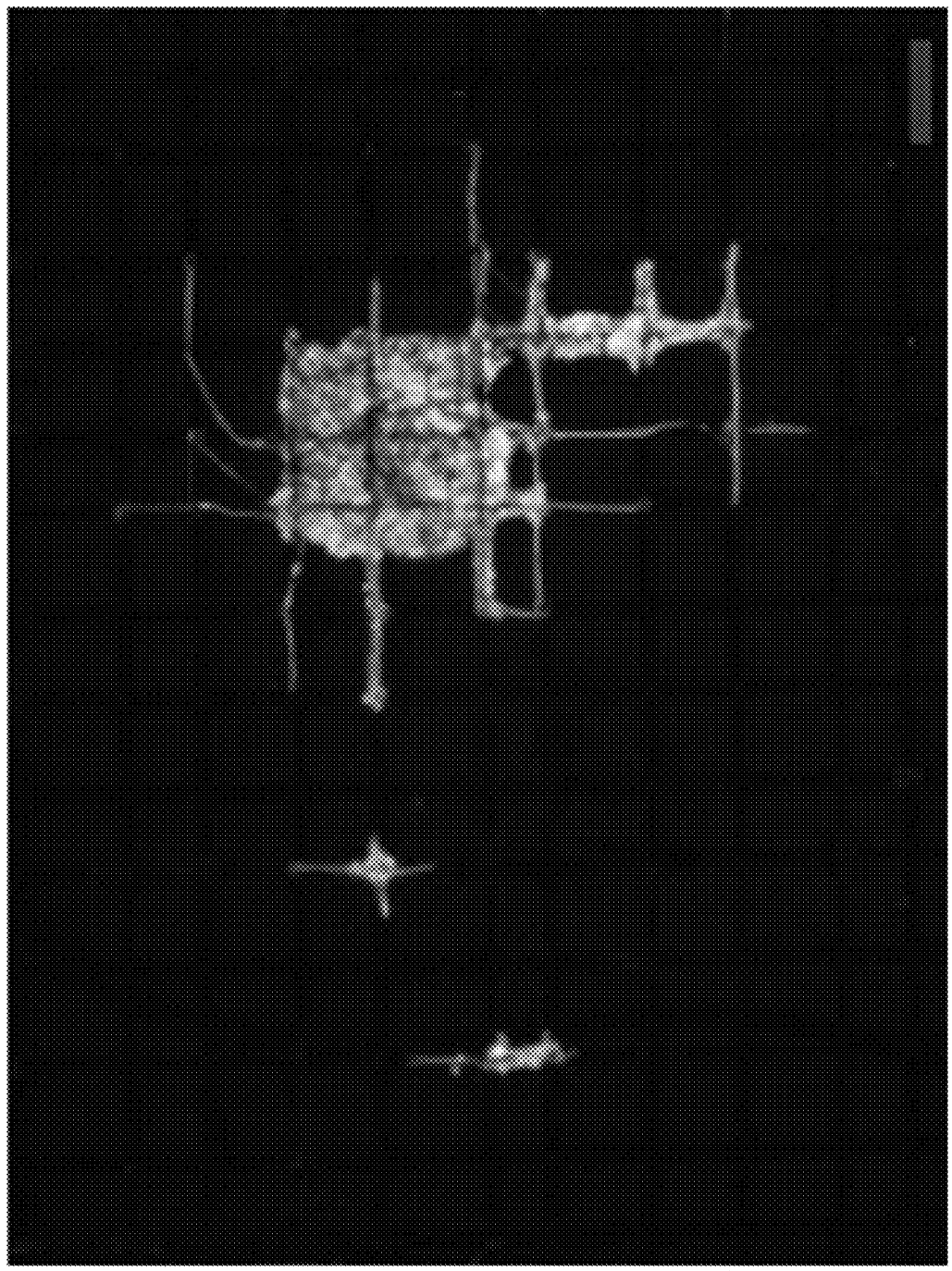
Figure 14D:
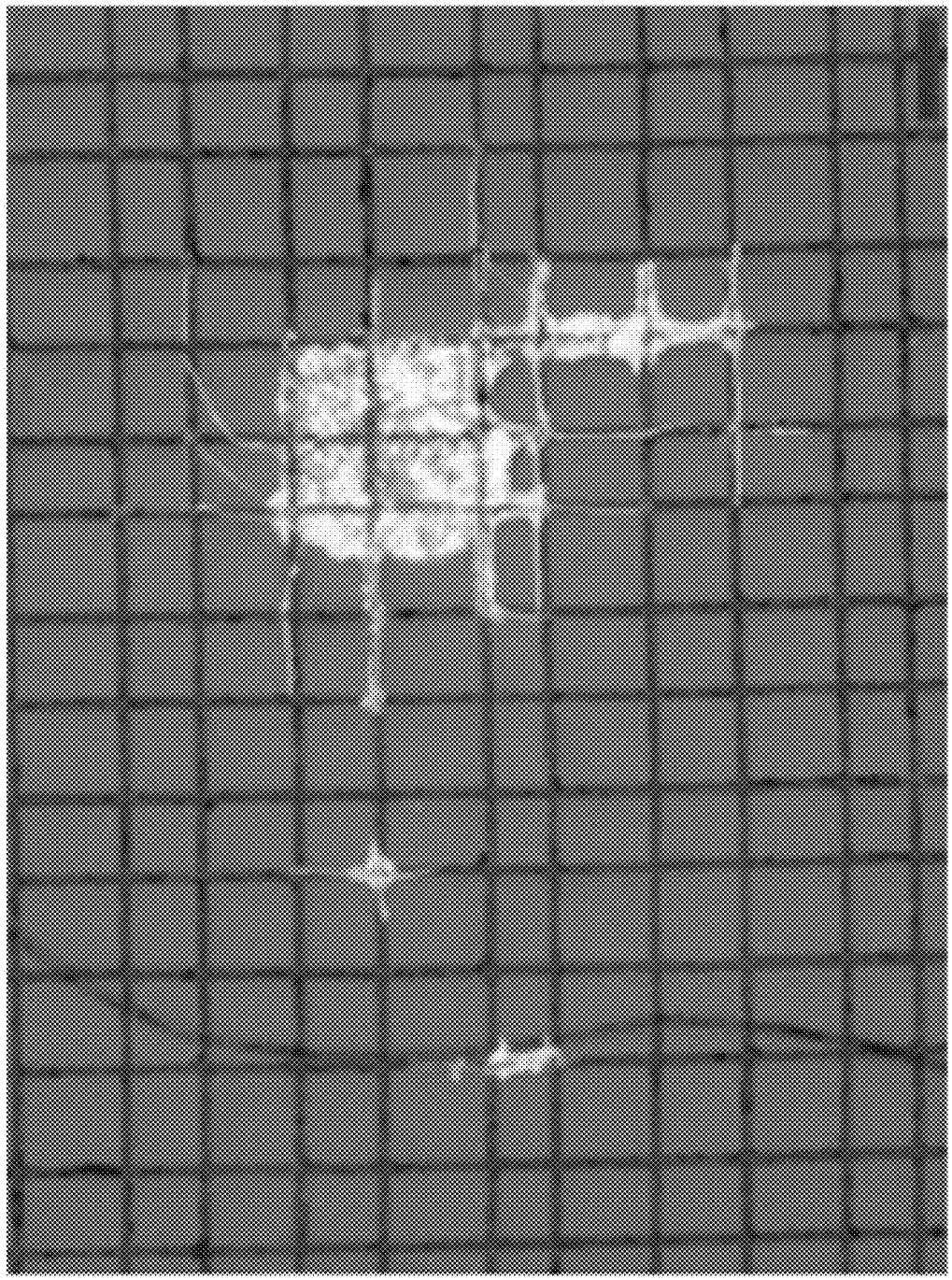
Figure 14E:
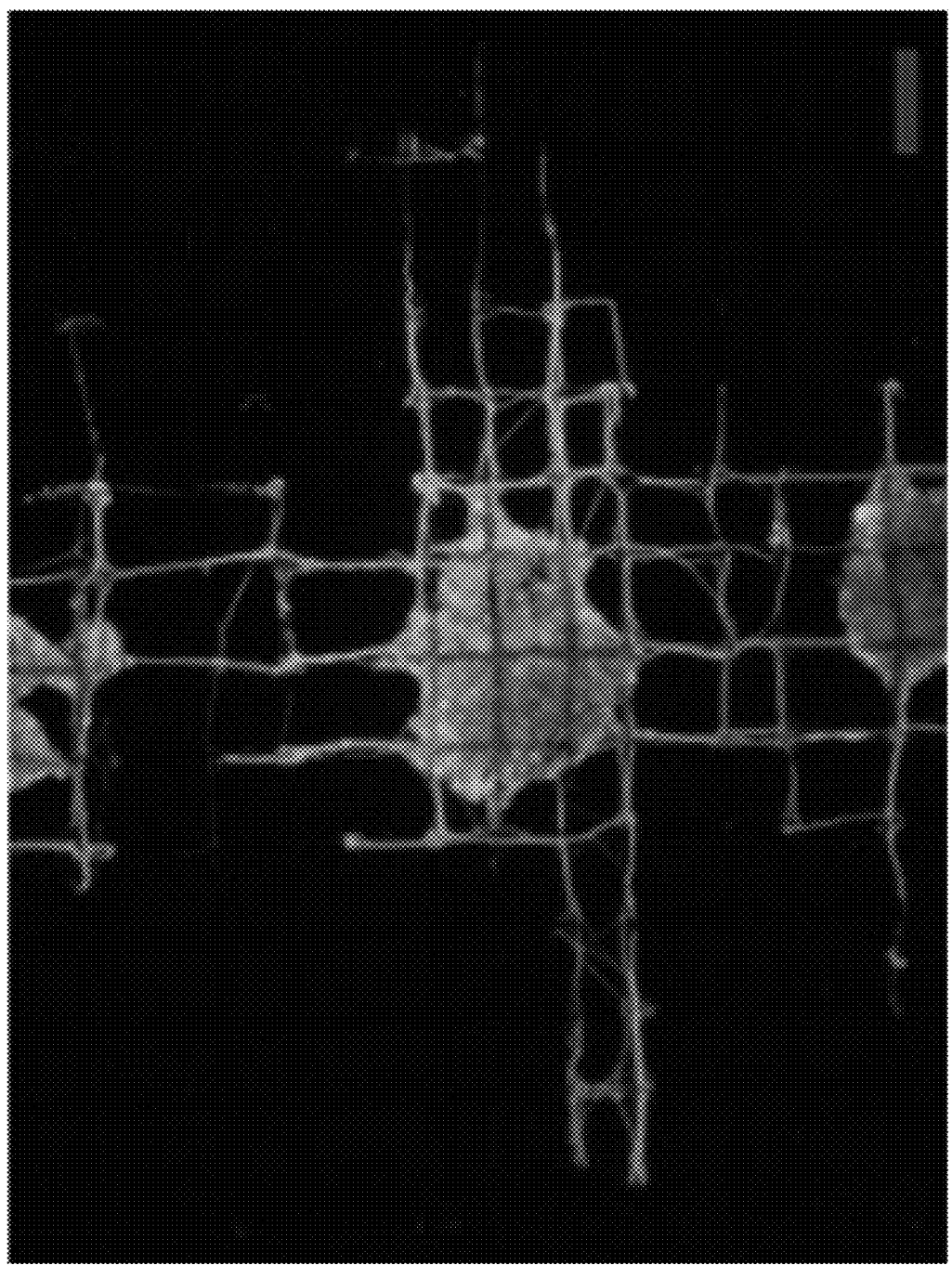
Figure 14F:
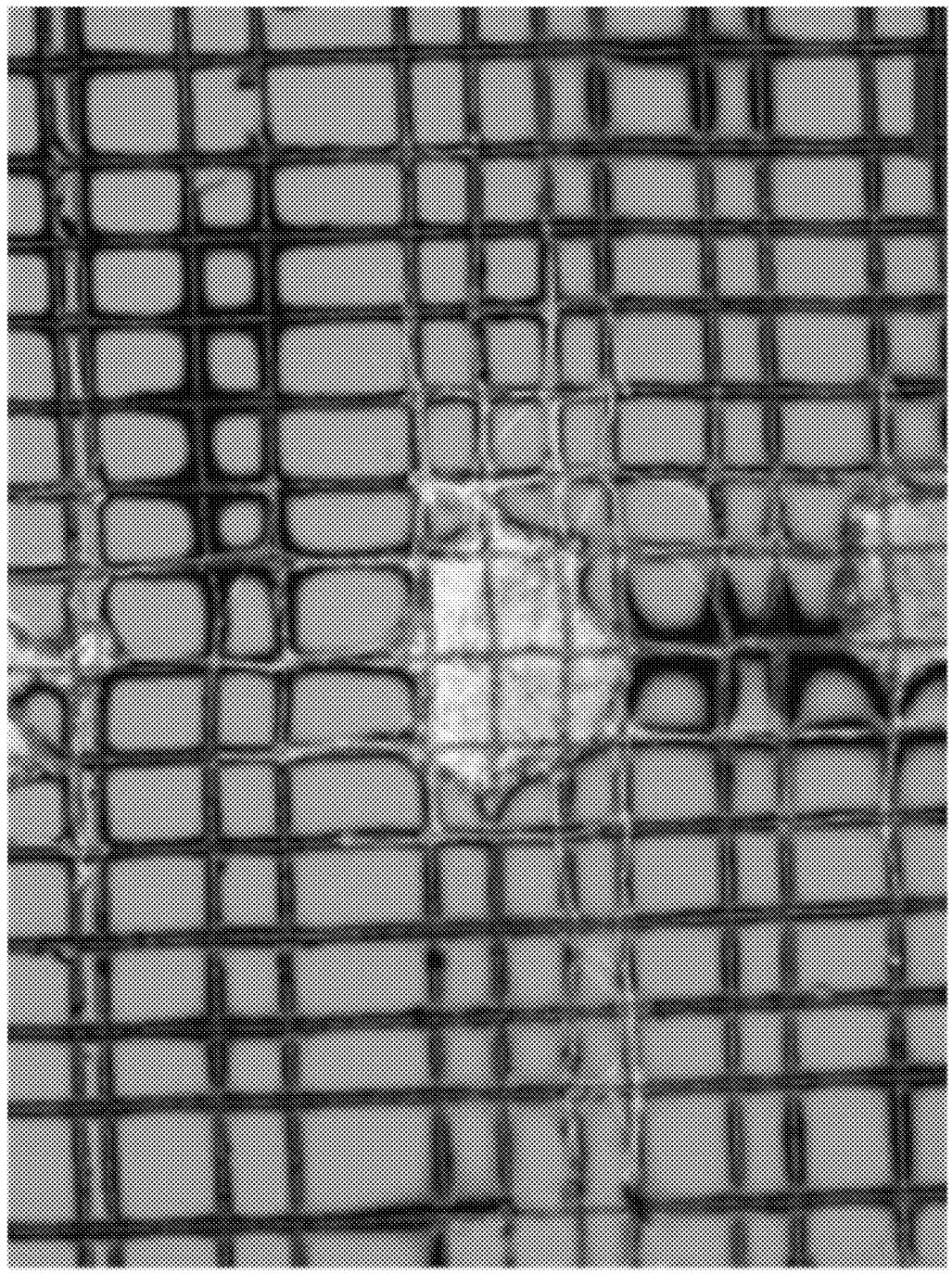
Figure 14G:
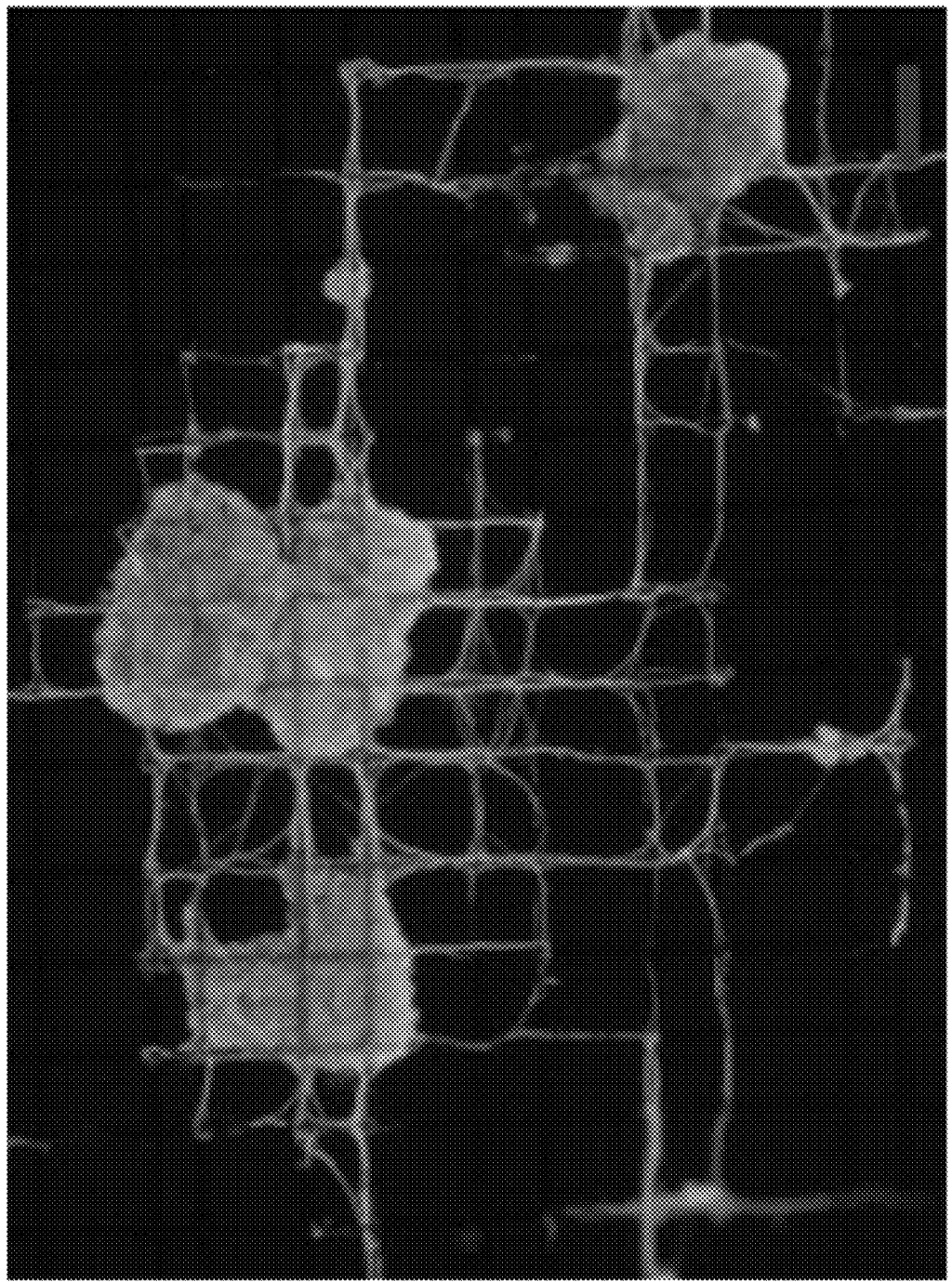
Figure 14H:
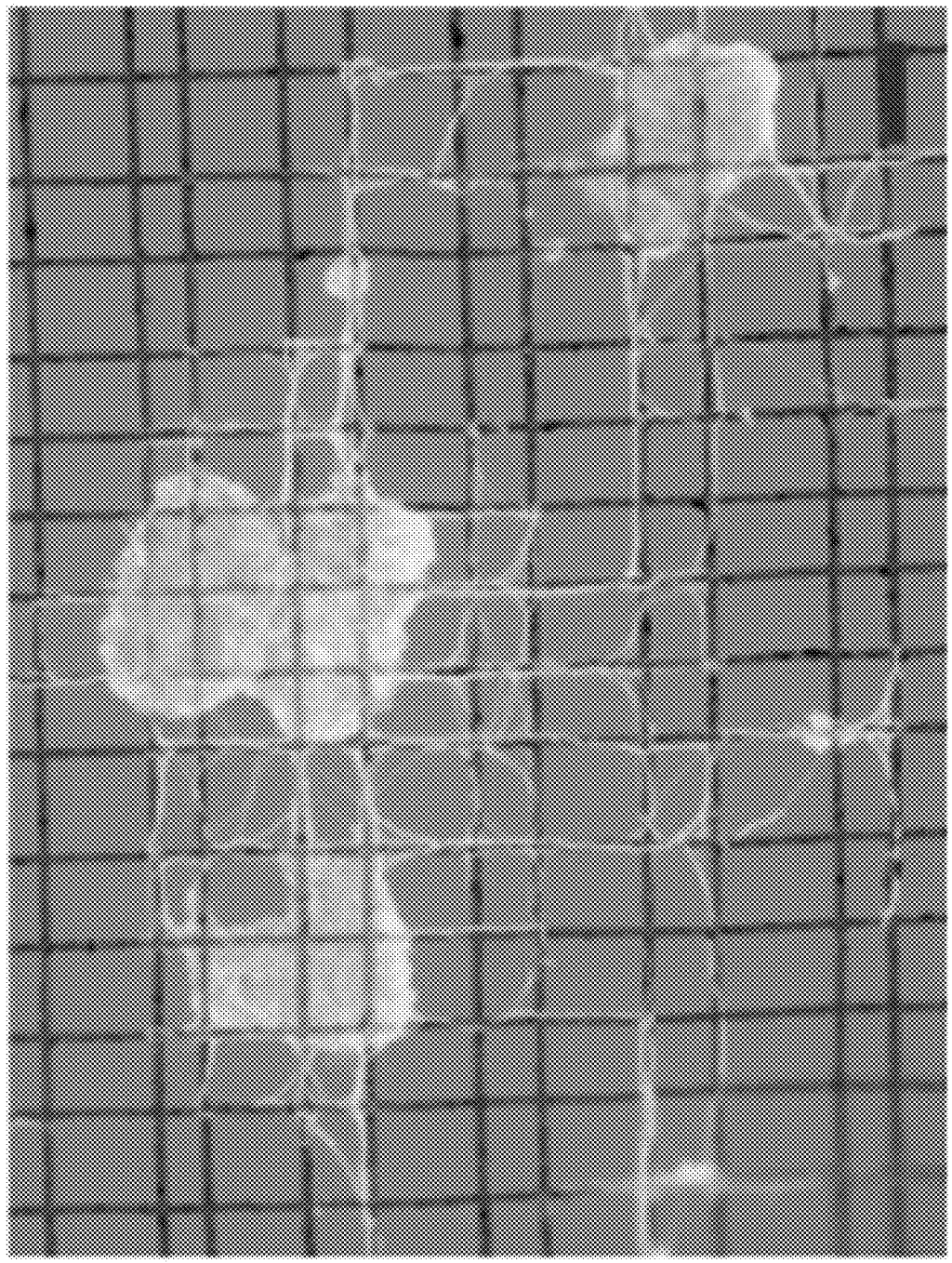
Figure 14I:
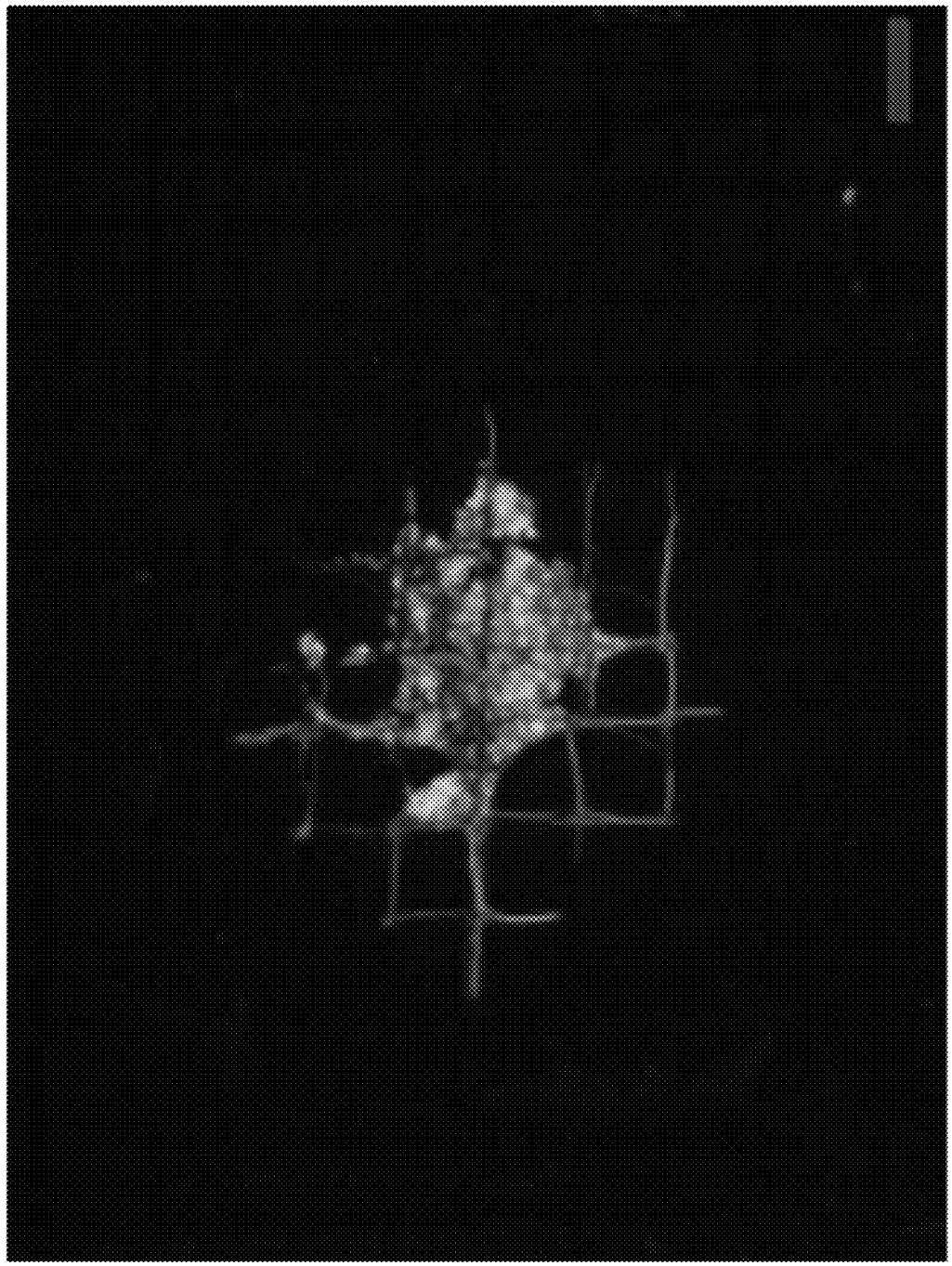
Figure 14J:
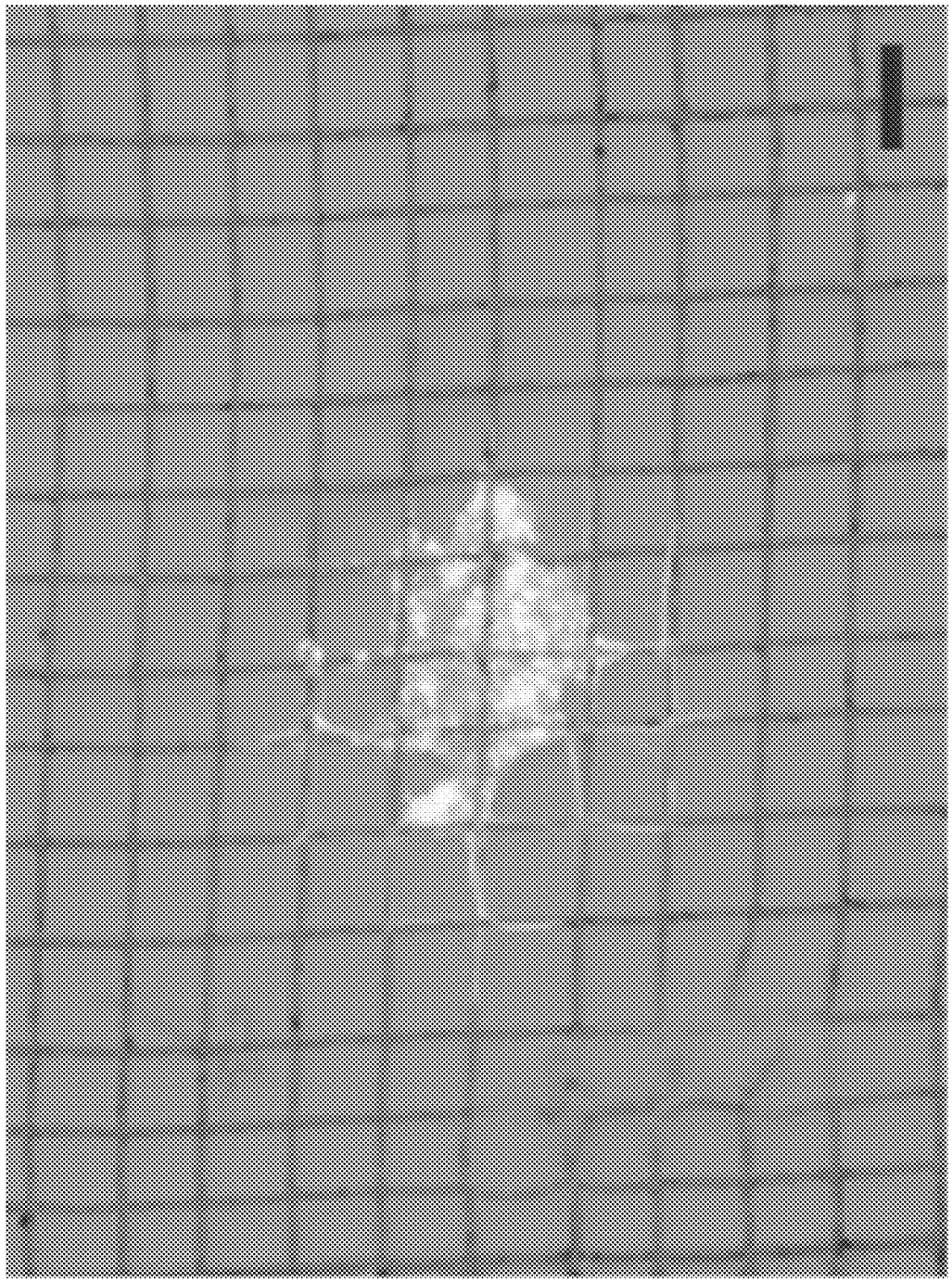

FIG. 13A is a schematic illustration of an electrical apparatus used for testing, and FIGS. 13B and 13C are simulations of electrical stimulation applied for in vitro study, showing, specifically, COMSOL simulation results for the electrical potential changes for NFEP-printed microfiber scaffolds.

Both types of scaffolds were used to culture neural cells (PC12 cells) for a designated period under the electrical stimulation and then immunofluorescently stained with biomarkers for evaluating neurite outgrowth and neural network formation.

FIG. 9 shows immunostaining for neurites after culturing PC12 cells seeded on the inkjet-printed nanofiber matrices with and without electrical stimulation for 7 and 14 days. Epifluorescent images were taken after immunofluorescently staining for nuclei (DAPI, blue), Beta tubulin III (green) and Phalloidin (red). The given scale bars correspond to 100 μm.

FIG. 14 illustrates immunostaining for neurites after 21 days culturing of PC12 cells seeded onto GO/rGO coated PLCL microfibers made with NFEP, given different electrical stimulation levels, and wherein the given scale bars correspond to 150 μm. FIG. 15 shows immunostaining for neurites after 21 days culturing of PC12 cells seeded onto GO/rGO coated NFEP-printed PLCL microfibers with various patterns. FIGS. 15A-1 to 15A-6 show epifluorescent images for microfibers with different diameters; FIGS. 15B-1 to 15B-10 show epifluorescent images for microfibers with different angles; FIGS. 15C-1 to 15C-4 show Confocal Laser Scanning Microscope images for spiderweb-like structures; and FIGS. 15D-1 to 15D-7 show Confocal Laser Scanning Microscope images for large volume cylindrical constructs (see FIGS. 15D-3 and 15D-6). Epifluorescent images and Confocal Laser Scanning Microscope images were taken after immunofluorescently staining for nuclei (DAPI, blue), Beta tubulin III (green) and Phalloidin (red). The given scale bars represent 150 μm.

Details are provided below for the fabrication of 2D conductive micropatterns on biomimetic nanofibrous matrices using inkjet printing and 3D conductive microfiber scaffolds using NFEP. Both demonstrations can be extended to other substrates with broad applicability.

Example 1—Formation of 2D Conductive Micropatterns Using Inkjet Printing

PLCL solution at 5-12% (w/v) was prepared via thorough mixing of PLCL in 1, 1, 1, 3, 3, 3-Hexafluoro-2-propanol (HFIP) for at least 12 hours prior to electrospinning. For the fabrication of nanofibrous matrices using electrospinning, the solution was transferred to a syringe equipped with a tip-blunt nozzle. The solution was pumped through the nozzle at a steady flow rate of 10 μL/min. To pull the solution into nanofibers, a high voltage of 10-20 kV was applied between the nozzle and a grounded collector, with a distance of 15 cm. The collected nanofiber matrices were vacuum dried to remove any trace amount of HFIP for further use. To form conductive micropatterns on the nanofiber matrices, aqueous solutions of graphene oxide (1-5 mg/mL) were used as the ink and loaded into the cartridge of a specialized printer (e.g., FUJIFILM Dimatix Materials Printer DMP-2800). Following pre-drawn AutoCAD patterns, graphene oxide ink was printed onto the nanofiber matrices. Optimization of the printing parameters was carried out by varying the drop distance (DD) and printing layers with various pattern combinations. After printing, the printed scaffolds were transferred to a container containing ascorbic acid solution (e.g., 10-30 mM) and reduced for 2-5 hours. After reduction, all scaffolds were rinsed with deionized water and air-dried. The reduced graphene oxide (rGO) micropatterns enabled the formation of neural networks upon the culture of neural cells on the surface with provided electrical stimulation (100-150 mV/cm). Such matrices can be further processed into tubes or other 3D structures.

Example 2—Formation of 3D Conductive Microfiber Scaffolds Using NFEP

The preparation process may be divided into three steps: NFEP of a PLCL microfiber construct, L-b-L GO-coating onto microfibers, and reduction of GO to rGO.

First, 3D microfiber constructs of PLCL are fabricated from PLCL solution (80-120 mg/mL in HFIP) using near-field electrostatic printing. The PLCL solution may be loaded into a syringe with a blunt tip nozzle and pumped through the nozzle via a syringe pump at a rate of 0.4-1 μL/min. An electric field of 1-3 kV may be applied between the nozzle and the collection surface. Close collection distance (0.5-3 mm) allows direct deposition of the stretched jet of PLCL solution onto the grounded collection surface to form 3D structures with desirable patterns upon HFIP evaporation. To form 3D tubular constructs of PLCL microfibers, the collection surface is replaced with a rotating stainless-steel rod. The printed patterns may be designed and programmed in g-code. By modulating the collection distance (H), voltage (V), nozzle diameter and solution concentration, the diameter of printed PLCL microfibers can be tuned in the range of 15-150 μm.

The obtained microfiber constructs are then coated with GO, with the help of BPEI by alternating the incubation solution between BPEI (e.g., at 1-5 mg/mL in 0.1 M phosphate buffer) and GO solution (e.g., 1-5 mg/mL). After reaching the desirable layers of GO coating, the constructs may be rinsed with 0.1 M phosphate buffer and then transferred to a container of ascorbic acid solution (e.g., 10-30 mM) and reduced for 2-5 hours. After reduction, all scaffolds may be rinsed with deionized water and air-dried. The reduced rGO microfiber constructs enable the formation of 3D neural networks upon the culture of neural cells within the scaffolds under electrical stimulation (100-150 mV/cm).

It will be understood that the embodiments described hereinabove, are merely exemplary and that a person skilled in the art may make many variations and modifications without departing from the spirit and scope of the present invention. All such variations and modifications are intended to be included within the scope of the invention.

What is claimed is:

1. A method for making an electrically-conductive scaffold, comprising the steps of:
    obtaining a biomimetic matrix, wherein said obtaining step comprises the step of printing said biomimetic matrix via near-field electrostatic printing;
    providing said biomimetic matrix with an electrically-conductive pattern of reduced graphene oxide by applying a cationic polyelectrolyte to said biomimetic matrix and directly coating said biomimetic matrix with a graphene oxide solution to form a graphene oxide coating; and
    reducing said graphene oxide coating into said pattern of reduced graphene oxide.

2. The method of claim 1, wherein said cationic polyelectrolyte comprises branched polyethylenimine.

3. The method of claim 1, wherein multiple layers of said pattern of reduced graphene oxide are formed.

4. The method of claim 1, wherein said biomimetic matrix has a three-dimensional structure.

5. The method of claim 1, wherein said biomimetic matrix is printed with a forty-five degree overlay angle.

6. The method of claim 1, wherein said biomimetic matrix is printed with a sixty degree overlay angle.

7. The method of claim 1, wherein said biomimetic matrix is printed with a seventy-five degree overlay angle.

8. The method of claim 1, wherein said biomimetic matrix is printed with a ninety degree overlay angle.

9. The method of claim 1, wherein said biomimetic matrix is printed with fiber diameters ranging from about 15 μm to about 150 μm.

10. The method of claim 1, wherein said biomimetic matrix is printed with a spider web microfiber pattern.

11. The method of claim 1, wherein said biomimetic matrix is printed with a cylindrical microfiber pattern.

12. The method of claim 1, wherein said biomimetic matrix is obtained using a layer by layer printing technique.

13. The method of claim 1, wherein said electrically-conductive scaffold comprises microfibers having microfiber diameters tailored to induce neural network formation along said microfibers under electrical stimulation.

14. The method of claim 1, wherein said electrically-conductive scaffold comprises a pattern of microfibers tailored to induce neural network formation along said microfibers of said pattern under electrical stimulation.

* * * * *